United States Patent [19]

Schaub et al.

[11] 4,076,947
[45] Feb. 28, 1978

[54] CYCLOALKYL AND CYCLOALKENYL PROSTAGLANDIN CONGENERS

[75] Inventors: Robert Eugene Schaub, Upper Saddle River; Martin Joseph Weiss, Oradell, both of N.J.

[73] Assignee: American Cyanamid Company, Stamford, Conn.

[21] Appl. No.: 758,743

[22] Filed: Jan. 12, 1977

Related U.S. Application Data

[63] Continuation-in-part of Ser. No. 457,321, Apr. 2, 1974 abandoned.

[51] Int. Cl.$^2$ .......................................... C07C 177/00

[52] U.S. Cl. .............................. 560/121; 260/345.7 P; 260/345.8 P; 260/448.8 R; 260/514 D; 260/395; 542/426; 424/305; 424/317; 560/39; 560/60; 560/84

[58] Field of Search .......... 260/468 D, 514 D, 240 R, 260/448.8 R, 345.7, 345.8, 395

[56] References Cited

U.S. PATENT DOCUMENTS

3,978,229  8/1976  Matsumoto et al. ................. 424/317

*Primary Examiner*—Robert Gerstl
*Attorney, Agent, or Firm*—Denis A. Polyn

[57] ABSTRACT

This disclosure describes novel 15-hydroxy prostanoic acids and derivatives thereof useful as bronchodilators, hypotensive agents and gastric acid secretion inhibitors (anti-ulcer).

42 Claims, No Drawings

CYCLOALKYL AND CYCLOALKENYL PROSTAGLANDIN CONGENERS

BACKGROUND OF THE INVENTION

The most closely related prior art of which applicants are aware is U.S. Pat. No. 3,966,792, which discloses certain β-chain cyclopentane and cyclohexane compounds.

BRIEF SUMMARY OF THE INVENTION

This invention relates to novel 15-hydroxy prostanoic acids and derivatives thereof as well as to intermediates and methods for their preparation. The novel prostanoic acids and derivatives of this invention embrace all the optical antipodes, diastereomers, enantiomers, racemates, racemic mixtures, and diastereomeric mixtures represented by the following general formulae:

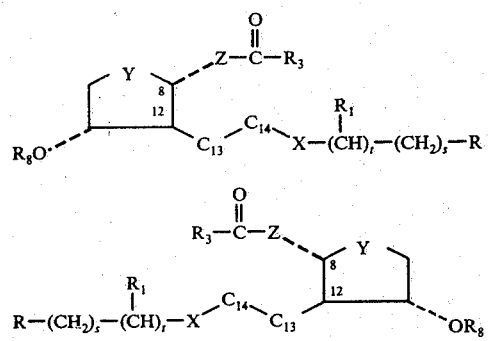

wherein Y is a divalent radical selected from the group consisting of those of the formulae:

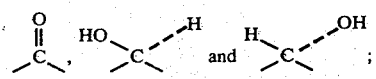

and Z is a divalent radical selected from the group consisting of those of the formulae:

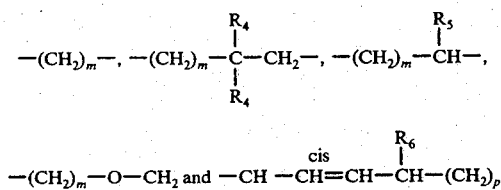

wherein $m$ is an integer from 3 to 8, inclusive, $p$ is an integer from 1 to 5, inclusive, $R_4$ is an alkyl group having up to 3 carbon atoms, $R_5$ is an alkyl group having up to 3 carbon atoms, a fluorine atom, or a phenyl group, and $R_6$ is hydrogen or an alkyl group having up to 4 carbon atoms; the moiety $—C_{13}—C_{14}—$ is ethylene or trans-vinylene; $R_1$ is an alkyl group having up to 3 carbon atoms; X is a divalent radical selected from the group consisting of

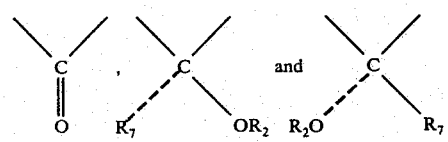

wherein $R_2$ is selected from the group consisting of hydrogen, triphenylmethyl, and mono- or di-methoxy substituted triphenylmethyl and $R_7$ is hydrogen or an alkyl group having up to 3 carbon atoms with the proviso that when $R_7$ is alkyl then $R_2$ is hydrogen; $R_3$ is hydroxy, alkoxy having from one to twelve carbon atoms, tetrahydropyranyloxy or tri-(lower alkyl)-silyloxy; $R_8$ is selected from the group consisting of hydrogen, tetrahydropyranyl, and tri(lower alkyl)silyl; $s$ is zero or an integer having the value one to five, inclusive; $t$ is zero or one; and R is selected from the group consisting of cycloalkyl groups having from three to nine carbon atoms, cycloalkenyl groups having from five to nine carbon atoms, mono- or di-(lower alkyl) substituted cycloalkyl groups having from three to eight carbon atoms in the ring, and mono- or di-(lower alkyl)substituted cycloalkenyl groups having from five to eight carbon atoms in the ring; with the second proviso that only one double bond or cyclopropyl group can be immediately adjacent to $C_{15}$ and with the third proviso that when Z is

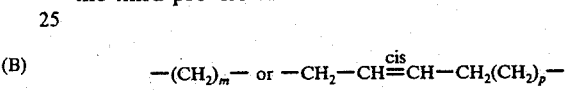

and R is a saturated cycloalkyl group then the sum of $s$ and $t$ is at least one; and the moieties

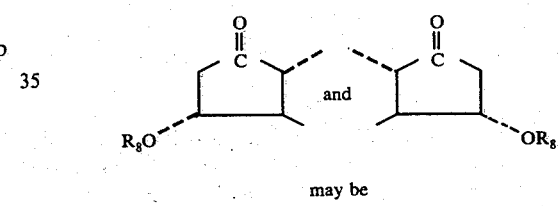

may be

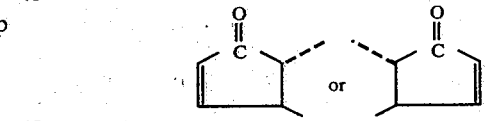

or

DETAILED DESCRIPTION OF THE INVENTION

A preferred embodiment of this invention is represented by general formulae (A) and (B) hereinabove, wherein X, Y, Z, R, $R_1$, $R_3$, $R_8$, $—C_{13}—C_{14}—$, $s$, $t$,

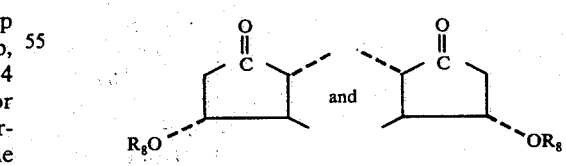

are as hereinabove defined with all the provisos assigned thereto and with the additional proviso that at least one of $R_1$, $R_4$, $R_5$, and $R_6$ is present as an alkyl group when $R_5$ is not phenyl or fluorine.

A most preferred embodiment of this invention is represented by general formulae (C) and (D), which follow.

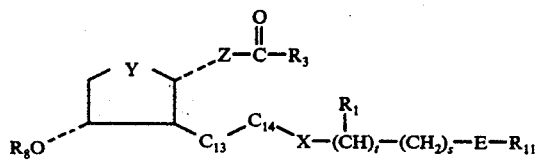

(C)

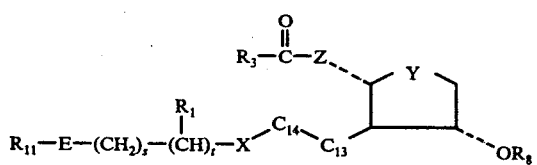

(D)

where X, Y, X, $R_1$, $R_3$, $R_8$, $C_{13}$—$C_{14}$, s, t,

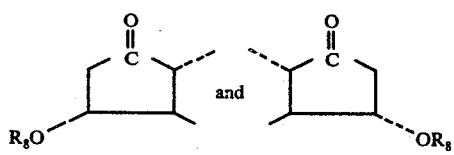

are as hereinabove defined with all the provisos assigned thereto; E is selected from the group consisting of cycloalkenyl groups having from five to nine carbon atoms and the cyclopropyl, cyclobutyl, and cyclononyl groups; and $R_{11}$ is hydrogen or a lower alkyl group; with the proviso that when E is a saturated cycloalkyl group and Z is

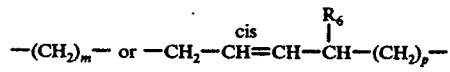

then the sum of s and t is at least one.

Suitable lower alkyl groups contemplated by the present invention are those having up to four carbon atoms such as methyl, ethyl, isopropyl, sec-butyl, and the like.

Also embraced within the scope of the present invention are the non-toxic, pharmaceutically acceptable salts of the novel compounds of the present invention when $R_3$ is hydroxy. The cations comprised in these salts include, for example, the non-toxic metal cations such as the sodium ion, potassium ion, calcium ion, and magnesium ion as well as the organic amine cations such as the tri(lower alkyl)amine cations, e.g., triethylamine, tri($\beta$-hydroxyethyl)amine, procaine, and the like. The compounds of this invention include all possible optical isomers and mixtures thereof.

The novel compounds of the present invention have characteristic absorption spectra. They are relatively insoluble in water but are relatively soluble in common organic solvents such as ethanol, ethyl acetate, dimethylformamide, and the like. The cationic salts of the compounds when $R_3$ is hydroxy are, in general, white to yellow crystalline solids having characteristic melting points and absorption spectra. They are relatively insoluble in water, methanol, and ethanol but are relatively insoluble in benzene, diethyl ether and petroleum ether.

In the above general formulae, the two side chains attached to the $C_8$ and $C_{12}$ positions of the cyclopentane or cyclopentene ring are trans to each other. When the side-chain is attached to $C_8$ or $C_{12}$ by a ---- bond, then it is considered to be behind the plane of the paper. When it is attached by a — bond, then it is considered to be in front of the plane of paper. Thus, all such isomers of trans configuration are included within the purview of the present invention. For the sake of convenience, in subsequent formulae only one isomer may be represented.

The prostaglandins are a family of closely related compounds which have been obtained from various animal tissues and which stimulate smooth muscle, lower arterial blood pressure, antagonize epinephrine-induced mobilization of free fatty acids, and have other pharmacological and autopharmacological effects in mammals. See Bergstom et al., J. Biol. Chem. 238, 3555 (1963) and Horton, Experientia 21, 113 (1965) and references cited therein. All of the so called natural prostaglandins are derivatives of prostanoic acid:

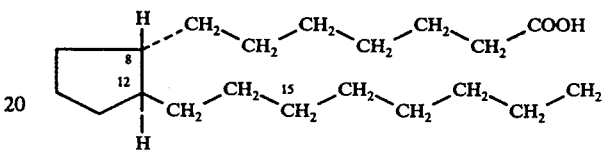

The hydrogen atoms attached to C-8 and C-12 are in trans-configuration. The natural prostaglandins represent only one of the possible optical isomers. The compounds of this invention include all possible optical isomers.

The $C_{15}$ position is a particularly important one and when it is substituted by a hydroxy or a blocked hydroxy group and a hydrogen atom or lower alkyl group ($R_7$) it is assymetric with the possibility of two configurations, deemed S or R. In partial formulae (E) below is shown the "normal" configuration of $C_8$, $C_{12}$, and $C_{15}$ as it is found in all known mammallian prostaglandins. The configuration at $C_8$ and $C_{12}$ is referred to as l and at $C_{15}$ as S; thus formulae (E) is the l 15(S) form. The enantiomer of (E) is represented by partial formula (F), and d 15(R) form, and a substance deemed a dl--racemate without designation with regard to the situation at $C_{15}$ consists of (E) and (F). Partial formula (G) represents a structure wherein the configuration at $C_8$ and $C_{12}$ is as in (E), the l form, but the configuration at $C_{15}$ is inverted to the R form. A structure embracing the configuration at $C_8$, $C_{12}$, and $C_{15}$ as shown in (G) is referred to as an l 15-epi derivative, the enantiomeric structure is represented by partial formula (H), the d 15-epi derivative, and (G) and (H) is a dl-15-epi racemate.

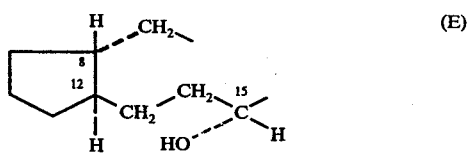

(E)

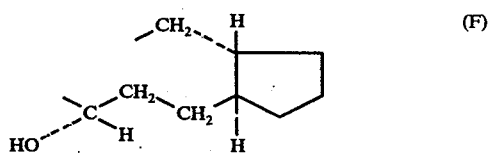

(F)

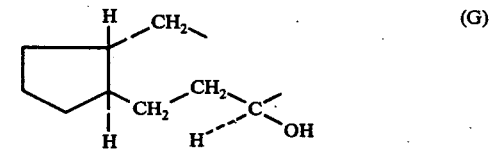

(G)

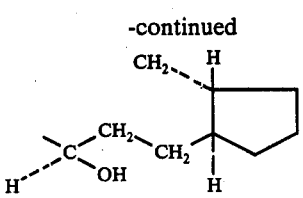

The compounds of this invention include both possible configurations for $C_{15}$.

The novel compounds of the present invention may be readily prepared from certain 4-oxycyclopentenone intermediates, some of which may be represented by the following general formula:

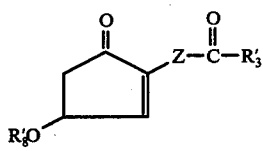

wherein Z is as defined above, and $R'_3$ has all the possibilities given above for $R_3$ except that it is not hydroxy, and $R'_8$ has all the possibilities given above for $R_8$ except that it is not hydrogen.

Those 4-oxycyclopentenones wherein Z does not embrace a carbon-carbon double bond are prepared from the corresponding 4-unsubstituted cyclopentenone acids or esters. The preparation of certain of these cyclopentenones is described in Belgium Pat. No. 786,215 (granted and opened to inspection Jan. 15, 1973). Others of the requisite cyclopentenones are prepared by extension of the methods described therein. Introduction of the requisite 4-oxy function is illustrated in Flowsheet A, below, wherein Z' has all the possibilities given above for Z except that it does not include

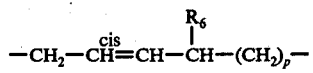

$R'_3$ and $R'_8$ are as described hereinabove and $R''_3$ is hydroxy or alkoxy having from one to twelve carbon atoms.

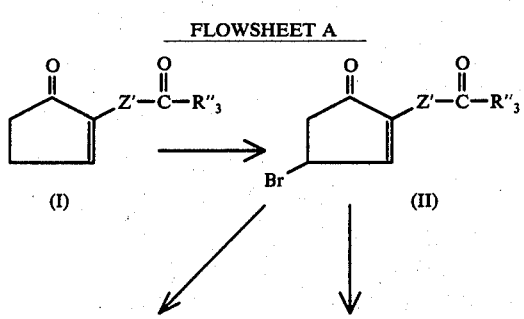

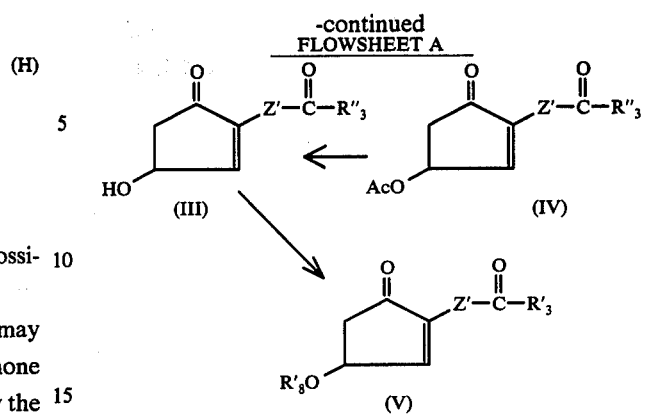

Introduction of the 4-oxy function into the 4-unsubstituted cyclopentenones (I) is accomplished by first halogenating the 4-position with an allylic halogenating reagent, preferably N-bromosuccinimide. The resulting 4-bromocyclopentenone (II) is then solvolyzed for the introduction of the oxy function. This step is preferably carried out in the presence of a silver salt to facilitate the displacement of the halide ion. The particular 4-oxy derivative that is formed is determined by the nature of the solvent system. Treatment of the 4-bromocyclopentenone with silver fluoroborate in water-acetone (for solubility) provides the 4-hydroxycyclopentenone (III). When solvolysis is carried out with a silver lower alkanoate in the corresponding lower alkanoic acid, such as the silver acetate-acetic acid system, the 4-lower alkanoyloxy (4-acetoxy) derivative (IV) is obtained. Careful alkaline hydrolysis of this product with potassium carbonate in aqueous methanol provides the free 4-hydroxy derivative (III); when $R''_3$ is lower alkyl further hydrolysis with barium hydroxide gives the free carboxylic acid (III, $R''_3$=hydroxy).

In general these procedures are operable with either the free carboxylic acid or alkyl carboxylate, as desired. A particular alkyl carboxylate not provided by formula (III) can be obtained by hydrolysis to the acid and esterification in the usual way, for example with the appropriate diazoalkane or alcohol, or for a t-butyl ester with isobutylene. However, for the subsequent alanate conjugate addition process it is necessary to utilize a cyclopentenone wherein the carboxylic acid as well as all free hydroxyl groups are blocked. Particularly useful blocking groups for both functions are the tetrahydropyranyl group or tri(lower alkyl)silyl groups since these groups can easily be cleaved with weak acid under conditions which do not disrupt the subsequently-prepared, relatively-unstable 11-oxy-9-keto system ($\beta$-hydroxyketone). Thus, it is not possible to effect a satisfactory chemical hydrolysis of an alkyl ester or of an 11-O-alkanoyl group in an 11-oxy-9--keto prostanoic acid derivative under conditions to which this system is stable. However, enzymatic or microbiological hydrolysis is possible and of course these stability considerations do not apply in the "F" (9-hydroxy) series. Appropriately blocked 4-oxycyclopentenone derivatives are represented by formula (V).

The preparation of the 4-oxycyclopentenone intermediates wherein Z is $$-CH_2-\overset{cis}{CH}=CH-\overset{R_6}{\underset{|}{CH}}-(CH_2)_p-$$

is illustrated in Flowsheet B, which follows, and in which $R_6$, p, $R'_3$ and $R'_8$ are as hereinabove defined.

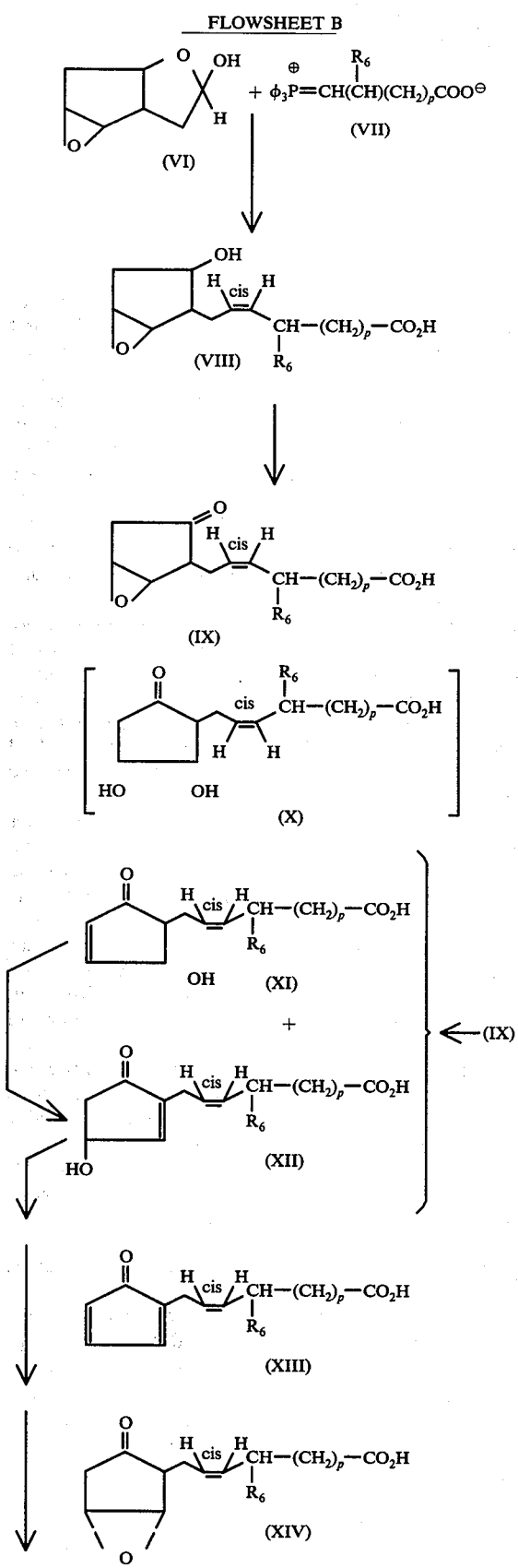

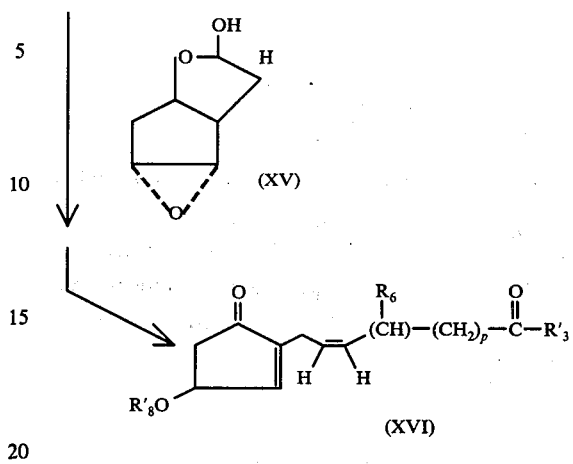

In accordance with the above reaction scheme the 3,4-epoxylactol (VI) [E. J. Corey and R. Noyori, *Tetrahedron Letters*, 311 (1970)] is treated with the ylide (VII) to give the 3,4-epoxycyclopentanol (VIII). Oxidation (for example with $H_2CrO_4 \cdot H_2SO_4$-ether or Jones reagent) of (VIII) provides the epoxy ketone (IX), mild base treatment of which results in the initial formation of the 4-hydroxycyclopent-2-en-1-one (XII) and the isomeric 3-hydroxycyclopent-4-en-1-one (XI) as a mixture. Further treatment of this mixture with dilute base under mild conditions results in the isomerization of the 3-hydroxy isomer (XI) to the desired (XII). The transformation of the epoxy ketone (IX) to the hydroxycyclopentenones (XI) and (XII) and the isomerization of (XI) to (XII) may take place through the intermediacy of the 3,4-diol (X). It is also conceivable that isomerization of (XI) to (XII) proceeds via the epoxy derivative (IX) or the corresponding α-epoxide (XIV); it is further conceivable that (IX) proceeds to (XI) and (XII) directly without the intermediacy of (X). Another possible intermediate for the isomerization of (XI) to (XII) is the corresponding diene (XIII). The preparation of (XII) is also possible via the α-epoxide series from (XV) via the α-epoxides corresponding to (VIII) and (IX) such as (XIV) or moxt conveniently via a mixture of the α- and β-epoxides. The hydroxy and acid function in the 4-hydroxycyclopentenones (XII) are then blocked to give (XVI). Suitable blocking groups for the hydroxy and acid functions are tetrahydropyranyl, trimethylsilyl, dimethyl-isopropylsilyl, dimethyl-t-butylsilyl and the like; the carboxylic acid group also can be converted to the corresponding alkyl ester.

The 9-keto-13-trans-prostenoic acids and esters of this invention may be prepared by the novel conjugate addition process outlined in the Flowsheet C which follows. In Flowsheet C, R, $R_1$, Z, $R'_3$, $R''_3$, s and t as defined hereinabove; $R_9$ is a lower alkyl group (each of the three $R_9$ radicals bonded to an aluminum atom does not necessarily have to be the same), $R'_2$ has all the possibilities given hereinabove for $R_2$ except hydrogen, and R' has all the possibilities given hereinabove for R except that it does not include cycloalkenyl, or cyclopropyl groups.

FLOWSHEET C

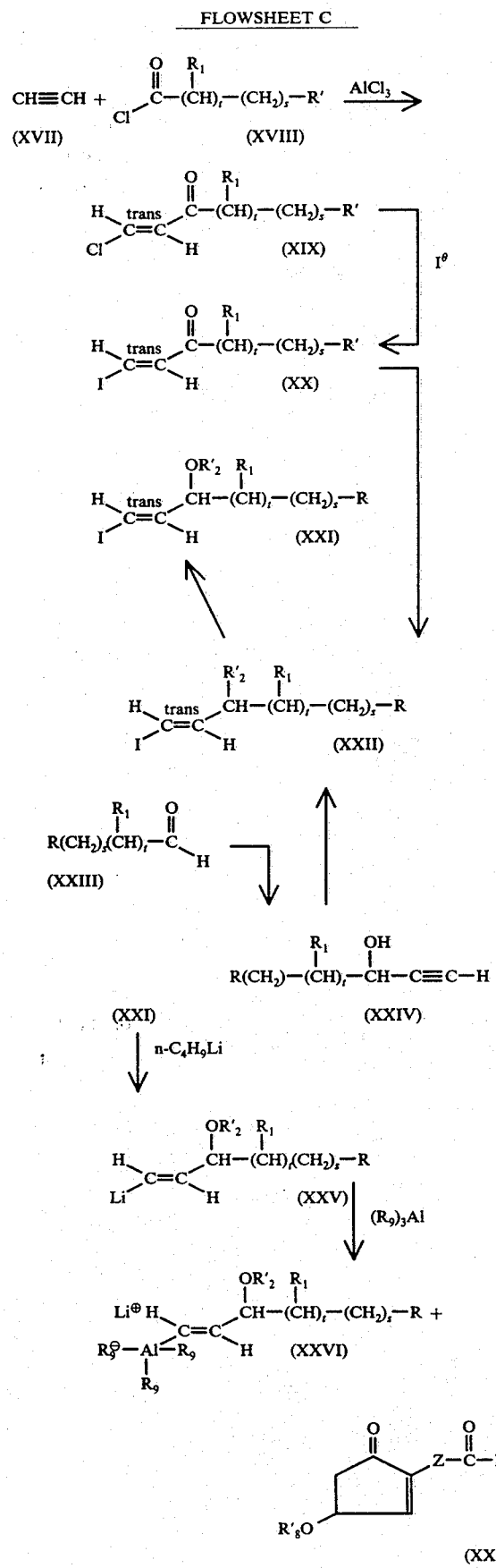

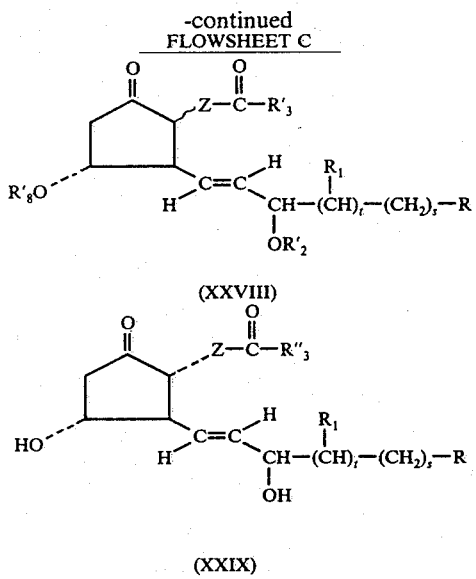

(XXIX)

In accordance with the reaction scheme of Flowsheet C, acetylene (XVII) is treated with a cycloalkyl, or a cycloalkyl substituted alkyl acid chloride (XVIII) in the presence of aluminum trichloride to provide the 1-chloro-3--keto-trans-1-alkene (XIX). Interchange with sodium iodide, preferably in a ketone solvent such as acetone, provides the corresponding trans-vinyl iodide (XX). Reduction of the keto function in (XX) with sodium borohydride furnishes the alcohol (XXII), which is then blocked with the triphenylmethyl group or a triphenylmethyl group substituted with one or two methoxy groups. Introduction of the methoxy group(s) increases the rate of etherification and more importantly increases the facility by which acid hydrolysis later cleaves the trityloxy group. Blocking the hydroxy function can also be accomplished with a trialkylsilyl group, a tetrahydropyranyl group, an α-alkoxyethyl group or any other hydroxy blocking group compatible with the conjugate addition process described below and which can later be removed by conditions to which the final products (XXIX) are stable.

Alternatively, trans-1-alkenyliodide (XXII) can be obtained from the aldehyde (XXIII) by reaction of (XXIII) with lithio acetylide and treatment of the resulting 3-hydroxy terminal acetylene (XXIV) with disiamylborane followed with trimethylamine oxide and then with iodine and sodium hydroxide solution.

Submission of the blocked vinyl iodide (XXI) to metal interchange with an alkyl lithium e.g. n-butyl lithium, at very low temperatures, e.g. −78° C., provides the vinyl lithium derivative (XXV), the trans-configuration of the double bond being retained. After one to four hours, addition of a trialkyl aluminum, e.g. trimethyl aluminum, triethylaluminum, tripropylaluminum, tri-isobutyl aluminum and the like, to the solution of the lithio derivative (XXV) furnishes the key alanate intermediate (XXVI), also with retention of the trans-configuration of the double bond. The cycloalkenone (XXVII) dissolved in ether or other non-prototropic solvent, is then added to the alanate solution. The resulting solution is allowed to warm to room temperature and is kept for about six to eighteen hours at ambient temperatures. The carboxylic acid group in cycloalkenone (XXVII) is blocked as an ester. Interaction of alanate (XXVI) with cycloalkenone (XXVII)

results in the transfer of the trans-1-alkenyl ligand in (XXVI) with retention of the trans-configuration to the cycloalkenone (XXVII) furnishing, after quenching the reaction solution, the 1,4-conjugate addition product (XXVIII). In (XXVIII) we are not certain of the relative configuration of the side-chains to each other. The situation is indicated in structure (XXVIII) by the -ω- bond between the ring and the

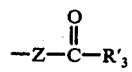

chain and is indicated in the nomenclature of the compounds involved by the designation 8ξ. In any event, deblocking to (XXIX) with acid, e.g., treatment with acetic acid:tetrahydrofuran:water in the ratio of 3:1:1 at 25°–45° C. for some three to forty-eight hours, results in the trans-relationship between the chains. This procedure also results in de-O-tritylation as well as hydrolysis of tetrahydropyranyl and trialkylsilyl groups. Alkyl esters are not cleaved by this procedure. Saponification can not be accomplished by the usual alkaline procedures; but can be effected by enzymatic or microbiological techniques.

In order to ensure a trans-relationship in (XXVIII) these products can be submitted to conditions known in the literature to equilibrate cis-8-iso $PGE_1$ to a mixture containing about 90% of the trans product. These conditions involve treatment with potassium acetate in aqueous methanol for 96 hours at room temperature.

The 13-dihydro derivative ($C_{13}$–$C_{14}$ is ethylene) of this invention can be prepared by reduction of the $\Delta^{13}$ function in the corresponding 13-prostenoic acids or esters. This reduction can be accomplished by catalytic reduction, preferably at low pressure with a noble metal catalyst in an inert solvent at ambient temperatures.

The 13-dihydro derivatives can also be prepared by treating cycloalkenones of formula (XXVII) with Grignard reagent (XXX) in the usual manner in the presence of a catalyst such as the tributylphosphine cuprous iodide complex. The 15-O-t-butyl blocking group in the conjugate addition product can be efficiently removed by treatment with neat trifluoroacetic acid in the cold for about twenty minutes followed by brief treatment with aqueous ammonia because of potential 15-O-trifluoracetylation.

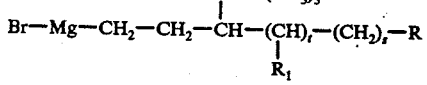

The 9-keto derivatives of this invention can be converted to the corresponding 9-hydroxy derivatives. If this conversion is effected with sodium borohydride, the product is a mixture of 9α- and 9β-hydroxy derivatives, (XXXII) and (XXXIII), respectively as set forth in the reaction scheme of Flowsheet D which follows and in which Z, R"$_3$, s, t, R, R$_7$ and $C_{13}$–$C_{14}$ are as hereinabove defined. The 9α and 9β derivatives are separable from each other by chromatographic procedures well known in the art.

When the reduction of the 9-keto function is carried out with lithium perhydro-9b-boraphenylalyl hydride [H. C. Brown and W. C. Dickason, *Journ. Amer. Chem. Soc.*, 92, 709 (1970)] or with lithium (tri-sec-butyl)-borahydride the product is at least predominantly the 9α-hydroxy derivative (XXXII), wherein the 9-hydroxy group is cis to the side-chain attached to $C_8$ and to the 11-substituent. In accordance with accepted convention, an α-substituent at the 8-, 9-, 11- or 12-positions is behind the plane of the paper whereas a β-substituent at these positions is in front of the plane of the paper. This is usually represented by a ---bond for an α-substituent, a — bond for a β-substituent, and a ∼ bond where both are indicated.

FLOWSHEET D

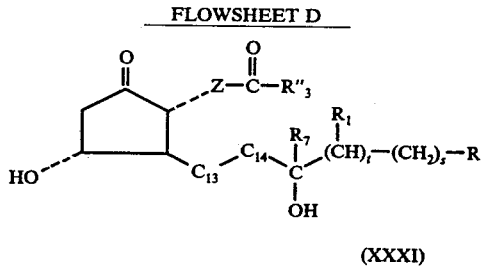

(XXXI)

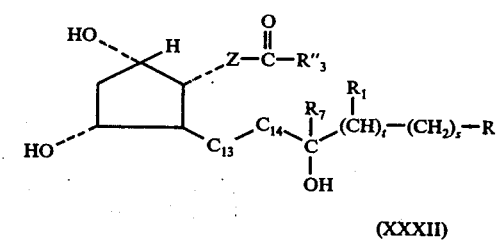

(XXXII)

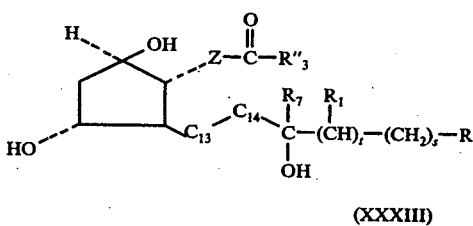

(XXXIII)

A useful procedure for the introduction of the 15-lower alkyl group (R'$_7$) is illustrated by the sequences of Flowsheet E, which follows.

FLOWSHEET E

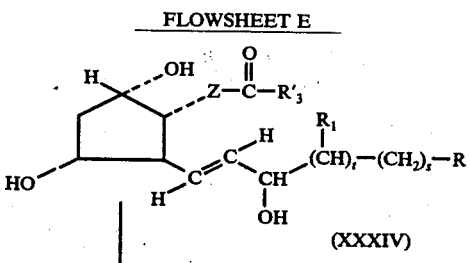

(XXXIV)

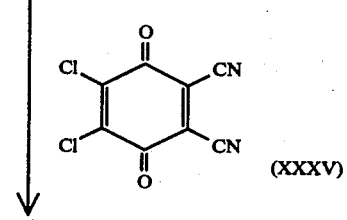

(XXXV)

-continued
FLOWSHEET E

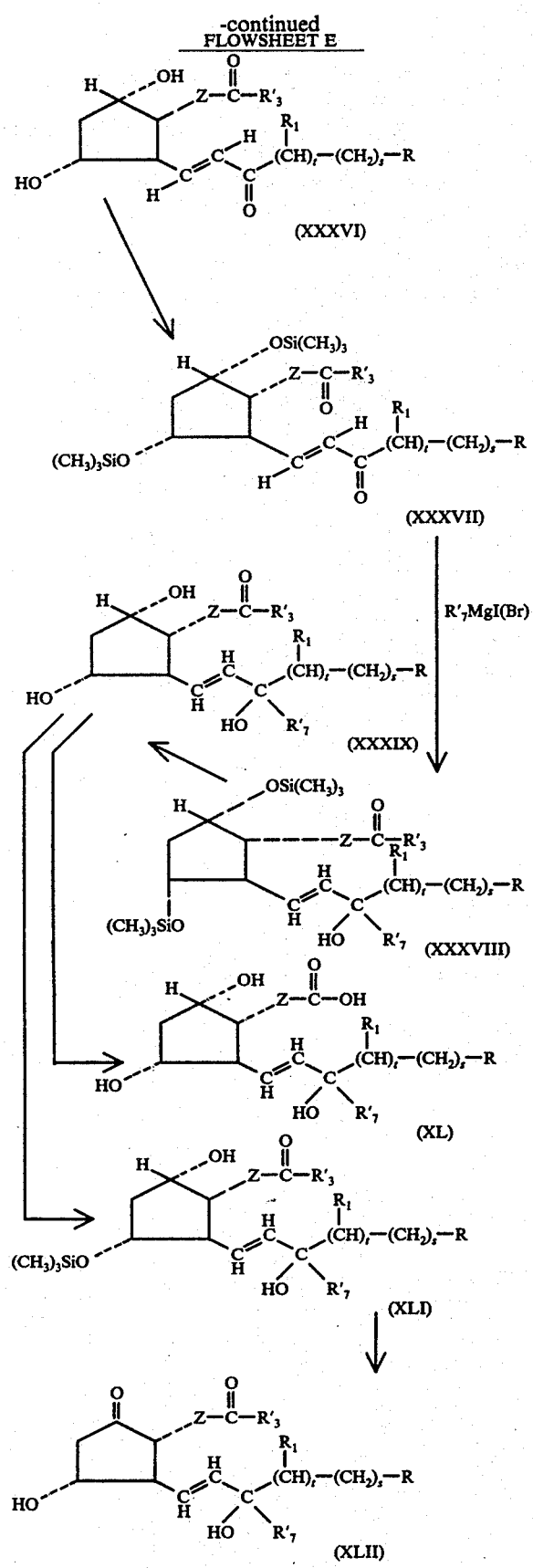

In Flowsheet E above R, $R_1$, $R'_3$, s, t and Z are as hereinabove defined, and $R'_7$ is a lower alkyl group. In the sequence depicted in Flowsheet E the 9α, 11α, 15-triol (XXXIV) is treated with 2,3-dichloro-5,6-dicyanobenzoquinone (DDQ) (XXXV), which preferentially oxidizes the allylic alcohol function at $C_{15}$ to give the 15-ketone (XXXVI). Blocking of the remaining hydroxy functions as trimethylsilyl ethers gives (XXXVII), which is reacted with the alkyl Grignard, $R'_7MgI$, to give the 15-alkyl-15-hydroxy derivative (XXXVIII). Hydrolysis of the silyl ether blocking group then furnishes the triol ester (XXXIX), saponification of which gives (XL).

Preferential blocking of the 11α-hydroxy function in trio (XXXIX) to give the 11α-trimethylsilyloxy derivative (XLI) is accomplished by treating (XXXIX) with N,N-diethyl-1,1,1-trimethylsilylamine. Oxidation of the secondary 9α-hydroxy group in (XLI) followed by de-O-silylation provides the 9-oxo-11α-hydroxy-15-alkyl derivative (XLII). This procedure leads to two epimeric $C_{15}$ alcohols and these are separable by chromatographic procedures.

When the 9-oxo-11-oxy derivative (XLIII), preferably the 11-hydroxy derivative, are treated with dilute acid it is possible to effect elimination and the formation of the corresponding $\Delta^{10}$ derivative (XLIV) (prostaglandins of the A type). A preferred procedure involves treatment in tetrahydrofuran:water (2:1) solvent 0.5 N in hydrochloric acid for about twenty hours at ambient temperatures. Under these conditions tetrahydropyranyl or trialkylsilyl esters undergo hydrolysis. More prolonged treatment with acid or preferably treatment with dilute base effects the conversion of (XLIII) or (XLIV) to the $\Delta^{8(12)}$ derivative (XLV, prostaglandins of the B type). The novel compounds of formula (XLV) are also embraced within the scope of this invention. See Flowsheet F, which follows and in which Z, R, $R_1$, $R_3$, $R''_3$, $R_8$, s, t, and $C_{13}$–$C_{14}$ are as hereinabove defined.

FLOWSHEET F

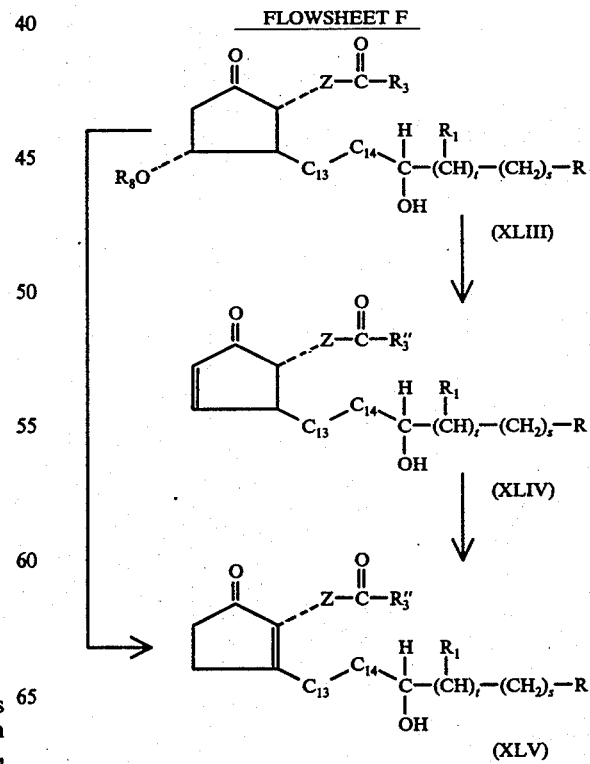

The prostanoic and prostenoic carboxylic acids of this invention are convertible to the corresponding alkyl esters by treatment with the appropriate diazoalkane in the usual manner.

The 9-oxo derivatives of this invention are convertible to the corresponding compounds A and B (see above, the third proviso noted above not applying) wherein Y is

and in which $R_{10}$ is selected from the group consisting of hydroxy, lower alkoxy, ureido, thioureido, anilino and anilino mono- or di-substitued with halogen, lower alkyl, lower alkoxy or carboxylic acid groups or a combination of such groups. The novel compounds A and B (the third proviso listed above not applying) wherein Y is

are also embraced within the purview of this invention.

All of the compounds of this invention can be isolated and purified by conventional methods. Isolation can be accomplished, for example, by dilution of the reaction mixture with water, extraction with a water-immiscible solvent such as methylene chloride, ethyl acetate, benzene, cyclohexane, ether, toluene and the like; chromatography; adsorption on ion-exchange resins, distillation, or a combination of these. Purification of the compounds of this invention can be accomplished by means known in the art for the purification of prostaglandins and lipids, fatty acids, and fatty esters. For example, liquid-liquid partition chromatography, reverse phase partition chromatography, countercurrent distribution, adsorption chromtography on Florisil ® (synthetic magnesium silicate) or silica gel, dry column chromatography, high speed liquid chromatography, preparative paper chromatography, preparative thin layer chromatography, chromatography over silver loaded cation exchange resins, and combinations thereof can be used effectively to purify the compounds produced by the processes of this invention.

The individual optical isomers of this invention can be obtained by resolution of the corresponding racemates. This can be accomplished by various methods of resolution well-known in the art. Thus, the prostenoic acids can be treated with an optically active base such as cinchonine, quinine, brucine, d- or 1-α-phenylethylamine and the like to produce diastereoisomeric salts which can be separated by crystallization. Resolution of the racemic prostaglandin-like compounds of this invention can also be accomplished by reverse phase and absorption chromatography on an optically active support and absorption chromatography on an optically active support and adsorbent or be selective transformation of one isomer with a biologically-active prostaglandin transforming system. Such transformations can be carried out by incubation or perfusion using methods well established in the art, followed by isolation and recovery of the isomer resistant to the metabolic transformation applied.

Additional procedures for effecting the resolution of the racemic products of this invention involve conversion of a 9α-hydroxy racemate (the component enantiomers are illustrated by LXVI and LXVII below) wherein the $C_{11}$ and $C_{15}$ hydroxy functions have been preferentially blocked by tetrahydropyranyl or trialkylsilyl groups, to the corresponding phthalate half acidester, deblocking the $C_{11}$ and $C_{15}$ hydroxy functions and conversion of the diacid (e.g., XLVIII) to a bis salt (e.g., IL) with an optically active amine (e.g., 1-(-)-α-methylbenzylamine, D-(+)-α-methylbenzylamine, brucine, dehydroabietylamine, strychnine, quinine, cinchonine, cinchonidine, quinidine, ephedrine, deoxyephedrine, amphetamine, (+)-2-amino-1-butanol, (-)-2-amino-1-butanol and the like). The resulting diastereoisomers are then separated by fractional crystallization and the individual components are then converted by acidification and saponification to the individual optically active parent 9α-hydroxy enantiomers (XLVI) and (XLVII), oxidation of which, after preferential blocking of the $C_{11}$ and $C_{15}$ hydroxy functions with tetrahydropyranyl or trialkylsilyl groups, provides the corresponding individual 9-oxo enantiomers (L) and (LI).

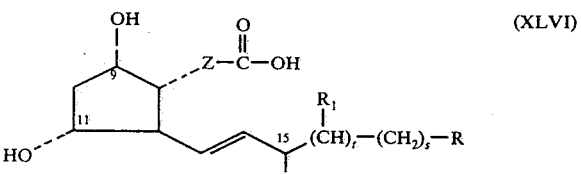

(XLVI)

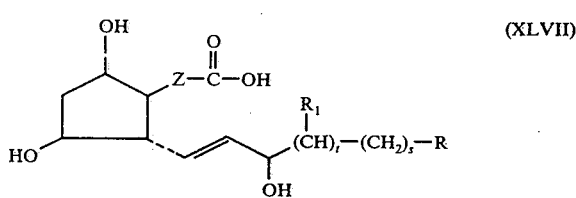

(XLVII)

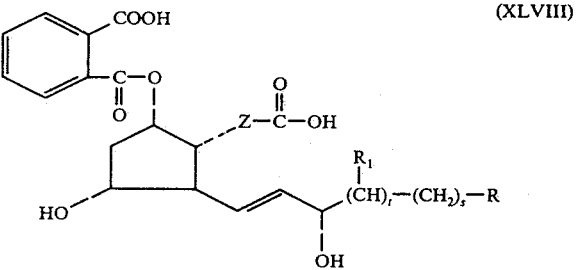

(XLVIII)

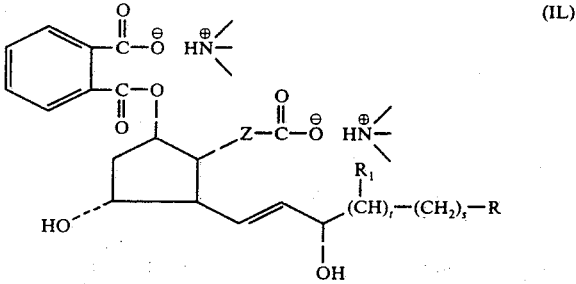

(IL)

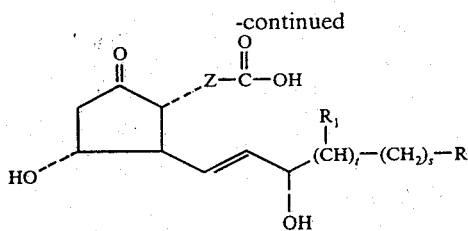

(L)

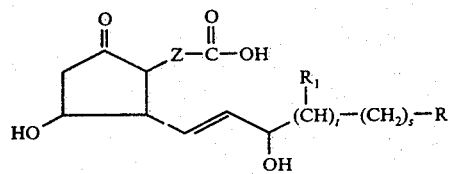

(LI)

Another procedure involves conversion of the 9α-hydroxy racemate (as the prostenoic acid ester and with the $C_{11}$ and $C_{15}$ alcohol functions preferentially blocked as tetrahydropyranyl or trialkylsilyl ethers) to the diastereoisomeric carbamates with an optically active isocyanate, e.g., (+)-1-phenylethylisocyanate or (-)-1-phenylethylisocyanate, followed by deblocking. Separation of the diastereoisomers, for example (LII) and (LIII), can be accomplished by fractional crystallization or by the usual chromatographic procedures, or if necessary by high speed liquid chromatography involving, if necessary, recycling techniques. [See G. Gallick, American Laboratory, 19–27 (August, 1973) as well as references cited therein. Addition information concerning high speed liquid chromatography and the instruments necessary for its application is available from Waters Associates Inc., Maple St., Milford, Mass.]. Base-treatment of the individual diasteromeric carbamates affords the individual enantiomeric alcohols, for example (XLVI) and (XLVII)

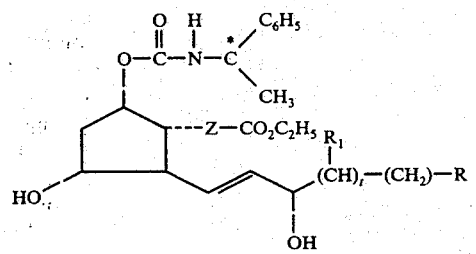

(LII)

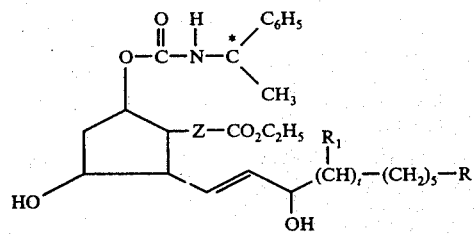

(LIII)

It is also possible to effect resolution of the 9α-hydroxy racemate, preferably as the prostenoate ester, by esterification of the 9α-hydroxy function (prior preferential blocking of $C_{11}$ and $C_{15}$ hydroxy functions as tetrahydropyranyl or trialkylislyl ethers) with an optically active acid, via its acid chloride followed by deblocking the $C_{11}$ and $C_{15}$ alcohol groups. Suitable optically active acids include ω-camphoric acid, menthoxyacetic acid, 3α-acetoxy-Δ$^5$-etianic acid, (−)-α-methoxy-α-trifluoromethylphenylacetic acid and (+)-α-methoxy-α-trifluoromethylphenylacetic acid, and the like. The resulting diastereoisomeric esters, for example (LIV) and (LV), are then separated by fractional crystallization or by chromatographic techniques including, if necessary, the use of high speed liquid chromatography. Saponification of the individual diastereoisomers then provides the individual 9α-hydroxyprostenoic acid enantiomers (XLVI) and (XLVII).

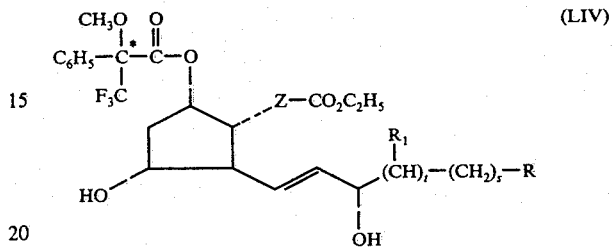

(LIV)

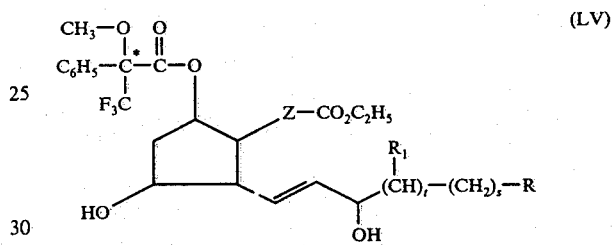

(LV)

Another resolution procedure, less useful than the methods described above based on the 9α-hydroxy derivative, involves derivatization of the keto function of the racemic 9-oxoprostenoic acid or ester (the component enantiomers of which are illustrated by L and LI) with the usual type of ketone derivatizing agents bearing an optically active center. The resulting mixture of diastereoisomeric derivatives can then be separated by fractional crystallization or by chromatography or, if necessary, by high speed liquid chromatography. The individual diastereoisomeric keto derivatives, for example, (LVI) and (LVII), are then convertable to the individual 9-oxo enantiomers (L) and (LI) by any of the usual cleavage techniques provided that they are sufficiently mild so as not to disturb the sensitive 11-hydroxy-9-keto system. Ketone reduction of the 9-oxo-enantiomer as described hereinabove then provides the corresponding 9α-hydroxy or 9β-hydroxy enantiomer (XLVI) or (XLVII). Among the optically active reagents useful for ketone derivatization are 1-α-aminoxy-γ-methylpentanoic acid hydrochloride [E. Testa et al., Helv. Chimica Acta, 47 (3), 766 (1973)], menthylhydrazine, and 4-α-methylbenzylsemicarbazide. A useful procedure for the cleavage of oximes such as (LVI) and (LVII) involves treatment of the oxime at about 60° C. for about 4 hours in 1:2 aqueous-tetrahydrofuran buffered with ammonium acetate and containing titanium trichloride.

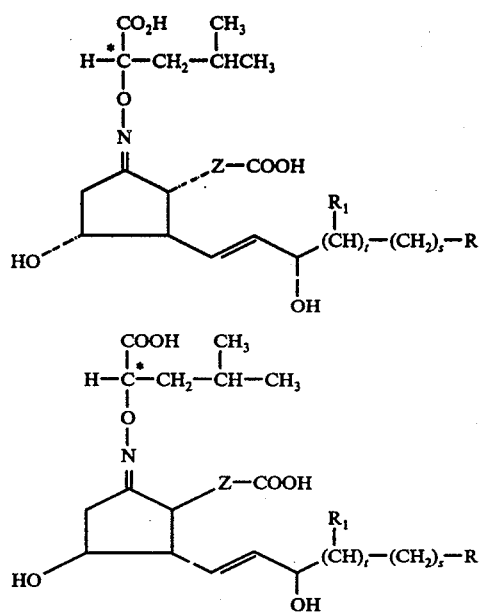

(LVI)

(LVII)

When the compounds of this invention are prepared from non-resolved starting compounds usually two racemates are obtained. In the $\Delta^{13}$-trans series these racemates can be separated from each other by careful application of the usual chromatographic procedures. In the more difficult instances it may be necessary to apply high pressure liquid chromatography including recycling techniques. Formulae (L) and (LI) above illustrate the enantiomeric components of one racemate, usually referred to as the "15-normal" racemate. Formulae (LVIII) and (LIX) below represent the enantiomeric components of the second racemate, usually referred to as the "15-epi" racemate. Separation of the enantiomeric components of the "15-epi" racemate proceeds as described above for the "15-normal" racemate, preferably via the 9α-hydroxy intermediates.

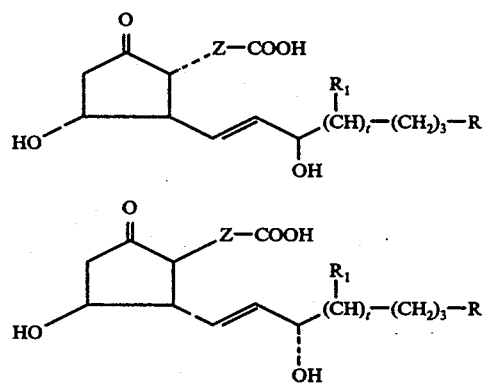

(LVIII)

(LIX)

It is also possible to prepare the individual enantiomers via the conjugate addition procedure discussed above by starting with a resolved 4-hydroxycyclopentenone (see XXVII) and a resolved β-chain precursor (see XXII).

The 4-hydroxycyclopentenone racemates may be resolved into their component enantiomers (LX) and (LXI) by derivatizing the ketone function with a reagent having an optically active center. The resulting diastereomeric mixture can then be separated by fractional crystallization, or by chromatography, or by high speed liquid chromatography involving, if necessary, recycling techniques. Among the useful optically active ketone derivatizing reagents are 1-α-aminoxy-γ-methylpentanoic acid hydrochloride (to give LXII), (R)-2-aminoxy-3,3-dimethylbutyric acid hydrochloride, methyl hydrazine and 4-α-methylbenzyl semicarbazide. After separation of the diastereomeric derivatives, reconstitution of the keto function provides the individual 4-hydroxycyclopentenone enantiomers (LX) and (LXI). A useful procedure for the resolution of a 4-hydroxycyclopentenone racemate via an oxime such as (LXII) is described in the art [R. Pappo, P. Collins and C. Jing, Tetrahedron Letters, 943 (1973)].

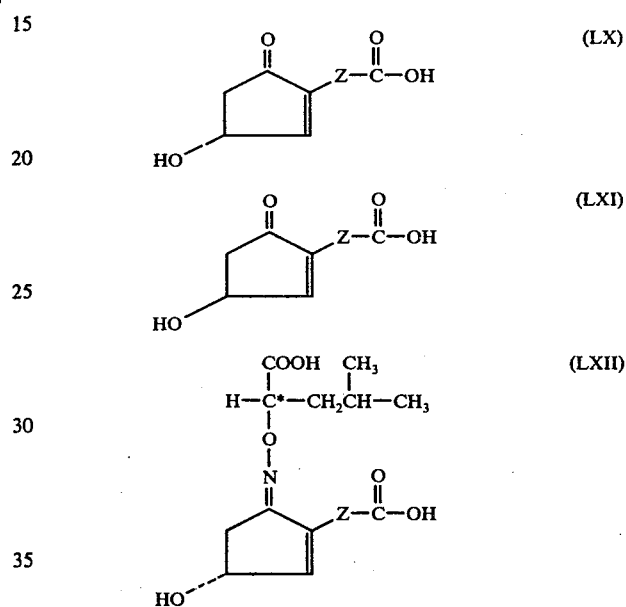

An alternative procedure for the preparation of the 4(R)-hydroxycyclopentenone enantiomers such as (LX) involves as a key step the selective microbiological or chemical reduction of trione (LXIII) to the 4(R)-hydroxycyclopentanedione (LXIV). A wide variety of microorganisms are capable of accomplishing this asymmetric reduction, one of the most useful being *Dipodascus uninicleatus*. This step also can be achieved chemically by catalytic hydrogenation in the usual manner (for example, under about one atmosphere of hydrogen in methanol) using a soluble rhodium catalyst with chiral phosphine ligans, such as (1,5-cyclooctadiene)-bis(o-anisylcyclohexylmethylphosphine)rhodium (I) tetrafluoroborate in the presence of one equivalent of organic base, such as triethylamine.

Conversion of hydroxycyclopentanedione (LXIV) to an enol ether or enol ester, wich as (LXV, E = alkyl, preferably isopropyl; aroyl such as benzoyl; or arylsulfonyl such as 2-mesitylenesulfonyl), is accomplished by treatment, for example, with isopropyl iodide and a base such as potassium carbonate in refluxing acetone for from 15 to 20 hours, or with a base such as triethylamine and 0.95 equivalents of benzoyl chloride or a slight excess of 2 mesitylenesulfonyl chloride, in a non-protropic solvent at a temperature of about $-10°$ to $=15°$ C. Reduction of (LXV) with excess sodium bis(2-methoxyethoxy)aluminum hydride in a solvent such as tetrahydrofuran or toluene at low temperatures such as $=60°$ to $-78°$ C., followed by mild acid hydrolysis (representative conditions: aqueous dilute hydrochloric acid, pH 2.5; or oxalic acid, sodium oxalate in chloroform) at ambient temperatures from 1 to 3 hours provides the (4)R-hydroxycyclopentenone ester (LXVI), which can then be saponified to (LX). The ester (LXVI), after blocking the hydroxy function as described hereinabove, can be subjected to conjugate addition reactions also as described hereinabove. The conjugate addition product, after deblocking the 11- and 15-hydroxy groups, will then be a methyl ester which can be hydrolyzed to the corresponding carboxylic acid by enzymatic or microbiological procedures, for example with baker's yeast or by exposure to *Rhizopus oryzae*.

For a description of these procedures in the art see: C. J. Sih et al., *Jour. Amer. Chem. Soc.*, 95 1676 (1973); J. B. Heather et al., *Tetrahedron Letters*, 2213 (1973); R. Pappo and P. W. Collins, *Tetrahedron Letters*, 2627 (1972) and R. Pappo, P. Collins and C. Jung, *Ann. N. Y. Acad. Sci.*, 180, 64 (1971). For a description of the baker's yeast procedure see C. J. Sih et al., *Jour. Amer. Chem. Soc.*, 94, 3643 (1972).

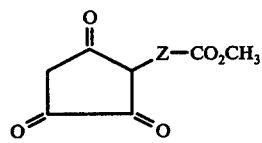

(LXIII)

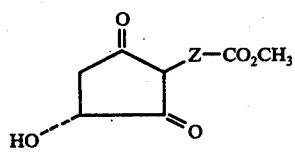

(LXIV)

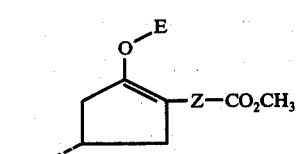

(LXV)

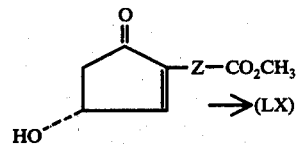

(LXVI)

→(LX)

Procedures for the preparation of the requisite cyclopentanetriones (LXIII) are well-established in the art and generally involve the treatment of an ω-1 oxo long chain ester (LXVII) with methyl or ethyl oxalate and a base such as sodium methoxide in methanol, followed by treatment with dilute hydrochloric acid in aqueous methanol to effect the dealkoxyalylation of the intermediate (LXVIII). See J. Kutsube and M. Matsui, *Agr. Biol. Chem.*, 33, 1078 (1969); P. Collins, C. J. Jung and R. Pappo, *Israel Journal of Chemistry*, 6, 839 (1968); R. Pappo, P. Collins and C. Jung, *Ann. N. Y. Acad. Sci.* 180, 64(1971); C. J. Sih et al., *Journ. Amer. Chem. Soc.*, 95, 1676 (1973) (see reference 7); and J. B. Heather et al., *Tetrahedron Letters*, 2313 (1973) for pertinent background literature.

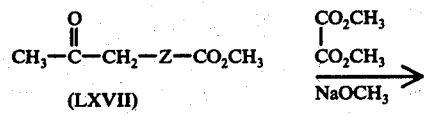

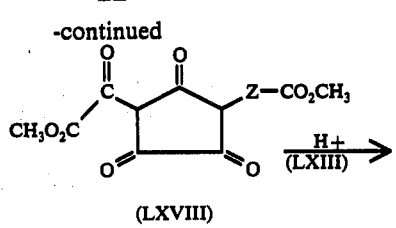

(LXVIII)

The intermediate keto esters (LXVII) may be prepared by a variety of methods known to the art. One useful procedure is outlined below and involves alkylation of ethyl acetoacetate sodium salt (LXIX) in the usual manner with the appropriate side-chain precursor (LXX, X=Cl, Br, I, Preferably Br or I) followed by decarbethoxylation and reesterification, all in the usual manner.

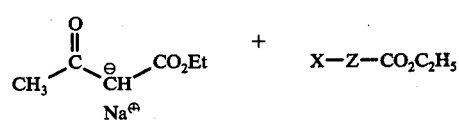

(LXIX)            (LXX)

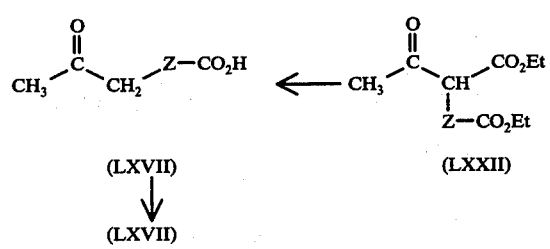

(LXVII)           (LXXII)

↓

(LXVII)

The side-chain precursors (LXX) are commercially available where Z is —(CH$_2$)$_m$—, and can be prepared as described in Belgian Patent No. 786,215 (granted and opened to inspection Jan. 15, 1973) where Z is

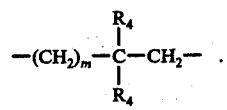

Where Z is

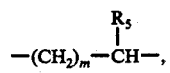

precursor (LXX) can be prepared as indicated below by mono-tetrahydropyranylation of the diol (LXXIII) to (LXXIV), followed by mesylation, treatment of the resulting mesylate (LXXVI) with the appropriate substituted sodio malonate to give (LXXV), decarbethoxylation and reesterification to (LXXVII), mesylation of the second hydroxy function to (LXXIX) and displacement with lithium bromide (or iodide) to (LXXXI). Alternatively, the ω-bromo alcohol (LXXX) after blocking as the tetrahydropyranyl derivative (LXXVIII), on treatment with the substituted sodio malonate provides (LXXV).

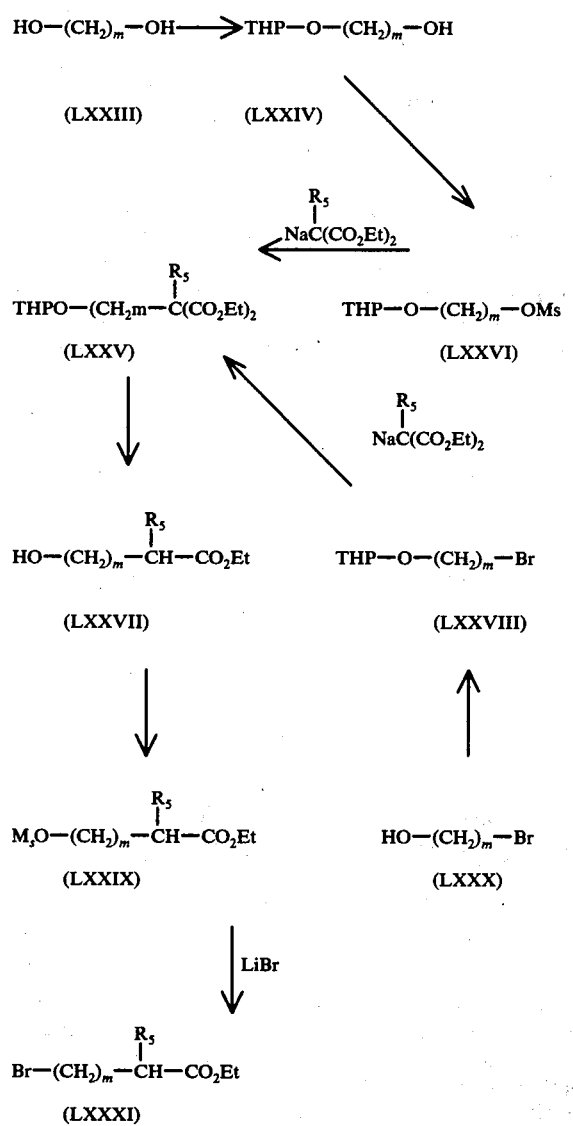

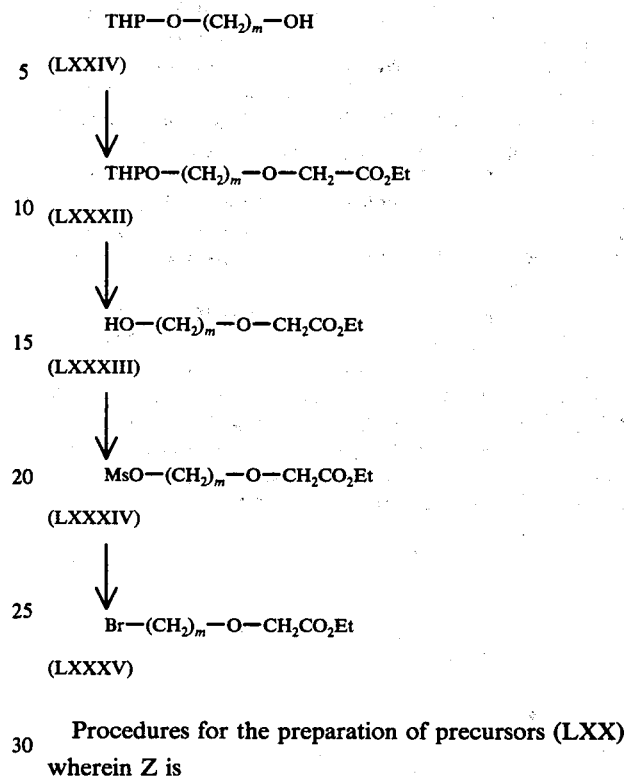

Those precursors wherein Z is —(CH$_2$)$_m$—O—CH$_2$— can be prepared by the transformations shown directly below starting with the mono-tetrahydropyranyl derivative (LXXIV). Thus, (LXXIV) is converted to the lithium alcoholate by treatment with butyl lithium, the alcoholate is then O-alkylated with ethyl bromoacetate to provide (LXXXII), which an de-tetrahydropyranylation, mesylation and reaction with lithium bromide gives the required (LXXXV). (These and all the above-described transformation can be effected in the usual manner, well-established in the art; pertinent examples for most of the reactions can be found in the above-cited Belgian Pat. No. 786,215.)

Procedures for the preparation of precursors (LXX) wherein Z is

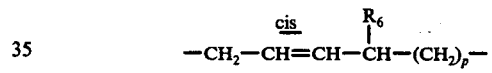

also can be found in the art [see J. B. Heather et al., *Tetrahedron Letters*, 2313 (1973)].

It is also possible to resolve the 4-hydroxycyclopentenone racemate (LXXXVI) by microbiological means. Thus, treatment of the 4-O-alkanoyl derivatives (LXXXVIII, R$_{12}$ = alkyl) of racemate (LXXXVI) (preferably the 4-O-acetyl and 4-O-propionyl derivatives) with an appropriate microorganism preferably a Saccharomyces species, e.g. 1375-143, affords preferential de-O-acylation of the 4(R)-enantiomer to give (LXXXVIII), which is then separated from the unreacted 4(S)-O-acyl enantiomer (LXXXIX) by chromatographic procedures. After separation, mild hydrolysis of the 4(S) derivative (LXXXIX) provides the 4(S)-hydroxycyclopentenone (XC). [See N. J. Marsheck and M. Miyano, *Biochimica et Biophysica Acta*, 316, 363 (1973) for related examples.]

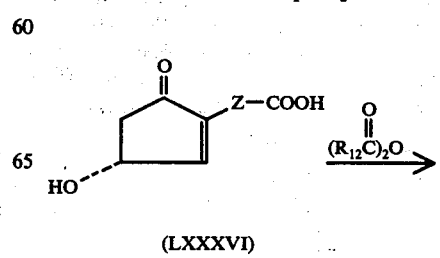

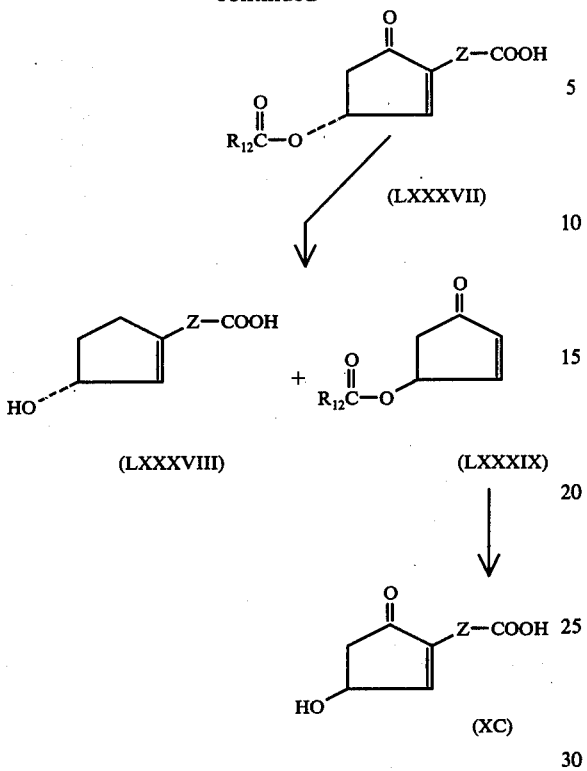

It is also possible to prepare the 4-hydroxycyclopentenones (LXXXVIII) and (XC) directly by selective microbial hydroxylations of the corresponding 4-unsubstituted cyclopentenone (XCI), for example, with *Aspergillus niger* ATCC 9142; other organisms can also accomplish this hydroxylation; for a literature example, see S. Kurozumi, T. Tora and S. Ishimoto, *Tetrahedron Letters*, 4959 (1973).

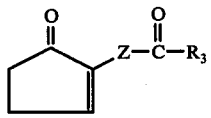

The β-chain precursors racemates can be resolved at either the acetylenic alcohol stage (XXIV, Fl. C) or the trans-vinyl iodide stage (XXII, Fl. C) by a variety of methods well-known in the art. These methods will be illustrated below with the acetylenic alcohol (XXIV), but they apply equally well to the trans-vinyl iodide (XXII). Furthermore, the resolved acetylenic alcohol (XXIV) can be converted to the trans-vinyl iodide (XXII) or its derivatives as described hereinabove without racemization [see for an example, A. F. Kluge, K. G. Untch and J. H. Fried, *Journ. Amer. Chem. Soc.*, 94, 7827 (1972)]. The more detailed discussion above concerning the use of each individual derivative type applies to these racemates as well.

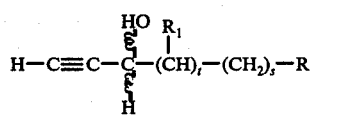

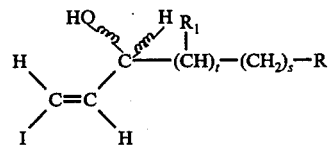

Racemates (XXIV) or (XXII) can be resolved by reverse phase and absorption chromatography on an optically active support system or by selective transformation of one isomer by microbiological or enzymatic procedures.

A more generally applicable procedure involves conversion of the racemic alcohol to a mixture of diastereomers by derivatization of the hydroxy function with an optically active reagent, followed by separation of the diastereomers by fractional crystallization or chromatographic procedures, as discussed hereinabove. Regeneration of the alcohol function from the individual diastereomer then provides the individual enantiomeric alcohols, e.g., (XVII) and (XCIII) from racemate (XXIV).

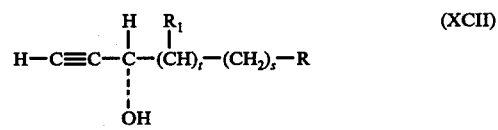

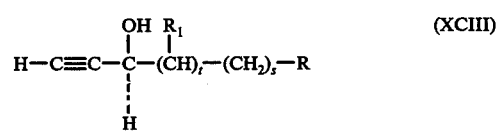

Useful derivatives for resolution puposes include the salts of the phthalate half acid ester (XCIV) with an optically active amine (e.g., 1-(−)-α-methylbenzylamine, d-(+)-α-methylbenzylamine, brucine, dehydroabietylamine, strychinine, quinine, cinchonine, cinchonidine, quinidine, ephedrine, deoxyephedrine, amphetamine, (+)-2-amino-1-butanol, (−)-2-amino-1-butanol and the like).

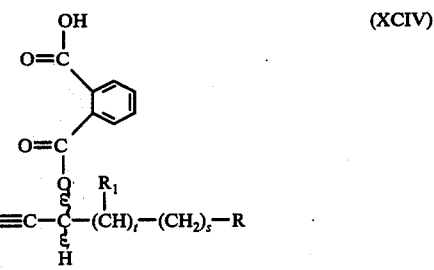

For the resolution in the art of the related 3-hydroxy-1-octyne by this procedure see J. Fried et al., *Annals of the N.Y. Acad. of Sci.*, 180, 38 (1971), and of the related 1-iodo-trans-1-octen-3-ol see A. F. Kluge, K. G. Untch and J. H. Fried, *Jour. Amer. Chem. Soc.*, 94, 7827 (1972).

Other useful derivatives are the diastereomeric carbamates (XCV) obtained by treatment of racemate (XXIV) with an optically active isocyanate (e.g., (+)-1-phenylethylisocyanate and (−)-1-phenylethylisocyanate).

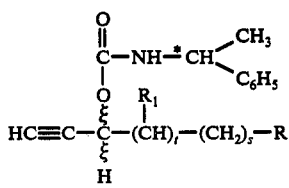

Various esters of racemate (XXIV) with optically active acids are also useful for resolution purposes. Among the optically active acids which can be used in this connection are ω-camphoric acid, menthoxyacetic acid, 3α-acetoxy-Δ⁵-etianic acid, 3α-acetoxy-5,16-etiadienoic acid, (−)-α-methoxy-α-trifluoromethylphenylacetic acid (see XCVI), (+)-α-methoxy-α-trifluoromethylphenylacetic acid, and the like.

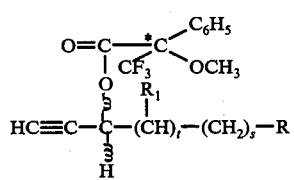

The resolution of the related 1-octyne-3-ol with 3β-acetoxy-Δ⁵-etianic acid and 3β-acetoxy-5,16-etiadienic acid has been described in the art [see R. Pappo, P. Collins, and C. Jung, *Annals of the N.Y. Acad. of Sci.,* 180, 64 (1971)].

The preparation of the enantiomeric acetylenic alcohols or 3-hydroxy-trans-vinyl iodides can also be accomplished by microbial techniques, involving a selective de-esterification of 3-O-alkanoyl or aroyl derivatives (XCVII) followed by chromatographic separation to the individual enantiomers and hydrolysis of the non de-esterified ester.

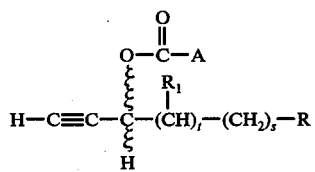

Alternatively, it is possible to effect selective microbial reduction of the corresponding 3-keto derivatives (XCVIII) and (IC) to a single enantiomer. Microbial reduction is preferably carried out in the trans-vinyl iodide series (IC); useful microorganisms for this purpose are *Penicillium decumbens* and *Aspergillus ustus.* The preparation of ketone (XCVIII) is described hereinabove [see XX, Flowsheet C]. Ketones (XCVIII) and (IC) are also

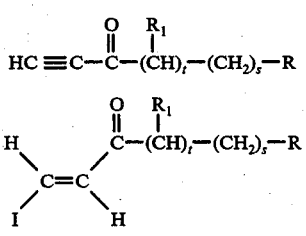

readily obtainable by oxidation under mild conditions of the corresponding alcohols. For pertinent literature examples see J. B. Heather et al., *Tetrahedron Letters,* 2313 (1973). It is also possible to effect optically selective reduction of ketones (XCVIII) or (IC) by the use of an optically active reducing agent such as tri(+S-2-methylbutyl)aluminum etherate, lithium aluminum hydride-3-O-benzyl-1,2-O-cyclohexylidene-α-D-glucofuranose complex, and lithium hydrodipinan-3α-ylborate. For pertinent references to this procedure see R. A. Kretchmer, *Journ. Org. Chem.* 37, 801 (1972); S. A. Landor et al., *Journ. Chem. Soc.* (C) 1822, 2280 (1966), ibid. 197 (1967); M. F. Grundon et al., ibid., 2557 (1971); and J. D. Morrison and H. S. Mosher, "Assymetric Organic Reactions", pp. 160–218, Prentice-Hall, Englewood Cliffs, N.J. (1971).

It is to be noted that use of only one resolved precursor, either the β-chain or the 4-hydroxycyclopentenone, in the conjugate addition process will lead to the formation of two diastereomers, which, in the Δ¹³ series at least, can then be separated by chromatographic and other procedures (as described above for the corresponding racemate) into the individual component enantiomers.

It is also possible to introduce the 15-normal (in distinction to 15-epi) hydroxy function by stereoselective reduction of 15-keto intermediates such as (XXXVI) or (XXXXVII) of Flowsheet E with reagents such as lithium hexyltetrahydrolimonyl borohydride. For maximum selectivity it is best to block the 11-hydroxy function in (XXXVI) with bulky groups such as p-phenylbenzoyl or p-phenylcarbamoyl. These groups can later be saponified prior to oxidation of the 9-hydroxy function. Alternative borohydride reagents include lithium hexyl-di-sec-butylborohydride and lithium tri-sec-butylborohydride. For examples and further discussion of this procedure see Corey et al., *J.A.C.S.,* 94, 8616 (1972); Corey et al., ibid., 93, 1491 (1971); and Miyano et al., *Chim. Communications,* 180 (1973).

The novel compounds of the present invention have potential utility as hypotensive agents, anti-ulcer agents, agents for the treatment of gastric hypersecretion and gasteric erosion, bronchodilators, abortifacients, agents for the induction of labor, agents for the induction of menses, fertility-controlling agents, central nervous system regulatory agents, salt and water-retention regulatory agents, diuretics, fat metabolic regulatory agents, serum-cholesterol lowering agents, anti-inflammatory agents and as agents for the inhibition of platelet aggregation. Certain of the novel compounds of this invention possess utility as intermediates for the preparation of other of the novel compounds of this invention. The compounds of this invention provide protection against the ulcerogenic properties of indomethacin. A measure of this utility which also measures potential anti-ulcer properties is the assay which follows.

Rats were starved for 48 hours (water was given ad libitum). Indomethacin (20 mg./kg. of body weight) was administered by the subcutaneous route and one-half the dose of the test compound was administered by gavage at the same time. After three hours, the second half of the test compound was administered also by gavage. Five hours after the administration of indomethacin the animals were decapitated and the stomachs removed. The stomachs were washed with distilled water, blotted on gauze, cut along the larger curvature, and the contents rinsed with distilled water. The stomachs were spread out, pinned on a cork and visualized under magnifying glass for ulcers. The criteria for scoring of ulcers was as previously reported. [Abdel- Galil et al., *Brit. J. Pharmac. Chemotherapy* 33:1–14 (1968)].

SCORE

0 — Normal
1 — Petechial hemorrhage or pin point ulcer
2 — 1 or 2 small ulcers
3 — Many ulcers, a few large
4 — Many ulcers, mainly large Control animals treated with indomethacin but not tested compound consistently give scores of about 3.0. Control animlas treated with neither indomethacin nor test compound give scores of about 0.5–0.8. The results obtained in this assay with typical compounds of the present invention are set forth in Table A below. Compounds producing a lowering of the control score by 0.5 or more are considered to be active.

TABLE A

| Compound | Total Oral dose; mg./kg. of body weight | Score Treated | Control |
|---|---|---|---|
| d,l 9-oxo-11α,15-dihydroxy-17,20-methano-13-trans-prostenoic acid | 6.25 | 1.5 | 3.0 |
| d,l 9-oxo-11α,15-epi-dihydroxy-17,20-methano-13-trans-prostenoic acid | 6.25 | 2.3 | 3.0 |

Bronchodilator activity was determined in guinea pigs against bronchospasms elicited by intravenous injections of 5-hydroxytryptamine, histamine or acetylcholine by the Konzett procedure. [See J. Lulling, P. Lievens, F. El Sayed and J. Prignot, *Arzneimittel-Forschung*, 18, 995 (1968)].

In the Table which follows bronchodilator activity for representative compounds of this invention against one or more of three spasmogenic agents is expressed as an $ED_{50}$ determined from the results obtained with three logarithemic cumulative intravenous doses.

TABLE B

| Brochodilator Activity | (Konzett Assays) $ED_{50}$ mg./kg. Spasmogenic Agent | | |
|---|---|---|---|
| Compound | 5-hydroxy-tryptamine | histamine | acetyl choline |
| d,1-9-oxo-11α-15-dihydroxy-17,20-methano-13-trans-prostenoic acid | $1.8 \times 10^{-3}$ | $.444 \times 10^{-3}$ | $1.3 \times 10^{-3}$ |
| d,1-9-oxo-11α-15-epi-dihydroxy-17,20-methano-13-trans-prostenoic acid | .228 | $42.0 \times 10^{-3}$ | 73.2 |
| d,1-9-oxo-15-hydroxy-17,20-methano-10,13-trans-prostadienoic acid | $54.6 \times 10^{-3}$ | $41.0 \times 10^{-3}$ | $292 \times 10^{-3}$ |

The novel compounds of the present invention are useful as hypotensive agents in their prostaglandin-like hypotensive activity may be demonstrated in the following test procedure. This procedure is a modification of the technique described by Pike et al., *Prostaglandins, Nobel Symposium* 2, Stockholm, June, 1966; p. 165.

Male Wistar strain rats (Royal Hart Farms) averaging approximately 250 grams in weight are fastered to rat boards in a supine position by means of canvas vests and limb ties. The femoral area is infiltrated subcutaneously with lidocaine and the iliac artery and vein are exposed and cannulated. Arterial blood pressure (systolic/diastolic) is recorded using a Statham $P_{23}$ Db pressure gauge. THe animals are anethetized before use with pentobarbital, 30 mg./kg. of body weight intravenously, and also are given hexamethonium bitartrate, 2mg./kg. of body weight intravenously. The test compounds are prepared by ultrasonic dispersion in a Saline-Tween 80 ® vehicle. A constant intravenous dose volume of 0.5 ml. is administered and test doses can range from 0.02 to 10.0 mg./kg. of body weight.

EXAMPLE 1

Preparation of 2-(6-carboxy-6-fluorohexyl)cyclopent-2-en-1-one

This cyclopentenone is prepared by the procedure described in Belgium patent no. 786,215 (January 15, 1973) for the preparation of 2-(6-carboxyoctyl)cyclopent-2-en-1-one by substituting diethyl fluoromalonate for diethyl ethylmalonate.

EXAMPLE 2

Preparation of 2-(6-carboxy-6-phenylhexyl)cyclopent-2-en-1-one

This cyclopentenone is prepared by the procedure described in Belgium Pat. No. 786,215 (Jan. 15, 1973) for the preparation of 2-(6-carboxyoctyl)cyclopent-2-en-1-one by substituting diethyl phenylmalonate for diethyl ethylmalonate.

EXAMPLE 3

Preparation of 2-(6-carboxyheptyl)cyclopent-2-en-1-one

This cyclopentenone is prepared by the procedure described in Belgium patent no. 786,215 (Jan. 15, 1973) for the preparation of 2-(6-carboxyheptyl)cyclopent-2-en-1-one by substituting diethyl methyl malonate for diethyl ethylmalonate.

EXAMPLE 4

Preparation of 2-(6-carbo-n-butoxyhexyl)cyclopent-2-en-1-one

A solution of 50 g. of 2-(6-carboxyhexyl)cyclopent-2-en-1-one [Bagli et al., *Tetrahedron Letters*, No. 5, 485 (1966)] in 1400 ml. of n-butanol containing 2.7 g. of p-toluenesulfonic acid monohydrate is allowed to stand at room temperature in a stoppered flask for about 24 hours. The solution is taken to dryness. The residue is taken up in ether and the ethereal solution is washed several times with saline solution, dried with anhydrous magnesium sulfate, and taken to dryness to afford the subject butyl ester.

EXAMPLES 5–7

Treatment of 2-(6-carboxyhexyl)cyclopent-2-en-1-one by the procedure of Example 4 with the appropriate alcohol affords the esters of the following table.

TABLE 4

| Example | Alcohol | Product Ester |
|---|---|---|
| 5 | isopropanol | 2-(6-carboisopropoxy-hexyl)cyclopent-2-en-1-one |
| 6 | methanol | 2-(6-carbomethoxyhexyl)-cyclopent-2-en-1-one |
| 7 | 1-hydroxy-n-decane | 2-(6-carbo-n-decyloxy-hexyl)cyclopent-2-en- |

TABLE 4-continued

| Example | Alcohol | Product Ester |
|---|---|---|
| | | 1-one |

EXAMPLE 8

Preparation of
4-bromo-2-(6-carboxyhexyl)cyclopent-2-en-1-one

A stirred mixture of 35.9 g. (0.171 moles) of 2-(6-carboxyhexyl)cyclopent-2-en-1-one [Bagli et al., Tetrahedron Letters, No. 5, 465 (1966)], 35.0 g. (0.197 moles) of N-bromosuccinimide, and 600 ml. of carbon tetrachloride is refluxed for 35 minutes. The mixture is cooled to 5° C. and filtered. The filtrate is washed with cold water, dried over magnesium sulfate, and taken to dryness to give an oil, $\lambda_{max.}^{MeOH} = 225$ m$\mu$(8850); $\theta$ max. = 1705 (carbonyl groups and 1625 cm$^{-1}$ (olefin group).

EXAMPLES 9-24

In the manner of the preceding Example 8, the various cyclopentenones of Table I, which follows, are converted to the corresponding 4-bromo derivatives.

TABLE 1

| Example | Starting cyclopent-2-en-1-one | Product 4-Bromocyclopentenones |
|---|---|---|
| 9 | 2-(6-carbethoxyhexyl)-cyclopent-2-en-1-one* | 4-bromo-2-(6-carbethoxyhexyl)-cyclopent-2-en-1-one |
| 10 | 2-(6-carbomethoxyhexyl)cyclopent-2-en-1-one (Example 6) | 4-bromo-2-(6-carbomethoxyhexyl)cyclopent-2-en-1-one |
| 11 | 2-(4-carboxybutyl)cyclopent-2-en-1-one* | 4-bromo-2-(4-carboxybutyl)cyclopent-2-en-1-one |
| 12 | 2-(3-carboxypropyl)cyclopent-2-en-1-one* | 4-bromo-2-(3-carboxypropyl)cyclopent-2-en-1-one |
| 13 | 2-(8-carboxyoctyl)cyclopent-2-en-1-one* | 4-bromo-2-(8-carboxyoctyl)cyclopent-2-en-1-one |
| 14 | 2-(6-carboxyoctyl)cyclopent-2-en-1-one* | 4-bromo-2-(6-carboxyoctyl)cyclopent-2-en-1-one |
| 15 | 2-(6-carboxy-5,5-dimethylhexyl)cyclopent-2-en-1-one* | 4-bromo-2-(6-carboxy-5,5-dimethylhexyl)-cyclopent-2-en-1-one |
| 16 | 2-(6-carboxy-5-oxahexyl)cyclopent-2-en-1-one* | 4-bromo-2-(6-carboxy-5-oxahexyl)cyclopent-2-en-1-one |
| 17 | 2-(6-carboxy-6-fluorohexyl)-cyclopent-2-en-1-one (Example 1) | 4-bromo-2-(6-carboxy-6-fluorohexyl)cyclopent-2-en-1-one |
| 18 | 2-(5-carboxypentyl)cyclopent-2-en-1-one* | 4-bromo-2-(5-carboxypentyl)cyclopent-2-en-1-one |
| 19 | 2-(7-carboxyheptyl)cyclopent-2-en-1-one* | 4-bromo-2-(7-carboxyheptyl)cyclopent-2-en-1-one |
| 20 | 2-(6-carboxy-6-pentylhexyl)-cyclopent-2-en-1-one (Ex. 2) | 4-bromo-2-(6-carboxy-6-phenylhexyl)cyclopent-2-en-1-one |

EXAMPLE 25

Preparation of
4-hydroxy-2-(8-carboxyoctyl)cyclopent-2-en-1-one

To a stirred solution of 57.2 g. of crude 4-bromo-2-(8-carboxyoctyl)cyclopent-2-en-1-one (Example 13) in 500 ml. of acetone and 325 ml. of water at 3° C. is added 44.1 g. (0.226 moles) of silver fluoborate during a 15-minute period. The mixture is stirred at 0°-3° C. for 2 hours and filtered. The filtrate is diluted with water, saturated with solid sodium chloride, and extracted with ether. The extract is washed with saturated sodium chloride solution, dried over magnesium sulfate, and concentrated. Partition chromatography of the residue on Celite gives white crystals, m.p. 58°-66° C., $\lambda_{max.}^{MeOH} = $ 223 m$\mu$ (7800); $\theta$max (KBr) = 3340 (hydroxyl groups), 1705 (carbonyl groups), and 1625$^{-1}$ (olefin group).

EXAMPLE 26

Preparation of
4-acetoxy-2-(6-carbethoxyhexyl)cyclopent-2-en-1-one

A mixture of 51.6 g. (0.137 moles) of crude 4-bromo-2-(6-carbethoxyhexyl)cyclopent-2-en-1-one (Example 9), 27 g. (0.162 moles) of silver acetate, and 200 ml. of glacial acetic acid is stirred at reflux for 4.5 hours. The mixture is cooled, and solids are removed by filtration. The filtrate is concentrated and extracted with hot hexane. The extract is washed with saturated sodium bicarbonate solution and saturated sodium chloride solution, dried over magnesium sulfate, and concentrated to give an oil. The crude product is distilled at reduced pressure to give a liquid, b.p. 152°-163° C. (0.01 mm); $\lambda_{max.}^{MeOH}$ = 223 m$\mu$ (10700); $\theta$max. = 1745 (ester carbonyl groups), 1725 (ketone carbonyl groups), and 1235 cm$^{-1}$ (acetoxy group).

EXAMPLE 27

Preparation of
4-hydroxy-2-(6-carboxyhexyl)cyclopent-2-en-1-one

To a stirred solution of 6.91 g. (50 mmoles) of potassium carbonate in 1400 ml. of methanol and 1400 ml. of water containing 100 mg. of hydroquinone is added 14.9 g. (50 mmoles) of 4-acetoxy-2-(6-carbethoxyhexyl)cyclopent-2-en-1-one (Example 26) during one minute at room temperature under nitrogen. The solution is stirred for 90 minutes and at this stage it contains 4-hydroxy-2-(6-carbethoxyhexyl)-cyclopent-2-en-1-one.
It is then treated with 23.6 g. (75 mmoles) of barium hydroxide octahydrate during one minute. The mixture is stirred for 60 minutes and then is concentrated at reduced pressure to a volume of 1800 ml. during one hour. The solution is diluted with 300 ml. of water, saturated with sodium chloride, and stirred with 400 ml. of ether while 70 ml. of 4N hydrochloric acid is added. The aqueous phase is extracted with additional ether, and the combined organic phases are washed with saturated sodium chloride solution. The extract is dried over magnesium sulfate. The crude product obtained after evaporation of the solvents is purified by chromatography on silica gel to give an oil, $\lambda_{max.}^{MeOH} = 223$ m$\mu$ (7360); $\theta$max. = 3380 (hydroxy groups), 1710 (carbonyl groups), and 1632 cm$^{-1}$ (olefin group).

EXAMPLE 28

Preparation of
2-(6-carboxyhexyl)-4-hydroxy-cyclopent-2-en-1-one

To a stirred solution of 10.6 g. (ca. 34 mmoles) of crude 4-bromo-2-(6-carboxyhexyl)cyclopent-2-en-1-one (Example 8) in 100 ml. of acetone and 65 ml. of water is added 8.0 g (45.2 mmoles) of silver fluoborate during 2 minutes. The temperature is maintained at 25°-30° C. by external cooling. The mixture is stirred for 90 minutes, filtered, saturated with sodium chloride and extracted with half saturated sodium bicarbonate solution. The basic extract is reacidified with dilute hydrochloric acid, saturated with sodium chloride, and extracted with ether. The extract is washed with water and saturated sodium chloride solution, dried over magnesium sulfate, and concentrated. The crude product is purified by partition chromatography on Celite to give an oil with the properties described in Example 27.

EXAMPLES 29-43

By the procedure of the preceding Example 28 the various 4-bromocyclopentenones of the following Table 2 are solvolyzed in acetone-water in the presence of silver fluoborate to provide the 4-hydroxycylopentenones of the Table. In the instance of the carboxylic acid esters the sodium bicarbonate extraction step is omitted.

TABLE 2

| Example | Starting cyclopentenones of Example | Product 4-hydoxycyclopente-2-en-ones |
|---|---|---|
| 29 | 9 | 4-hydroxy-2-(6-carbethoxyhexyl)cyclopent-2-en-1-one |
| 30 | 10 | 4-hydroxy-2-(6-carbomethoxyhexyl)cyclopent-2-en-1-one |
| 31 | 11 | 4-hydroxy-2-(4-carboxybutyl)cyclopent-2-en-1-one |
| 32 | 12 | 4-hydroxy-2-(3-carboxypropyl)cyclopent-2-en-1-one |
| 33 | 14 | 4-hydroxy-2-(6-carboxyoctyl)-cyclopent-2-en-1-one |
| 34 | 15 | 4-hydroxy-2-(6-carboxy-5,5-dimethylhexyl)-cyclopent-2-en-1-one |
| 35 | 16 | 4-hydroxy-2-(6-carboxy-5-oxahexyl)cyclopent-2-en-1-one |
| 36 | 17 | 4-hydroxy-2-(6-carboxy-6-fluorohexyl)-cyclopent-2-en-1-one |
| 37 | 18 | 4-hydroxy-2-(5-carboxypentyl)cyclopent-2-en-1-one |
| 38 | 19 | 4-hydroxy-2-(7-carboxyheptyl)cyclopent-2-en-1-one |
| 39 | 20 | 4-hydroxy-2-(6-carboxy-6-phenylhexyl)cyclopent-2-en-1-one |
| 40 | 21 | 4-hydroxy-2-(6-carbo-n-butoxyhexyl)cyclopent-2-en-1-one |
| 41 | 22 | 4-hydroxy-2-(6-carbo-isopropoxyhexyl)cyclopent-2-en-1-one |
| 42 | 23 | 4-hydroxy-2-(6-carbo-n-decyloxyhexyl)cyclopent-2-en-1-one |
| 43 | 24 | 4-hydroxy-2-(6-carboxyheptyl)cyclopent-2-en-1-one |

EXAMPLE 44

Preparation of 4-tetrahydropyranyloxy-2-(6-tetrahydropyranylcarboxyhexyl)cyclopent-2-en-1-one To a stirred solution of 5.59 g. (24.6 mmoles) of 4-hydroxy-2-(6-carboxyhexyl)cyclopent-2-en-1-one (Example 28) and 20.7 g. (246 mmoles) of dihydropyran in 100 ml. of methylene chloride at 20° C. is added 47 mg. (0.246 mmoles) of p-toluenesulfonic acid monohydrate in one portion. The temperature is maintained at 20°-25° C. by cooling and is stirred for one hour at that temperature. The solution is diluted with 200 ml. of ether and poured into a mixture of 40 ml. of saturated sodium bicarbonate solution, 40 ml. of saturated sodium chloride solution, and 80 ml. of water. The phases are separated and the aqueous phase is extracted with additional ether. The total extract is washed successively with water and saturated sodium chloride solution, dried over potassium carbonate, and freed of volatile matter by concentration at reduced pressure to give an oil, $\lambda_{max.}^{MeOH} = 223$ m$\mu$ (9500); $\theta$max. 1730 (ester carbonyl group), 1705 (ketone carbonyl group), and $1030^{-1}$ (tetrahydropyranyloxy groups).

EXAMPLES 45-55

By the procedure of Example 44, the various 4-hydroxycyclopentenones of Table 3, which follows, are converted to the tetrahydropyranyl 4-tetrahydropyranyloxycyclopentenone esters of the table.

TABLE 3

| Example | Starting 4-hydroxycyclopentenone of Example | Product Tetrahydropyran-2'-yl 4-tetrahydropyran-2'-yloxycyclopent-2-en-1-one |
|---|---|---|
| 45 | 31 | 4-tetrahydropyran-2'-yloxy-2-(4-carbotetrahydropyran-2'-yloxybutyl)cyclopent-2-en-1-one |
| 46 | 32 | 4-tetrahydropyran-2'-yloxy-2-(3-carbotetrahydropyran-2'-yloxypropyl)cyclopent-2-en-1-one |
| 47 | 25 | 4-tetrahydropyran-2'-yloxy-2-(8-carbotetrahydropyran-2'-yloxyoctyl)cyclopent-2-en-1-one |
| 48 | 33 | 4-tetrahydropyran-2'-yloxy-2-(6-carbotetrahydropyran-2'-yloxyoctyl)cyclopent-2-en-1-one |
| 49 | 34 | 4-tetrahydropyran-2'-yloxy-2-(6-carbotetrahydropyran-2'-yloxy-5,5-dimethylhexyl)cyclopent-2-en-1-one |
| 50 | 35 | 4-tetrahydropyran-2'-yloxy-2-(6-carrbotetrahydropyran-2'-yloxy-5-oxahexyl)cyclopent-2-3n-1-one |
| 51 | 36 | 4-tetrahydropyran-2'-yloxy-2-(6-carbotetrahydropyran-2'-yloxy-6-fluorohexyl)cyclopent-2-en-1-one |
| 52 | 37 | 4-tetrahydropyran-2'-yloxy-2-(5-carbotetrahydropyran-2'-yloxypentyl)cyclopent-2-en-1-one |
| 53 | 38 | 4-tetrahydropyran-2'-yloxy-2-(7-carbotetrahydropyran-2'-yloxyheptyl)cyclopent-2-en-1-one |
| 54 | 39 | 4-tetrahydropyran-2'-yloxy-2-(6-carbotetrahydropyran-2'-yloxy-6-phenylhexyl)-cyclopent-2-en-1-one |
| 55 | 43 | 4-tetrahydropyran-2'-yloxy-2-(6-carbotetrahydropyran-2'-yloxyheptyl)-cyclopent-2-en-1-one |

EXAMPLE 56

Preparation of 4-tetrahydropyranyloxy-2-(6-carbethoxyhexyl)cyclopent-2-en-1-one

To a stirred solution of 674 mg. (2.64 mmoles) of 4-hydroxy-2-(6-carbethoxyhexyl)cyclopent-2-en-1-one (Example 29) and 2.22 g. (26.4 mmoles) of dihydropyran in 2.6 ml. of methylene chloride is added 5.0 mg.

(0.026 mmoles) of p-toluenesulonic acid monohydrate. After stirring for 20 minutes at room temperature the solution is diluted with ether and poured into saturated sodium chloride solution containing a little sodium bicarbonate. The organic phase is separated and washed with saturated sodium chloride solution. The extract is dried over magnesium sulfate, and volatile matter is evaporated at reduced pressure to give an oil, $\lambda_{max}^{MeOH}$ = 224 mμ (7950); θmax. = 1735 (ester carbonyl group), 1710 (ketone carbonyl group), and 1030 cm$^{-1}$ (tetrahydropyranyloxy group).

EXAMPLES 57-60

In the manner of Example 56 the alkyl 4-hydroxycyclopentenone esters of Table 4, which follows, are converted to the corresponding 4-tetrahydropyranyloxy alkyl esters of the table.

TABLE 4

| Example | Starting 4-hydroxycyclopentenone Esters of Example | Product 4-tetrahydropyran-2'-yloxycyclopent-2-en-1-one esters |
|---|---|---|
| 57 | 30 | 4-tetrahydropyran-2'-yloxy-2-(6-carbomethoxyhexyl)-cyclopent-2-end-1-one |
| 57a | 2-(6-carbomethoxyhexyl)-4(R)-hydroxycyclopent-2-en-1-one (Ref. 1 & 2) | 4(R)-tetrahydropyran-2'-yloxy-2-(6-carbomethoxyhexyl)-cyclopent-2-en-1-one |
| 57b | 2-(6-carbomethoxyhexyl)-4(S)-hydroxycyclopent-2-en:1:one (Ref. 1) | 4(S)-tetrahydropyran-2'-yloxy-2-(6-carbomethoxyhexyl)-cyclopent-2-en-1-one |
| 58 | 40 | 4-tetrahydropyran-2'-yloxy-2-(6-carbo-n-butoxyhexyl)-cyclopent-2-en-1-one |
| 59 | 41 | 4-tetrahydropyran-2'-yloxy-2-(6-carbo-isopropoxyhexyl)-cyclopent-2-en-1-one |
| 60 | 42 | 4-tetrahydropyran-2'-yloxy-2-(6-carbo-n-decyloxyhexyl)-cyclopent-2-end-1-one |

Ref. 1 R. Pappo, P. Collins and C. Jung, Tetrahedron Letters, 943 (1973).
Ref. 2 C.J. Sih, et al., Jour. Amer. Chem. Soc., 95, 1676 (1973).

EXAMPLE 61

Preparation of all cis-2-(6-carboxy-2-cis-hexenyl)-3,4-oxidocyclopentanol

A solution of 1.42 g. (10.0 moles) of all-cis-5-hydroxy-2,3-oxidocyclopentylacetaldehyde-γ-lactol (E. J. Corey and R. Noyori, *Tetrahedron Letters*, 1970, 211) in 5 ml. of DMSO is added to a stirred solution of the Wittig reagent [E. J. Corey et al., JACS, 91, 5675 (1969)] prepared from 13.3 g. (30 moles) of 4-carboxybutyltriphenylphosphonium bromide (Example 68) 2.52 g. (.60 moles) of 57% sodium hydride dispersion, and 70 ml. of DMSO at 16° C. during 1 minute.

The solution is stirred at ambient temperature for 20 hours and poured into a stirred mixture of methylene chloride, ice, and hydrochloric acid. The organic phase is separated, and the aqueous phase is extracted with methylene chloride, saturated with sodium chloride, and extracted with ether. The combined organic extracts are partitioned with sodium bicarbonate. The aqueous basic extract is acidified with dilute HCl, saturated with sodium chloride, and extracted with ethyl acetate. The extract is washed with brine, dried over magnesium sulfate, and concentrated to give the crude title compound as an orange oil.

EXAMPLE 62

Preparation of all-cis-2-(6-carboxy-2-cis-hexenyl)-3,4-oxidocyclopentanone

To a stirred solution of ca 1.6 moles of crude all-cis-2-(6-carboxy-2-cis-hexenyl)-3,4-oxidocyclopentanol (Example 61) in 1.6 ml. of ether is added 1.6 mol. of 4.0 N chromic acid in 4N sulfuric acid at 0° C. during 9 minutes. After stirring for 5 minutes at 0° C. the solution is diluted with brine, ether, and ethyl acetate. The organic phase is treated with isopropanol, washed with brine and dried over magnesium sulfate. Evaporation of the solvent gives the subject compound as an oil.

EXAMPLE 63

Preparation of 2-(6-carboxy-2-cis-hexenyl)-4-hydroxycyclopent-2-en-1-one

A solution of 1.0 mmole of all-cis-(6-carboxy-2-cis-hexenyl)-3,4-oxidocyclopentanone (Example 62) and 3.0 mmoles of sodium carbonate in 15 ml. of water is allowed to stand at room temperature for 3 hours. The solution is acidified with HCL, saturated with sodium chloride, and extracted with ether. The extract is washed with brine, dried over magnesium sulfate and concentrated to give a mixture of the title compound and the isomeric compound, 2-(6-carboxy-2-cis-hexenyl)-3-hydroxycyclopent-4-en-1-one. Further treatment of this mixture with 0.1N sodium hydroxide at room temperature for 30 minutes causes the rearrangement of the latter isomer to the title compound, which is isolated from the basic solution as above.

EXAMPLE 64

Preparation of 2-(6-carboxy-2-cis-hexenyl)-4-hydroxycyclopent-2-en-1-one

Treatment of cis-anti-cis-5-hydroxy-2,3-oxidocyclopentylacetaldehyde-γ-lactol (E. J. Corey and R. Noyori *Tetrahedron Letters*, 1970, 311), prepared from the corresponding lactone and diisobutylaluminum hydride as disclosed for the preparation of the corresponding cis-syn-cis lactol, with 4-carboxybutyltriphenylphosphonium bromide as described in Example 61 is productive of 2β-(6-carboxy-2-cis-hexenyl)-3α, 4α-oxidocyclopentan-1β-ol, which on oxidation by the method of Example 62 provides 2β-(6-carboxy-2-cis-hexenyl)-3α,4α-oxidocyclopentanone, which in turn on treatment with aqueous base by the procedure of Example 63 furnishes the subject compound.

EXAMPLE 65

Preparation of 2-(6-carboxy-2-cis-hexenyl)-3,4-oxidocyclopentanol

A solution of 5.0 g. (35 mmoles) of 5-hydroxy-2,3-oxidocyclopentylacetaldehyde-γ-lactol (isomeric mixture; E. J. Corey and R. Noyroi, *Tetrahedron Letters*, 1970, 311) in 25 ml. of DMSO is added during 0.5 minute at 20° C. to a stirred solution of the Wittig reagent [E. J. Corey et al. JACS, 91, 5675 (1069); also Example 61] and dimsyl sodium prepared from 23.5 g. (53 mmoles) of 4-carboxybutyltriphenylphosphonium bromide, 6.1 g. (140 mmoles) of 57% sodium hydride dispersion, and 230 ml. of DMSO (dimethylsulfoxide).

The solution is stirred at ambient temperatures for 2 hours and poured into a stirred mixture of methylene chloride, ice, and hydrochloric acid. The reaction mixture is worked up as described in Example 61, and the crude product is purified by dry column chromatography on silica gel to provide the title compound (mixture of two stereoisomers) as an oil, IR (film) 3450, 1710, and 832 $cm^{-1}$.

EXAMPLE 66

Preparation of 2-(6-carboxy-2-cis-hexenyl)-3,4-oxidocyclopentanone

A stirred solution of 2.98 g. (13.2 mmoles) of 2-(6-carboxy-2-cis-hexenyl)-3,4-oxidocyclopentanol (Example 65) in 66 ml. of acetone is treated dropwise with 3.30 ml. of 8N chromic acid in 8N $M_2SO_4$ during 20 minutes at $-10°$ to $-5°$ C. The solution is stirred at $-5°$ C. for 10 minutes and treated successively with a few drops of isopropanol and 12 ml. of water. The mixture is filtered, and the filtrate is concentrated, saturated with sodium chloride, and extracted with ethyl acetate. The extract is washed with brine, dried over $MgSO_4$, and evaporated to give an oil, IR (film) 1740, 1710, and 840 $cm^{-1}$.

EXAMPLE 67

Preparation of 2-(6-carboxy-2-cis-hexenyl)-4-hydroxycyclopent-2-en-1-one

A solution (pH: 10.2-10.5) of 2.42 g. (10.8 mmoles) of 2-(6-carboxy-2-cis-hexenyl)-3,4-oxidocyclopentanone (Example 66), 4.58 g. (43.2 mmoles) of sodium carbonate, and 216 ml. of water is allowed to stand at room temperature under nitrogen for 24 hours. The solution is acidified at 15° C. with hydrochloric acid and extracted with ethyl acetate. The extract is washed with brine, dried over $MgSO_4$, and evaporated to give an oil; IR (film) 1700 (carbonyl groups) and 1630 $cm^{-1}$ (conjugated olefin); NMR 7.11 (1), 5.54 (2), and 495 (1).

EXAMPLE 68

Preparation of 4-carboxybutyltriphenylphosphonium bromide

A mixture of 103 g. of 5-bromovaleric acid and 152 g. of triphenylphosphine in 400 ml. of acetonitrile is refluxed for 48 hours, cooled, diluted with 100 ml. of benzene and allowed to crystallize. The crystals are filtered, washed with benzene and ether, to yield colorless material, m.p. 207°-209° C.

EXAMPLE 69-75

Treatment of the indicated ω-bromoalkanoic acids of Table 5 below with triphenylphosphine by the method described in Example 68 produces the phosphonium bromides of the table.

TABLE 5

| Example | Starting ω-bromo-alkanone acid | Product Phosphonium bromide |
|---|---|---|
| 69 | 4-bromo-n-butyric acid | 3-carboxypropyltriphenylphosphonium bromide |
| 70 | 6-bromo-n-hexanoic acid | 5-carboxypentyltriphenylphosphonium bromide |
| 71 | 7-bromo-n-heptanoic acid | 6-carboxyhexyltriphenylphosphonium bromide |
| 72 | 5-bromo-4-methyl-n-pentanoic acid | (2-methyl-4-carboxybutyl)triphenylphosphonium bromide |
| 73 | 5-bromo-4(R)-methyl-n-pentanoic acid[1] | (2[R]-methyl-4-carboxybutyl)triphenylphosphonium bromide |
| 74 | 5-bromo-4-ethyl-n-pentanoic acid | (2-ethyl-4-carboxybutyl)triphenylphosphonium bromide |
| 75 | 5-bromo-4-propyl-n-pentanoic acid | (2-propyl-4-carboxybutyl)triphenylphosphonium bromide |

[1] J.S. Dalby, G.W. Kenner and R.C. Sheppard, J. Chem. Soc., 4387 (1962).

EXAMPLES 76-82

Treatment of 5-hydroxy-2,3-oxidocyclopentylacetaldehyde-γ-lactol (isomeric mixture) with the Wittig reagent prepared from the indicated phosphonium bromides of Table 6 below, all by the procedures of Examples 61 and 65 is productive of the product compounds of the table.

TABLE 6

| Example | Reagent phosphonium bromide of Example | Product 3,4-oxidocyclopentanol (isomeric mixture) |
|---|---|---|
| 76 | 69 | 2-(5-carboxy-2-cis-pentenyl)-3,4-oxidocyclopentan-1-ol |
| 77 | 70 | 2-(7-carboxy-2-cis-heptenyl)-3,4-oxidocyclopentan-1-ol |
| 78 | 71 | 2-(8-carboxy-2-cis-octenyl)-3,4-oxidocyclopentan-1-ol |
| 79 | 72 | 2-(6-carboxy-4-methyl-2-cis-hexenyl)-3,4-oxidocyclopentan-1-ol |
| 80 | 73 | 2-(6-carboxy-4(R)-methyl-2-cis-hexenyl)-3,4-oxidocyclopentan-1-ol |
| 81 | 74 | 2-(6-carboxy-4-ethyl-2-cis-hexenyl)-3,4-oxidocyclopentan-1-ol |
| 82 | 75 | 2-(6-carboxy-4-propyl-2-cis-hexenyl)-3,4-oxidocyclopentan-1-ol |

EXAMPLES 83-89

Oxidation of the cyclopentanols indicated in Table 7 below by the method described in Example 66 furnishes the corresponding product 3,4-oxidocyclopentanones of the table.

TABLE 7

| Example | Starting cyclopentan-1-ol of Example | Product 3,4-oxidocyclopentan-1-one |
|---|---|---|
| 83 | 76 | 2-(5-carboxy-2-cis-pentenyl)-3,4-oxidocyclopentan-1-one |
| 84 | 77 | 2-(7-carboxy-2-cis-heptenyl)-3,4-oxidocyclopentan-1-one |
| 85 | 78 | 2-(8-caboxy-2-cis-octenyl)-3,4-oxidocyclopentan-1-one |
| 86 | 79 | 2-(6-carboxy-4-methyl-2-cis-hexenyl)-3,4-oxidocyclopentan-1-one |
| 87 | 80 | 2-(6-carboxy-4(R)-methyl-2-cis-hexenyl)- |

TABLE 7-continued

| Example | Starting cyclopentan-1-ol of Example | Product 3,4-oxidocyclopentan-1-one |
|---------|--------------------------------------|-----------------------------------|
| | | 3,4-oxidocyclopentan-1-one |
| 88 | 81 | 2-(6-carboxy-4-ethyl-2-cis-hexenyl)-3,4-oxido-cyclopentan-1-one |
| 89 | 82 | 2-(6-carboxy-4-propyl-2-cis-hexenyl)-3,4-oxidocyclopentan-1-one |

EXAMPLES 90–96

Alkaline treatment of the 3,4-oxidocyclopentanones of Table 8 below by the process described in Example 67 is productive of the 4-hydroxycyclopentenones of the table.

TABLE 8

| Example | Starting 3,4-oxidocyclopentanone of Example | Product 4-hydroxycyclopent-2-en-1-one |
|---------|---------------------------------------------|---------------------------------------|
| 90 | 83 | 2-(5-carboxy-2-cis-pentenyl)-4-hydroxy-cyclopent-2-en-1-one |
| 91 | 84 | 2-(7-carboxy-2-cis-heptenyl)-4-hydroxy-cyclopent-2-en-1-one |
| 92 | 85 | 2-(8-carboxy-2-cis-octenyl)-4-hydroxy-cyclopent-2-en-1-one |
| 93 | 86 | 2-(6-carboxy-4-methyl-2-cis-hexenyl)-4-hydroxycyclopent-2-en-1-one |
| 94 | 87 | 2-(6-carboxy-4(R)-methyl-2-cis-hexenyl)-4-hydroxy-cyclopent-2-en-1-one |
| 95 | 88 | 2-(6-carboxy-4-ethyl-2-cis-hexenyl)-4-hydroxy-cyclopent-2-en-1-one |
| 96 | 89 | 2-(6-carboxy-4-propyl-2-cis-hexenyl)-4-hydroxy-cyclopent-2-en-1-one |

EXAMPLE 97

Preparation of 4-tetrahydropyranyloxy-2-(6-carbotetrahydropyranyloxy-2-cis-hexenyl)cyclopent-2-en-1-one A vigorously stirred, ice-cold solution of 9.45 g. (42.5 mmoles) of 2-(6-carboxy-cis-2-hexenyl)-4-hydroxycyclopent-2-en-1-one (Example 67) and 14.3 g. (170 mmoles of dihydropyran in 212 ml. of methylene chloride is treated with 81 mg. (0.425 mmoles) of p-toluenesulfonic acid monohydrate. After stirring for 5 minutes at 0° C. and 60 minutes at 25° C. the solution is poured into a stirred mixture of 40 ml. of saturated brine, 40 ml. of saturated sodium bicarbonate and 80 ml. of water. The organic phase is washed with brine, dried over magnesium sulfate, and concentrated to give an oil, $\theta$ max (film) 1730 (ester carbonyl), 1710 (ketone carbonyl), and 1030 cm$^{-1}$ (tetrahydropyranyloxy groups).

EXAMPLE 97a

Preparation of 4(R)-tetrahydropyranyloxy-2-(6-carbomethoxy-2-cis-hexenyl)cyclopent-2-en-1-one This compound is prepared as described in the literature; J. B. Heather et al., *Tetrahedron Letters*, 2313 (1973).

EXAMPLES 98–104

Treatment of the 4-hydroxycyclopent-2-en-1-ones listed in Table 9 below with dihydropyran in the manner of Example 97 is productive of the corresponding bis-tetrahydropyranyl ether-esters of the table.

TABLE 9

| Example | Starting 4-hydroxycyclopent-2-en-1-one of Example | Product bis-tetrahydropyranyl ether-ester |
|---------|---------------------------------------------------|-------------------------------------------|
| 98 | 90 | 4-tetrahydropyranyloxy-2-(5-carbotetrahydropyranyloxy-2-cis-pentenyl)cyclopent-2-en-1-one |
| 99 | 91 | 4-tetrahydropyranyloxy-2-(7-carbotetrahydropyranyloxy-2-cis-heptenyl)-cyclopent-2-en-1-one |
| 100 | 92 | 4-tetrahydropyranyloxy-2-(8-carbotetrahydropyranyloxy-2-cis-octenyl)-cyclopent-2-en-1-one |
| 101 | 93 | 4-tetrahydropyranyloxy-2-(6-carbotetrahydropyranyloxy-4-methyl-2-cis-hexenyl)-cyclopent-2-en-1-one |
| 102 | 94 | 4-tetrahydropyranyloxy-2-(6-carbotetrahydropyranyloxy-4(R)-methyl)-2-cis-hexenyl-cyclopent-2-en-1-one |
| 103 | 95 | 4-tetrahydropyranyloxy-2-(6-carbotetrahydropyranyloxy-4-ethyl-2-cis-hexenyl)-cyclopent-2-en-1-one |
| 104 | 96 | 4-tetrahydropyranyloxy-2-(6-carbotetrahydropyranyloxy-4-propyl-2-cis-hexenyl)cyclopent-2-en-1-one |

EXAMPLE 105

Preparation of 4-(trimethylsiloxy)-2-(6-carbotrimethylsiloxy-2-cis-hexenyl)cyclopent-2-en-1-one To a solution of 5 g. of 2-(6-carboxy-2-cis-hexenyl)-4-hydroxy-cyclopent-2-en-1-one (Example 67) in 10 ml. of dry N,N-dimethylformamide is added 5.4 g. of trimethylsilyl chloride in a nitrogen atmosphere. To the resulting solution cooled in a tap water bath is added 5.05 g. of triethylamine in 10 ml. of N,N-dimethylformamide, dropwise. The resulting mixture is stirred at 60° C. in an oil-bath for 2 hours, then at ambient temperatures for 18 hours. Triethylamine hydrochloride is removed by filtration and the filtrate is taken to dryness. The residual oil is further purified by distillation at high vacuum.

EXAMPLES 106–113

Treatment of the 4-hydroxycyclopent-2-en-1-ones listed in Table 10 below with the indicated trialkylsilyl chloride by the method described in Example 105 is productive of the bis-trialkylsilyl ether-esters of the table.

TABLE 10

| Example | Starting 4-hydroxy-cyclopentenone of Example | Trialkylsilyl-chloride | Product bis-trialkylsilyl ether-ester |
|---|---|---|---|
| 106 | 90 | $(CH_3)_3SiCl$ | 4-trimethylsiloxy-2-(5-carbotrimethylsiloxy-2-cis-pentyl)cyclopent-2-en-1-one |
| 107 | 91 | $(CH_3)_3SiCl$ | 4-trimethylsiloxy-2-(7-carbotrimethylsiloxy-2-cis-heptenyl)cyclopent-2-en-1-one |
| 108 | 92 | $(CH_3)_3SiCl$ | 4-trimethylsiloxy-2-(8-carbotrimethylsiloxy-2-cis-octenyl)cyclopent-2-en-1-one |
| 109 | 67 | dimethylisopropyl silyl chloride[a] | 4-dimethylisopropylsiloxy-2-(6-carbodimethylisopropyl iloxy-2-cis-hexenyl)cyclopent-2-en-1-one |
| 110 | 93 | $(CH_3)_3SiCl$ | 4-trimethylsilyloxy-2-(6-carbotrimethylsilyloxy-4-methyl-2-cis-hexenyl)cyclopent-2-en-1-one |
| 111 | 94 | $(CH_3)_3SiCl$ | 4-trimethylsilyloxy-2-(6-carbotrimethylsilyloxy-4(R)-methyl-2-cis-hexenyl)cyclopent-2-en-1-one |
| 112 | 95 | $(CH_3)_3SiCl$ | 4-trimethylsilyloxy-2-(6-carbotrimethylsilyloxy-4-ethyl-2-cis-hexenyl)cyclopent-2-en-1-one |
| 113 | 96 | $(CH_3)_3SiCl$ | 4-trimethylsilyloxy-2-(6-carbotrimethylsilyloxy-4-propyl-2-cis-hexenyl)cyclopent-2-en-1-one |

[a]E.J. Corey, R.K. Varma, J. Amer. Chem. Soc., 93, 7320 (1970).

EXAMPLE 113A

Preparation of 4-(t-butyldimethylsiloxy)-2-(6-carbo-t-butyldimethylsiloxyhexyl)cyclopent-2-en-1-one To a stirred solution of 2-(6-carboxyhexyl)-4-hydroxycyclopent-2-en-1-one and 7.9 g. of imidazole in 12.5 ml. of dry dimethylformamide is added 10.2 g. of t-butyldimethylsilyl chloride in 12.5 ml. of dimethylformamaide at 0° C. The solution is then stirred for 4 hours at 37° C. The solution is poured into 350 ml. of ice cold water and extracted twice with hexane. The combined extracts are washed with 5% sodium carbonate solution; saturated sodium chloride solution, dried with anhydrous magnesium sulfate and evaporated under reduced pressure. The residue is twice evaporated with toluene to give 9.52 g. (95%) of product as an oil.

EXAMPLE 114

Preparation of cyclopentylacetyl chloride

To a solution of 50 g. of cyclopentaneacetic acid containing 2.9 ml. of N,N-dimethylformamide is added dropwise with stirring, 51 g. of thionyl chloride over a period of 15 minutes. After stirring for an additional 60 minutes excess thionyl chloride is removed in vacuo and the residual oil is distilled to give 55.4 g. (97%) of product, b.p. 57°–58° C. (10 mm.).

EXAMPLE 115

Preparation of 1-chloro-4-cyclopentyl-1-trans-buten-3-one

A three-necked flask fitted with a stirrer, a gas inlet tube and a gas outlet tube protected with a calcium chloride tube is surrounded by an ice-water bath. The system is flushed with acetylene for 3 minutes. Carbon tetrachloride (150 ml.) is added to the flask and acetylene is bubbled through at a fast rate for 3 minutes. Aluminum chloride (59 g.) is added and acetylene is bubbled through the mixture for 5 minutes. The gas inlet tube is replaced by a dropping funnel protected by a calcium chloride drying tube. Cyclopentylacetyl chloride (55.4 g., Example 114) is added to the reaction mixture stirring over a period of about 20 minutes. The dropping funnel is replaced by the gas inlet tube and with stirring, acetylene gas is bubbled through at a rate in excess of the saturation rate. After about 15 minutes the rate of absorption of acetylene suddenly becomes very rapid, and the acetylene is passed through as rapidly as it is absorbed. The introduction of acetylene is continued for 45 minutes after the rapid absorption (which lasts about 1 hour) has subsided.

The reaction mixture is poured with stirring onto 430 g. of ice and 180 ml. of saturated sodium chloride solution. The aqueous phase is extracted three times with ether. The combined extracts are dried with anhydrous magnesium sulfate and evaporated to dryness in vacuo. After addition of 1.5 g. of hydroquinone the residual oil is distilled to give 57 g. (80%) of oil, b.p. 67°–69° C. (0.14 mm.).

EXAMPLE 116

Preparation of 4-cyclopentyl-1-iodo-1-trans-buten-3-one

A solution of 57 g. of 1-chloro-4-cyclopentyl-trans-buten-3-one (Example 115) in 360 ml. of acetone containing 55 g. of sodium iodide is stirred at the reflux temperature for 18 hours. The resulting mixture is cooled, filtered and and the water liquor is taken to dryness. The residual oil is dissolved in ether washed successively with water, dilute sodium thiosulfate solution, and saturated sodium chloride solution, dried with anhydrous magnesium sulfate and taken to dryness to give 87g. (99%) of orange oil. Vapor phase chromatography shows one peak.

EXAMPLE 117

Preparation of 4-cyclopentyl-1-iodo-1-trans-buten-3-ol

To a solution of 7.1 g. of sodium borohydride in 60 ml. of absolute alcohol, stirred in an ice bath under nitrogen atmosphere, is added dropwise, over a period of about 2 hours, a solution containing 7 g. of 4-cyclopentyl-1-iodo-1-trans-buten-3-one (Example 116) in 160 ml. of absolute alcohol. The temperature is maintained at 5°–10° C. The solution is poured into 850 ml. of iced water and the resulting mixture is extracted three times with ether. The combined extracts are washed with dilute sodium bisulfite solution, saturated sodium chloride solution, dried with anhydrous magnesium sulfate and taken to dryness to give 81 g. of yellow oil. Column chromatography on a column of 1 kg. of silica gel using benzene gives 75 g. (88%) of oily product.

EXAMPLES 118–141

Treatment of the listed carboxylic acids in Table 11 below with thionyl chloride by the procedure disclosed in Example 114 followed by treatment of the resulting acid chloride with acetylene by the procedure described in Example 115, and thence by treatment of the resulting 1-chloro-1-trans-alkene-3-one with sodium iodide by the procedure described in Example 116, and then by treatment of the resulting 1-iodo-1-trans-alkene-3-one with sodium borohydride by the procedure described in Example 117 is productive of the product 3-hydroxy-1-iodo-1-trans-alkenes of the table.

TABLE 11

| Example | Starting Carboxylic acid | Product 3-hydroxy-1-iodo-1-trans-alkene |
|---|---|---|
| 118 | Cyclobutylacetic acid[1] | 4-Cyclobutyl-3-hydroxy-1-iodo-1-trans-butene |
| 119 | 3-Cyclopentyl-propionic acid | 5-Cyclopentyl-3-hydroxy-1-iodo-1-trans-pentene |
| 120 | 4-Cyclopentyl-butyric acid[2] | 6-Cyclopentyl-3-hydroxy-1-iodo-1-trans-hexene |
| 121 | 5-Cyclopentyl-pentanoic acid[2] | 7-Cyclopentyl-3-hydroxy-1-iodo-1-trans-heptene |
| 122 | 6-Cyclopentyl-hexanoic acid[2] | 8-Cyclopentyl-3-hydroxy-1-iodo-1-trans-octene |
| 123 | 2-Methyl-3-cyclopentylpropanoic acid[3] | 5-Cyclopentyl-4-methyl-3-hydroxy-1-iodo-1-trans-pentene |
| 124 | 2-Ethyl-4-cyclopentylbutyric acid[4] | 6-cyclopentyl-4-ethyl-3-hydroxy-1-iodo-1-trans-hexene |
| 125 | (2-trans-methylcyclopentyl)-acetic acid[5] | 4-(2-trans-methylcyclopentyl)-3-hydroxy-1-iodo-1-trans-butene |
| 126 | 4-(2-trans-methylcyclopentyl)butyric acid[5] | 6-(2-trans-methylcyclopentyl)-3-hydroxy-1-iodo-1-trans-hexene |
| 127 | Cyclohexylacetic acid | 4-Cyclohexyl-3-hydroxy-1-iodo-1-trans-1-trans-butene |
| 128 | 3-Cyclohexyl-propionic acid | 5-cyclohexyl-3-hydroxy-1-iodo-1-trans-pentene |
| 129 | 4-Cyclohexyl-butyric acid[6] | 6-cyclohexyl-3-hydroxy-1-iodo-1-trans-hexene |
| 130 | Cycloheptyl-acetic acid[7] | 4-Cycloheptyl-3-hydroxy-1-iodo-1-trans-butene |
| 131 | (4-methylcycloheptyl)acetic acid[8] | 4-(4-methylcycloheptyl)-3-hydroxy-1-iodo-1-trans-butene |
| 132 | Cyclooctylacetic acid[8,9] | 4-Cyclooctyl-3-hydroxy-1-iodo-1-trans-butene |
| 133 | (4-methylcyclohexyl)acetic acid[10] | 4-(4-methylcyclohexyl)-3-hydroxy-1-iodo-1-trans-butene |
| 134 | (3-methylcyclohexyl)acetic acid[11] | 4-(3-methylcyclohexyl)-3-hydroxy-1-iodo-1-trans-butene |
| 135 | 3-Cycloheptane carboxylic acid | 3-Cycloheptyl-3-hydroxy-1-iodo-1-trans-propene |
| 136 | Cyclopentane-carboxylic acid | 3-Cyclopentyl-3-hydroxy-1-iodo-1-trans-propene |
| 137 | Trans-2-methyl-cyclopentane carboxylic acid[12] | 3-(Trans-2-methylcyclopentyl-3-hydroxy-1-iodo-1-trans-propene |
| 138 | all-trans-2,3-dimethylcyclopentane carboxylic acid[13] | 3-(all-trans-2,3-dimethylcyclopentyl)-1-=iodo-1-trans-propene |
| 139 | Cyclohexane carboxylic acid | 3-Cyclohexyl-3-hydroxy-1-iodo-1-trans-propene |
| 140 | Trans-4-methyl-cyclohexane carboxylic acid | 3-(trans-4-methylcyclohexyl)-3-hydroxy-1-iodo-1-trans-propene |
| 141 | Cyclooctane carboxylic acid[14] | 3-Cyclooctyl-3-hydroxy-1-iodo-1-trans-propene |

[1] C. G. Overberger et al., J. Polymer Sci., Pt. A, 2, 755(196).
[2] M. I. Goryaev et al., Chem. Abs., 69, 1742, No. 186462 (1968).
[3] C. D. Nenitzescu and G. G. Vantu, Bull. Soc. Chim.
[4] France [5]. 2, 2209 (1935). 4 G. R. Yohe and R. Adams, J. Amer. Chem. Soc., 50, 1503 (1928).
[5] W. Herz, J. Org. Chem., 20, 1062 (1955).
[6] G. S. Hiers and R. Adams, J. Amer. Chem. Soc., 48, 2385 (1926).
[7] E. E. Royals and A. N. Neal, J. Org. Chem., 21, 1448 (1956)
[8] F. F. Blicke and W. K. Johnson, J. Am. Pharm. Assoc. Sci. Ed., 45, 443 (1956).
[9] L. Ruzicka and H. A. Bockenoogen, Helv. Chim. Acta, 14, 1319 (1931).
[10] A. W. Burgstahler and I. C. Nordin, J. Amer. Chem. Soc., 83, 198 (1961).
[11] J. von Braun and W. Teuffert, Ber., 58B, 2210 (1925).
[12] M. Julia and F. LeGoffie, Bull. Soc. Chim. Fr., 1550 (1965).
[13] V. N. Ipatieff et al., J. Amer. Chem. Soc., 75, 6222 (1953).
[14] A. T. Blomquist and F. W. Sehlaefe, J. Amer. Chem. Soc., 83 4547 (1961).

EXAMPLE 142

Preparation of 4-cyclopentyl-1-iodo-3-triphenylmethoxy-1-trans-butene

A mixture of 21.4 g. of 4-cyclopentyl-1-iodo-trans-buten-3-ol (Example 117) in 170 ml. of dry pyridine containing 31 g. of triphenylmethyl bromide is heated on the steam bath for 2 hours. The dark mixture is poured into 850 ml. of iced water and the resulting solution is extracted three times with ether. The combined extracts are washed with ice cold 2% hydro chloric acid until the washings are acidic, saturated sodium chloride solution, dried with anhydrous magnesium sulfate and taken to dryness. Trituration of the residue followed by filtration removes triphenylcarbinol. The mother liquor is taken to dryness and the residual syrup is chromatographed on 400 g. of florisil using hexane gives 32 g. (78%) of syrup which solidifies on standing. Recrystallization from hexane affords white crystals, m.p. 87°–88° C.

EXAMPLE 143

Preparation of 4-cyclopentyl-1-iodo-3-(p-methoxyphenyldiphenyl)methoxy-1-trans-butene A solution of 20 g. of 4-cyclopentyl-1-iodo-1-trans-buten-3-ol (Example 117) and 25 g. of p-anisylchlorodiphenylmethane in 170 ml. of dry pyridine is kept at 60° C. for 18 hours, then at 70° C. for 3 hours. The cooled solution is poured into 850 ml. of iced water. The resulting solution is partitioned between ether and water. The ether layer is washed with water, dried with anhydrous magnesium sulfate and taken to dryness. Further evaporation with toluene removes residual pyridine. The resulting oil is chromatographed on 300 g. of florisil with hexanes to give 22.3 g. of product. The material is homogeneous according to thin layer chromatography.

EXAMPLES 114–167

Treatment of the listed 3-hydroxy-1-iodo-trans-1-alkenes of Table 12 below with triphenylmethylbromide by the procedure described in Example 142 above is productive of the product 3-triphenylmethoxy-1-iodo-trans-1-alkenes of the table.

TABLE 12

| Example | Starting 3-hydroxy-1-iodo-1-trans-alkene of Example | Product 3-triphenylmethoxy-1-iodo-trans-1-alkene- |
|---|---|---|
| 144 | 118 | 4-Cyclobutyl-3-triphenylmethoxy-1-iodo-1-trans-butene |
| 145 | 119 | 5-Cyclopentyl-3-triphenylmethoxy-1-iodo-1-trans-pentene |
| 146 | 120 | 6-Cyclopentyl-3-triphenylmethoxy-1-iodo-1-trans-hexene |
| 147 | 121 | 7-Cyclopentyl-3-triphenylmethoxy-1-iodo-1-trans-heptene |
| 148 | 122 | 8-Cyclopentyl-3-triphenylmethoxy-1-iodo-1-trans-octene |
| 149 | 123 | 5-Cyclopentyl-4-methyl-3-triphenylmethoxy-1-iodo-1-trans-pentene |
| 150 | 124 | 6-Cyclopentyl-4-ethyl-3-triphenylmethoxy-1-iodo-1-trans-hexene |
| 151 | 125 | 4-(2-trans-methylcyclopentyl)-3-triphenyl- |

TABLE 12-continued

| Example | Starting 3-hydroxy-1-iodo-1-trans-alkene of Example | Product 3-triphenylmethoxy-1-iodo-trans-1-alkene- |
|---|---|---|
| | | methoxy-1-iodo-1-trans-butene |
| 152 | 126 | 6-(2-trans-methylcyclopentyl)-3-triphenylmethoxy-1-iodo-1-trans-hexene |
| 153 | 127 | 4-Cyclohexyl-3-triphenylmethoxy-1-iodo-1-trans-butene |
| 154 | 128 | 5-Cyclohexyl-3-triphenylmethoxy-1-iodo-1-trans-pentene |
| 155 | 129 | 6-Cyclohexyl-3-triphenylmethoxy-1-iodo-1-trans-hexene |
| 156 | 130 | 4-Cycloheptyl-3-triphenylmethoxy-1-iodo-1-trans-butene |
| 157 | 131 | 4-(4-methylcycloheptyl)-3-triphenylmethoxy-1-iodo-1-trans-butene |
| 158 | 132 | 4-Cyclooctyl-3-triphenylmethoxy-1-iodo-1-trans-butene |
| 159 | 133 | 4-(4-methylcyclohexyl)-3-triphenylmethoxy-1-iodo-1-trans-butene |
| 160 | 134 | 4-(3-methylcyclohexyl)-3-triphenylmethoxy-1-iodo-1-trans-butene |
| 161 | 135 | 3-Cycloheptyl-3-triphenylmethoxy-1-iodo-1-trans-propene |
| 162 | 136 | 3-Cyclopentyl-3-triphenylmethoxy-1-iodo-1-trans-propene |
| 163 | 137 | 3-(trans-2-methylcyclopentyl)-3-triphenylmethoxy-1-iodo-1-trans-propene |
| 164 | 138 | 3-(all-trans-2,3-dimethylcyclopentyl)-3-triphenylmethoxy-1-iodo-1-trans-propene |
| 165 | 139 | 3-Cyclohexyl-3-triphenylmethoxy-1-iodo-1-trans-propene |
| 166 | 140 | 3-(trans-4-methylcyclohexyl)-3-triphenylmethoxy-1-iodo-1-trans-propene |
| 167 | 141 | 3-Cyclooctyl-3-triphenylmethoxy-1-iodo-1-trans-propene |

EXAMPLE 168

Preparation of 1,1-dimethyl-cis-3,4-methylenehexane (cis-1-ethyl-2(2,2-dimethoxyethyl)cyclopropane To an ethereal suspension of zinc-silver couple, prepared according to the procedure of J. M. Denis, G. Girard, and J. M. Conia (*Synthesis*, 1972, 549) from 0.400 g. of silver acetate, 400 ml. of acetic acid, 68 g. of granular zinc, silver wool, and 600 ml. of ether is added dropwise 136 g. of diiodomethane at a rate to mainatin a gentle reflux. The mixture is then stirred at room temperature for 1 hour and to it is then added 57.7 g. of 1,1-dimethoxy-cis-3-hexene. [(M. Winter, *Helvetica Chimica Acta*, 46, 1972 (1963)] over a period of 20 minutes and the mixture is refluxed for 5 hours. The mixture is cooled to 0° C., 600 ml. of ether is added followed by 50.5 g. of pyridine dropwise over a period of 1 hour. The resulting precipiate is filtered and washed with ether. The filtrate and washings are combined and evaporated and the residue is fractionally distilled at 12 torr to yield the title compound as a colorless oil.

EXAMPLE 169

Preparation of cis-3,4-methylene-1-hexanol

To a vigorously stirred solution of 31.6 g. of 1,1-dimethoxy-cis-3,4-methylene-hexane (Example 168), 75 mg. of hydroquinone, 6 g. of oxalic acid in 150 ml. of acetone heated at 45° C. under an inert atmosphere is added 700 ml. of water over a period of 0.5 hours. The mixture is cooled and extracted well with ether. The organic phase is separated, washed with saturated sodium bicarbonate solution and saturated brine, dried (Na$_2$SO$_4$) and evaporated. The residue is distilled at 30 torr. to yield the title compound.

EXAMPLE 170

Preparation of cis-5,6-methylene-1-octyn-3-ol

To a solution of 15.2 g. (0.165 mole) of lithium acetylide-ethylenediamine complex in 100 ml. of dry dimethylsulfoxide is added 16.8 g. (0.150 mole) of cis-3,4-methylene-1-hexanol (Example 169) in 25 ml. of dimethylsulfoxide at a rate to maintain a temperature of 25° C. (cooling). The mixture is then maintained at 25° C. for 2 hours and is poured onto ice and excess hydrochloric acid. The mixture is extracted with ether and the organic phase is washed with water and saturated brine, dried (Na$_2$SO$_4$), and evaporated to an oil. Distillation in vacuo yields the title compound as a colorless oil.

EXAMPLE 171

Preparation of 3-triphenylmethoxy-cis-5,6-methylene-1-octyne

A mixture of 13.8 g. of cis-5,6-methylene-1-octyn-3-ol (Example 170) and 33.0 g. of triphenylmethyl bromide in 100 ml. of pyridine is heated to 100° C. for 1.5 hours under an inert atmosphere. The mixture is cooled and filtered. The filtrate is partitioned between ice water and ether. The organic phase is washed with cold dilute hydrochloric acid, saturated sodium bicarbonate solution, and saturated brine, dried (NaSO$_4$), and evaporated to an oil. The latter is dissolved in hexane and passed through 400 g. of Florisil ® to yield after evaporation the title compound as a colorless oil.

EXAMPLE 172

Preparation of 1-iodo-3-triphenylmethoxy-cis-5,6-methylene-trans-1-octene

To 160 ml. of a 0.50M solution of disiamylborane in diglyme cooled to 0° C. under an inert atmosphere is added 28.6 g. (0.075 mole) 3-triphenylmethoxy-cis-5,6-methylene-1-octyne (Example 171). The mixture is allowed to come to room temperature and is stirred at ambient temperature for 3 hours. The solution is cooled to 0° C. and 16.9 g. (0.225 mole) of triethylamine oxide is added portionwise such that the temperature is maintained at 0°-5° C. The mixture is stirred at 0° C. for 1 hour and is then poured into 300 ml. of 1 N sodium hydroxide followed immediately by a solution of 57 g. (0.225 mole) of iodine in 150 ml. of tetrahydrofuran. The mixture is stirred at ambient temperatures for 0.5 hour and poured into 1000 ml. of water. The mixture is decolorized by addition of sodium thiosulfate solution and is extracted into ether. The organic phase is washed with water and the solvent is removed in vacuo. The residue is purified by dry-column chromatography upon 1.5 kg. of alumina using hexane as eluent The title compound is obtained as an oil.

EXAMPLES 173–179

Treatment of the carboxaldehydes listed in Table 13 below with lithium acetylide by the procedure described in Example 170 followed by treatment of the resulting 3-hydroxy-1-alkyne with triphenylmethyl bromide by the procedure of Example 171 furnishes the product 3-triphenylmethoxy-1-alkynes of the table.

TABLE 13

| Example | Starting carboxaldehyde | Product 3-triphenylmethoxy-1-alkynes |
|---|---|---|
| 173 | (2-cyclopentenyl)acetaldehyde[1] | 4-(2-cyclopentenyl)-3-triphenylmethoxy-1-butyne |
| 174 | (2-cyclohexenyl)acetaldehyde[1] | 4-(2-cyclohexenyl)-3-triphenylmethoxy-1-butyne |
| 175 | (3-cyclohexenyl)acetaldehyde[1] | 4-(3-cyclohexenyl)-3-triphenylmethoxy-1-butyne |
| 176 | 1-methyl-1-formylmethylcyclohexane | 1-methyl-1-(3-triphenylmethoxy-1-butynyl-4)cyclohexane |
| 177 | 2-cyclohexene carboxaldehyde | 3-(2-cyclohexenyl)-3-triphenylmethoxy-1-propyne |
| 178 | 3-cyclohexene carboxaldehyde | 3-(3-cyclohexenyl)-3-triphenylmethoxy-1-propyne |
| 179 | 3-cyclohexyl-2-methylpropionaldehyde | 5-cyclohexyl-4-methyl-3-triphenylmethoxy-1-pentyne |

[1] C. W. Whitehead et al., J. Org. Chem., 26, 2814 (1961).
[2] A.I. Meyers et al., ibid., 38, 2136 (1973).

EXAMPLES 180–186

Treatment of the 3-triphenylmethoxy-1-alkynes listed in Table 14 below with disiamylborane, trimethylamine oxide; iodine and aqueous sodium hydroxide by the procedure described in Example 172 furnishes the product 3-triphenylmethoxy-1-iodo-1-trans-alkenes of the table.

TABLE 14

| Example | Starting 3-triphenylmethoxy-1-alkynes of Example | Product 3-triphenylmethoxy-1-iodo-1-trans-alkene |
|---|---|---|
| 180 | 173 | 4-(2-cyclopentenyl)-3-triphenylmethoxy-1-iodo-1-trans-butene |
| 181 | 174 | 4-(2-cyclohexenyl)-3-triphenylmethoxy-1-iodo-1-trans-butene |
| 182 | 175 | 4-(3-cyclohexenyl)-3-triphenylmethoxy-1-iodo-1-trans-butene |
| 183 | 176 | 1-methyl-1-(3-triphenylmethoxy-1-iodo-trans-1-butenyl-4)cyclohexene |
| 184 | 177 | 3-(2-cyclohexenyl)-3-triphenylmethoxy-1-iodo-1-trans-propene |
| 185 | 178 | 3-(3-cyclohexenyl)-3-triphenylmethoxy-1-iodo-1-trans-propene |
| 186 | 179 | 5-cyclohexyl-4-methyl-3-triphenylmethoxy-1-iodo-1-trans-pentene |

EXAMPLE 187

Preparation of
9-oxo-11α,15-dihydroxy-17,20-methano-13-trans-prostenoic acid and
9-oxo-11α,15-epi-dihydroxy-17,20-methano-13-trans-prostenoic acid To a solution of 13.7 g. of 4-cyclopentyl-1-iodo-3-triphenylmethoxy-trans-1-butene (Example 142) in 35 ml. of dry toluene, cooled to −75° C., under nitrogen atmosphere is added dropwise in 5 minutes, 11.3 ml. of 2.34 molar solution of n-butyllithium in hexane. The solution is allowed to warm to −40° C. and maintained at that temperature for one hour. This solution containing (3-triphenylmethoxy-4-cyclopentyl-trans-1-butenyl)lithium is cooled to −75° C. and to it is added 18.1 ml. of a 1.45 molar solution of trimethylaluminum in hexane. The solution is then allowed to warm to −20° C. during 45 minutes. This solution containing lithio 3-triphenylmethoxy-4-cyclopentyl-1-trans-butenyl)trimethyl alanate is treated dropwise with 9.5 g. Of 2-(6-carbotetrahydropyranyloxyhexyl)-4-tetrahydropyranyloxy-2-cyclopentenone in 10 ml. of ether, rinsing with 5 ml. of ether. The resulting yellow brown solution is allowed to warm to ambient temperature and then kept at that temperature for 18 hours. The solution is poured cautiously onto a mixture of 14 ml. of concentrated hydrochloric acid with 400 g. of crushed ice and the resulting mixture is stirred for 15 minutes. Extraction with ether followed by evaporation gives 22 g. of an oily material. A solution of the oil in 350 ml. of acetic acid-tetrahydrofuran-water (3:1:1) is stirred at ambient temperature for 48 hours under nitrogen atmosphere and then taken to dryness. Evaporation to dryness with xylene affords 20 g. of oily material, which is chromatographed on 350 g. of Silic Ar (cc 4). Elution is effected with increasing percentages of benzene in ethyl acetate; the fraction eluted with 80% ethyl acetate in benzene (1.2 l.) affords 1.4 g. of 9-oxo-11α, 15-epi-dihydroxy-17,20-methano-13-trans-prostenoic acid, crystallization of which from ethyl acetate gives white crystals, m.p. 98°–99° C.

EXAMPLE 188

To a solution of 13.7 g. (26.3 mmoles) of 4-cyclopentyl-1-iodo-3-mono-p-methoxytriphenylmethoxy-trans-1-butene (Example 143) in 35 ml. of dry toluene, cooled to −75° C., under nitrogen atmosphere is added dropwise in 5 minutes, 11.3 ml. (26.3 mmoles) of 2.34 molar solution of 2.34 molar solution of n-butyllithium in hexane. The solution is allowed to warm to −40° C. and maintained at that temperature for one hour. This solution containing (3-mono-p-methoxytriphenylmethoxy-4-cyclopentyl-trans-1-butenyl)lithium is cooled to −75° C. and to it is added 18.1 ml. (26.3 mmoles) of a 1.45 molar solution of trimethylaluminum in hexane. The solutionn is then allowed to warm to −20° C. during 45 minutes. This solution containing lithio(3-mono-p-methoxytriphenylmethoxy-4-cyclopentyl-1-trans-butenyl)trimethyl alanate is treated dropwise with 9.5 g. (20.8 mmoles) of 2-(6-carbo-t-butyldimethylsiloxyhexyl)-4-t-butyldimethylsiloxy-2-cyclopentenone (Example 113A) in 10 ml. of ether, rinsing with 5 ml. of ether. The resulting yellow brown solution is allowed to warm to ambient temperature and then kept at that temperature for 18 hours. The solution is poured cautiously onto a mixture of 14.5 ml. of concentrated hydrochloric acid with 400 g. of crushed ice and the resulting mixture is stirred for 15 minutes. Extraction with ether followed by evaporation gives 22 g. of an oily material. A solution of the oil in 350 ml. of acetic acid-tetrahydrofuran-water (3:1:1) is stirred at ambient temperature for 48 hours under nitrogen atmosphere and then taken to dryness. Evaporation to dryness with xylene affords 20 g. of oily material, which is chromatographed on 350 g. of Silic Ar (cc 4). Elution is effected with increasing percentages of benzene in ethyl acetate and finally with ethyl acetate. The following 600 ml. fractions are obtained: fractions 1-5 (11 g.) monomethoxytriphenylcarbinol and t-butyldimethylsilylated products; fraction 6 (0.931 g.), 9-oxo-11α-t-butyldimethylsiloxy-15-hydroxy-17,20-methano-13-trans-prostenoic acid; fraction 7-8 (1.9 g.), 15-35% 9-oxo-11α-t-butyldimethylsiloxy-15-hydroxy-17,20-methano-13-trans-prostenoic acid and 65.8% 9-oxo-15-hydroxy-17,20-methano-10,13-trans-prostadienoic acid; fractions 10 and 11 (1.43 g.), a mixture of 9-oxo-11α,15-epi-dihydroxy-17,20-methano-13-trans-prostenoic acid and 9-oxo-15-epi-17,20-methano-10,13-trans-prostadienoic acid; fraction 12 (1.2 g.) 9-oxo-11α,15-dihydroxy-17,20-methano-13-trans-prostenoic acid, crystallization of which twice from ethyl acetate furnishes white crystals, m.p. 98°–99° C.

EXAMPLE 188A

9-Oxo-15-epi-17,20-methano-10,13-trans-prostadienoic acid

A solution of 50 mg. of 9-oxo-15-epi-17,20-methano-10,13-trans-prostenoic acid (Example 187) is stirred in 1 ml. of 1.5N hydrochloric acid and 2 ml. of tetrahydrofuran and described in Example 486 to give 43.4 mg. of product. Recrystallization from ether affords white crystals, m.p. 86°–88° C.; $\lambda_{max}^{EtOH}$ 218 mu ($\epsilon$ 10,000); tlc Rf 0.75 on silica gel plate, ethyl acetate-acetone-acetic acid (90:20:1) development.

EXAMPLE 188B

9α,11α,15-trihydroxy-17,20-methano-13-trans-prostenoic acid

To a stirred solution of 931 mg. of 9-oxo-11α-t-butyldimethylsilyloxy-15-hydroxy-17,20-methano-13-trans-prostenoic acid in 5 ml. of tetrahydrofuran at 0° C. is added 6.7 ml. (2.2 mole equivalents) of 0.65 M lithium perhydro-9b-boraphenalyl hydride. After 40 minutes the solution is quenched with 4 ml. of 3N sodium hydroxide followed by 4 ml. of 30% hydrogen peroxide. Ether is added and the solution is acidified with 5% hydrochloric acid solution. The ether portion is separated and washed with saturated sodium chloride solution; dried with anhydrous magnesium sulfate and taken to dryness to give 11α-t-butyldimethylsiloxy-9α,15-dihydroxy-17,20-methano-13-trans-prostenoic acid. This material is then treated with 20 ml. of acetic acid-tetrahydrofuran-water (3:1:1) under nitrogen atmosphere at 30°–35° C. for 70 hours. The solution is taken to dryness under reduced pressure then evaporated twice from toluene under reduced pressure to give 748 mg. of product as an oil.

EXAMPLES 189–325

Treatment by the procedure of Example 187 of the 4-oxycyclopentenone esters listed in Table 15 below with the lithio trimethyl (3-triphenylmethoxy-trans-1-alkenyl)alanate corresponding to the listed 1-iodo-3-triphenylmethoxy-trans-1-alkene and prepared from it by the procedure of Example 187 by treatment first with butyl lithium and thence with trimethyl aluminum, followed by deblocking of the intermediate tetrahydropyranyl (or alkyl) 9-oxo-11α-tetrahydropyranyl-15-triphenylmethoxy-13-trans-prostenoates with acetic acid:water:tetrahydrofuran, also as described in Example 187, provides the product 9-oxo-11α,15-dihydroxy-13-trans-prostenoic acids of the table. In the instance of the alkyl esters the deblocking procedure does not result in ester hydrolysis and the product is obtained as an alkyl prostenoate ester. When both the 4-oxycyclopentenone and 1-iodo-3-triphenylmethoxy-trans-1-alkene components of these preparations are utilized in their optically resolved forms then the product will be one optical antipode inasmuch as the various conditions of this synthesis do not induce racemization. When neither of the components are in the resolved form then two racemates, the 15-"normal" and the 15-"epi", are formed. These are separable by chromatographic procedures, in the more difficult instance with high speed liquid chromatography and if necessary using the recycling technique. If either of the components are resolved then two diastereomers, rather than racemates, are formed and these are similarly separable by chromatography.

TABLE 15

| Example | Starting 4-oxy-cyclopentenone of Example | Starting 1-iodo-3--triphenylmethoxy--trans-1-alkene of Example | Product 9-oxo-11α,15-dihydroxy-13-trans-prostenoic acid or ester and 15-epi isomer thereof |
|---|---|---|---|
| 189 | 44 | 145 | 9-oxo-11α,15-dihydroxy-18,20-ethano-13-trans-prostenoic acid |
| 190 | 44 | 146 | 9-oxo-11α,15-dihydroxy-19,20-(1,3-propano)-13-trans-prostenoic acid |
| 191 | 44 | 149 | 9-oxo-11α,15-dihydroxy-16-methyl-18,20-ethano-13-trans-prostenoic acid |
| 192 | 44 | 153 | 9-oxo-11α,15-dihydroxy-17,20-ethano-13-trans-prostenoic acid |
| 193 | 44 | 181 | 9-oxo-11α,15-dihyroxy-17,20-ethano-13-trans-18-prostadienoic acid |
| 194 | 45 | 147 | 9-oxo-11α,15-dihydroxy-6,7-dinor-20,20-(1,4--butano)-13-trans-prostenoic acid |
| 195 | 45 | 184 | 9-oxo-11α,15-dihydroxy-6,7-dinor-16,20-methano-13-trans,17-prostadienoic acid |
| 196 | 44 | 172 | 9-oxo-11α,15-dihydroxy-17,18-methano-13-trans-prostenoic acid |
| 197 | 46 | 155 | 9-oxo-11α,15-dihydroxy-5,6,7-trinor-19,20-(1,4-butano)-13-trans-prostenoic acid |
| 198 | 46 | 172 | 9-oxo-11α,15-dihydroxy-5,6,7-trinor-17,18-methano-13-trans-prostenoic acid |
| 199 | 46 | 182 | 9-oxo-11α,15-dihydroxy-17,20-ethano-13-trans-19-prostadienoic acid |
| 200 | 47 | 172 | 9-oxo-11α,15-dihydroxy-7a,7b-bishomo-17,18-methano-13-trans-prostenoic acid |

TABLE 15-continued

| Example | Starting 4-oxy-cyclopentenone of Example | Starting 1-iodo-3-triphenylmethoxy-trans-1-alkene of Example | Product 9-oxo-11α,15-dihydroxy-13-trans-prostenoic acid or ester and 15-epi isomer thereof |
|---|---|---|---|
| 201 | 47 | 147 | 9-oxo-11α,15-dihydroxy-7a,7b-bishomo-20,20-(1,4-butano)-13-trans-prostenoic acid |
| 202 | 47 | 181 | 9-oxo-11α,15-dihydroxy-7a,7b-bishomo-17,20-ethano-13-trans,18-prostadienoic acid |
| 203 | 47 | 185 | 9-oxo-11α,15-dihydroxy-7a,7b-bishomo-16,20-methano-13-trans,18-prostadienoic acid |
| 204 | 48 | 180 | 9-oxo-11α,15-dihydroxy-2-ethyl-17,20-methano-13-trans,18-prostadienoic acid |
| 205 | 48 | 184 | 9-oxo-11α,15-dihydroxy-2-ethyl-16,20-methano-13-trans,17-prostadienoic acid |
| 206 | 48 | 172 | 9-oxo-11α,15-dihydroxy-2-ethyl-17,18-methano-13-trans-prostenoic acid |
| 207 | 48 | 166 | 9-oxo-11α,15-dihydroxy-2-ethyl-16,19-ethano-13-trans-prostenoic acid |
| 208 | 48 | 150 | 9-oxo-11α,15-dihydroxy-2,16-diethyl-19,20-(1,3-propano)-13-trans-prostenoic acid |
| 209 | 55 | 172 | 9-oxo-11α,15-dihydroxy-2-methyl-17,18-methano-13-trans-prostenoic acid |
| 210 | 55 | 167 | 9-oxo-11α,15-dihydroxy-2-methyl-16,20-(1,3-propano)-13-trans-prostenoic acid |
| 211 | 55 | 148 | 9-oxo-11α,15-dihydroxy-2-methyl-20-cyclopentyl-13-trans-prostenoic acid |
| 212 | 55 | 181 | 9-oxo-11α,15-dihydroxy-2-methyl-17,20-ethano-13-trans,18-prostadienoic acid |
| 213 | 49 | 182 | 9-oxo-11α,15-dihydroxy-3,3-dimethyl-17,20-ethano-13-trans,18-prostadienoic acid |
| 214 | 49 | 184 | 9-oxo-11α,15-dihydroxy-3,3-dimethyl-16,20-methano-13-trans,17-prostadienoic acid |
| 215 | 49 | 172 | 9-oxo-11α,15-dihydroxy-3,3-dimethyl-17,18-methano-13-trans-prostenoic acid |
| 216 | 49 | 165 | 9-oxo-11α,15-dihydroxy-3,3-dimethyl-16,20-methano-13-trans-prostenoic acid |
| 217 | 49 | 186 | 9-oxo-11α,15-dihydroxy-3,3,16-trimethyl-18,20-(1,3-propano)-13-trans-prostenoic acid |
| 218 | 49 | 146 | 9-oxo-11α,15-dihydroxy-3,3-dimethyl-19,20-(1,3-propano)-13-trans-prostenoic acid |
| 219 | 50 | 149 | 9-oxo-11α,15-dihydroxy-3-oxa-16-methyl-18,20-ethano-13-trans-prostenoic acid |
| 220 | 50 | 146 | 9-oxo-11α,15-dihydroxy-3-oxa-19,20-(1,3-propano)-13-trans-prostenoic acid |
| 221 | 50 | 163 | 9-oxo-11α,15-dihydroxy-3-oxa-17-methyl-20-nor-16,19-methano-13-trans-prostenoic acid |
| 222 | 50 | 172 | 9-oxo-11α,15-dihydroxy-3-oxa-17,18-methano-13-trans-prostenoic acid |
| 223 | 50 | 180 | 9-oxo-11α,15-dihydroxy-3-oxa-17,20-methano-13-trans-prostenoic acid |
| 224 | 50 | 185 | 9-oxo-11α,15-dihydroxy-3-oxa-16,20-methano-13-trans,18-prostadienoic acid |
| 225 | 51 | 181 | 9-oxo-11α,15-dihydroxy-2-fluoro-17,20-ethano-13-trans,18-prostadienoic acid |
| 226 | 51 | 172 | 9-oxo-11α,15-dihydroxy-2-fluoro-17,18-methano-13-trans-prostenoic acid |
| 227 | 51 | 162 | 9-oxo-11α,15-dihydroxy-2-fluoro-16,19-methano-20-nor-13-trans-prostenoic acid |
| 228 | 51 | 151 | 9-oxo-11α,15-dihydroxy-2-fluoro-17,20-methano-18-methyl-13-trans-prostenoic acid |
| 229 | 52 | 144 | 9-oxo-11α,15-dihydroxy-6,20-dinor-17,19-methano-13-trans-prostenoic acid |
| 230 | 52 | 149 | 9-oxo-11α,15-dihydroxy-6-nor-16-methyl-18,20-ethano-13-trans-prostenoic acid |
| 231 | 52 | 172 | 9-oxo-11α,15-dihydroxy-6-nor-17,18-methano-13-trans-prostenoic acid |
| 232 | 52 | 180 | 9-oxo-11α,15-dihydroxy-6-nor-17,20-methano-13-trans,18-prostadienoic acid |
| 233 | 52 | 185 | 9-oxo-11α,15-dihydroxy-6-nor-16,20-methano-13-trans,18-prostadienoic acid |
| 234 | 53 | 184 | 9-oxo-11α,15-dihydroxy-7-homo-16,20-methano-13-trans-17-prostadienoic acid |
| 235 | 53 | 182 | 9-oxo-11α,15-dihydroxy-7-homo-17,20-ethano-13-trans,19-prostadienoic acid |
| 236 | 53 | 172 | 9-oxo-11α,15-dihydroxy-7-homo-17,18-methano-13-trans-prostenoic acid |
| 237 | 53 | 186 | 9-oxo-11α,15-dihydroxy-7-homo-16-methyl-18,20-(1,3-propano)-13-trans-prostenoic acid |
| 238 | 54 | 172 | 9-oxo-11α,15-dihydroxy-2-phenyl-17,18-methano-13-trans-prostenoic acid |
| 239 | 54 | 164 | 9-oxo-11α,15-dihydroxy-2-phenyl-17-methyl-20-nor-16,18-ethano-13-trans-prostenoic acid |
| 240 | 54 | 167 | 9-oxo-11α,15-dihydroxy-2-phenyl-16,20-(1,3-propano)-13-trans-prostenoic acid |
| 241 | 54 | 149 | 9-oxo-11α15-dihydroxy-2-phenyl-16-methyl-18,20-ethano-13-trans-prostenoic acid |
| 242 | 54 | 155 | 9-oxo-11α,15-dihydroxy-2-phenyl-19,20-(1,4-butano)-13-trans-prostenoic acid |
| 243 | 54 | 180 | 9-oxo-11α,15-dihydroxy-2-phenyl-17,20-methano-13-trans,18-prostadienoic acid |
| 244 | 54 | 184 | 9-oxo-11α,15-dihydroxy-2-phenyl-16,20-methano-13-trans,18-prostadienoic acid |
| 245 | 56 | 183 | ethyl 9-oxo-11α,15-dihydroxy-17-methyl-17,20-ethano-13-trans-prostenoate |

TABLE 15-continued

| Example | Starting 4-oxy-cyclopentenone of Example | Starting 1-iodo-3-triphenylmethoxy--trans-1-alkene of Example | Product 9-oxo-11α,15-dihydroxy-13-trans-prostenoic acid or ester and 15-epi isomer thereof |
|---|---|---|---|
| 246 | 57 | 182 | methyl 9-oxo-11α,15-dihydroxy-17,20-ethano-13-trans,19-prostadienoate |
| 247 | 57a | 184 | 1 methyl 9-oxo-11α,15-dihydroxy-16,20-methano-13-trans,17-prostadienoate |
| 248 | 57a | 172 | 1 methyl 9-oxo-11α,15-dihydroxy-17,18-methano-13-trans-prostenoate |
| 249 | 57a | 186 | 1 methyl 9-oxo-11α,15-dihydroxy-16-methyl-18,20-(1,3-propano)-13-trans-prostenoate |
| 250 | 57a | 159 | 1 methyl 9-oxo-11α,15-dihydroxy-17,20-ethano-20-methyl-13-trans-prostenoate |
| 251 | 57b | 158 | d methyl 9-oxo-11α,15-dihydroxy-17,20-(1,4-butano)-13-trans-prostenoate |
| 252 | 57b | 150 | d methyl-11α,15-dihydroxy-16-ethyl-19,20-(1,3-propano)-13-trans-prostenoate |
| 253 | 57b | 172 | d methyl-11α,15-dihydroxy-17,18-methano-13-trans-prostenoate |
| 254 | 57b | 185 | d methyl 11α,15-dihydroxy-16,20-methano-13-trans,18-prostadienoate |
| 255 | 57b | 180 | d methyl-11α,15-dihydroxy-17,20-methano-13-trans,18-prostadienoate |
| 256 | 58 | 172 | butyl 9-oxo-11α,15-dihydroxy-17,18-methano-13-trans-prostenoate |
| 257 | 58 | 184 | butyl 9-oxo-11α,15-dihydroxy-16,20-methano-13-trans,17-prostadienoate |
| 258 | 59 | 186 | isopropyl 9-oxo-11α,15-dihydroxy-16-methyl-18,20-(1,3-propano)-13-trans-prostenoate |
| 259 | 59 | 155 | isopropyl 9-oxo-11α,15-dihydroxy-19,20-(1,4-butano)-13-trans-prostenoate |
| 260 | 60 | 151 | decyl 9-oxo-11α,15-dihydroxy-17,20-methano-18-methyl-13-trans-prostenoate |
| 261 | 60 | 172 | decyl 9-oxo-11α,15-dihydroxy-17,18-methano-13-trans-prostenoate |
| 262 | 60 | 181 | decyl 9-oxo-11α,15-dihydroxy-17,20-ethano-13-trans,18-prostadienoate |
| 263 | 97 | 143 | 9-oxo-11α,15-dihydroxy-17,20-methano-5-cis,13-trans,18-prostadienoate |
| 264 | 97 | 145 | 9-oxo-11α,15-dihydroxy-18,20-ethano-5-cis,13-trans-prostadienoic acid |
| 265 | 97 | 148 | 9-oxo-11α,15-dihydroxy-20-cyclopentyl-5-cis,13-trans-prostadienoic acid |
| 266 | 97 | 150 | 9-oxo-11α,15-dihydroxy-16-ethyl-19,20-(1,3-propano)-15-cis,13-trans-prostadienoic acid |
| 267 | 97 | 154 | 9-oxo-11α,15-dihydroxy-18,20-(1,3-propano)-5-cis,13-trans-prostadienoic acid |
| 268 | 97 | 156 | 9-oxo-11α,15-dihydroxy-17,20-(1,3-propano)-5-cis,13-trans-prostadienoic acid |
| 269 | 109 | 160 | 9-oxo-11α,15-dihydroxy-17,19-(1,3-propano)-5-cis,13-trans-prostadienoic acid |
| 270 | 97 | 172 | 9-oxo-11α,15-dihydroxy-17,18-methano-5-cis,13-trans-prostadienoic acid |
| 271 | 105 | 180 | 9-oxo-11α,15-dihydroxy-17,20-methano-5-cis,13-trans,18-prostatrienoic acid |
| 272 | 97 | 184 | 9-oxo-11α,15-dihydroxy-16,20-methano-5-cis,13-trans,17-prostatrienoic acid |
| 273 | 97A | 146 | 1 methyl 9-oxo-11α,15-dihydroxy-19,20-(1,3-propano)-4-cis,13-trans-prostadienoate |
| 274 | 97A | 149 | 1 methyl 9-oxo-11α,15-dihydroxy-16-methyl-18,20-ethano-5-cis,13-trans-prostadienoate |
| 275 | 97A | 152 | 1 methyl 9-oxo-11α,15-dihydroxy-20-methyl-19,20-(1,3-propano)-5-cis,13-trans-prostadienoate |
| 276 | 97A | 153 | 1 methyl 9-oxo-11α, 15-dihydroxy-17,20-ethano-5-cis,13-trans-prostadienoate |
| 277 | 97A | 172 | 1 methyl 9-oxo-11α,15-dihydroxy-17,18-methano-5-cis,13-trans-prostadienoate |
| 278 | 97A | 186 | 1 methyl 9-oxo-11α,15-dihydroxy-16-methyl-18,20-(1,3-propano)-5-cis,13-trans-prostadienoate |
| 279 | 97A | 157 | 1 methyl 9-oxo-11α,15-dihydroxy-20-methyl-17,20-(1,3-propano)-5-cis,13-trans-prostadienoate |
| 280 | 97A | 158 | 1 methyl 9-oxo-11α,15-dihydroxy-17,20-(1,4-butano)-5-cis,13-trans-prostadienoate |
| 281 | 97A | 159 | 1 methyl 9-oxo-11α,15-dihydroxy-17,20-ethano-20-methyl-5-cis,13-trans-prostadienoate |
| 282 | 97A | 181 | 1 methyl 9-oxo-11α,15-dihydroxy-17,20-ethano-5-cis,13-trans,18-prostatrienoate |
| 283 | 97A | 185 | 1 methyl 9-oxo-11α,15-dihydroxy-16,20-methano-5-cis,13-trans,18-prostatrienoate |
| 284 | 98 | 144 | 9-oxo-11α,15-dihydroxy-7,20-bisnor-17,19-methano-5-cis,13-trans-prostadienoic acid |
| 285 | 98 | 145 | 9-oxo-11α,15-dihydroxy-7-nor-18,20-ethano-5-cis,13-trans-prostadienoic acid |
| 286 | 98 | 149 | 9-oxo-11α,15-dihydroxy-7-nor-16-methyl-18,20-ethano-5-cis,13-trans-prostadienoic acid |
| 287 | 106 | 157 | 9-oxo-11α,15-dihydroxy-7-nor-20-methyl-17,20-(1,3-propano)-5-cis,13-trans-prostadienoic acid |
| 288 | 98 | 172 | 9-oxo-11α,15-dihydroxy-7-nor-17,18-methano-5-cis,13-trans-prostadienoic acid |
| 289 | 98 | 159 | 9-oxo-11α,15-dihydroxy-7-nor-17,20-ethano-20-methyl-5-cis,13-trans-prostadienoic acid |
| 290 | 98 | 180 | 9-oxo-11α,15-dihydroxy-7-nor-17,20-methano-5-cis,13-trans,18-prostatrienoic acid |

TABLE 15-continued

| Example | Starting 4-oxy-cyclopentenone of Example | Starting 1-iodo-3--triphenylmethoxy--trans-1-alkene of Example | Product 9-oxo-11α,15-dihydroxy-13-trans-prostenoic acid or ester and 15-epi isomer thereof |
|---|---|---|---|
| 291 | 98 | 184 | 9-oxo-11α,15-dihydroxy-7-nor-16,20-methano-5-cis,13-trans,17-prostatrienoic acid |
| 292 | 99 | 185 | 9-oxo-11α,15-dihydroxy-7a-homo-16,20-methano-5-cis,13-trans,18-prostatrienoic acid |
| 293 | 99 | 180 | 9-oxo-11α,15-dihydroxy-7a-homo-17,20-13-methano-5-cis,13-trans,18-prostatrienoic acid |
| 294 | 100 | 181 | 9-oxo-11α,15-dihydroxy-7a,7b-bis-homo-17,20-ethano-5-cis,13-trans,18-prostatrienoic acid |
| 295 | 100 | 184 | 9-oxo-11α,15-dihydroxy-7a,7b-bis-homo-16,20-methano-5-cis,13-trans,17-prostatrienoic acid |
| 296 | 99 | 172 | 9-oxo-11α,15-dihydroxy-7a-homo-17,18-methano-5-cis,13-trans-prostadienoic acid |
| 297 | 99 | 186 | 9-oxo-11α,15-dihydroxy-7a-homo-16-methyl-18,20-(1,3-propano)-5-cis,13-trans-prostadienoic acid |
| 298 | 99 | 146 | 9-oxo-11α,15-dihydroxy-7a-homo-19,20-(1,3-propano)-5-cis,13-trans-prostadienoic acid |
| 299 | 99 | 160 | 9-oxo-11α,15-dihydroxy-7a-homo-17,19-(1,3-propano)-5-cis,13-trans-prostadienoic acid |
| 300 | 100 | 172 | 9-oxo-11α,15-dihydroxy-7a,7b-bishomo-17,18-methano-5-cis,13-trans-prostadienoic acid |
| 301 | 100 | 183 | 9-oxo-11α,15-dihydroxy-7a,7b-bishomo-17-methyl-17,20-ethano-5-cis,13-trans-prostadienoic acid |
| 302 | 100 | 149 | 9-oxo-11α,15-dihydroxy-7a,7b-bishomo-16-methyl-18,20-ethano-5-cis,13-trans-prostadienoic acid |
| 303 | 100 | 148 | 9-oxo-11α,15-dihydroxy-7a,7b-bishomo-20-cyclopentyl-5-cis-13-trans-prostadienoic acid |
| 304 | 100 | 159 | 9-oxo-11α,15-dihydroxy-7a,7b-bishomo-17,20-ethano-20-methyl-5-cis,13-trans-prostadienoic acid |
| 305 | 101 | 145 | 9-oxo-11α,15-dihydroxy-4-methyl-18,20-ethano-5-cis,13-trans-prostadienoic acid |
| 306 | 101 | 149 | 9-oxo-11α,15-dihydroxy-4,16-dimethyl-18,20-ethano-5-cis,13-trans-prostadienoic acid |
| 307 | 101 | 154 | 9-oxo-11α,15-dihydroxy-4-methyl-18,20-(1,3-propano)-5-cis,13-trans-prostadienoic acid |
| 308 | 101 | 166 | 9-oxo-11α,15-dihydroxy-4-methyl-16,19-ethano-5-cis,13-trans-prostadienoic acid |
| 309 | 101 | 172 | 9-oxo-11α,15-dihyroxy-4-methyl-17,18-methano-5-cis,13-trans-prostadienoic acid |
| 310 | 101 | 180 | 9-oxo-11α,15-dihydroxy-4-methyl-17,20-methano-5-cis,13-trans,18-prostatrienoic acid |
| 311 | 101 | 185 | 9-oxo-11α,15-dihydroxy-4-methyl-16,20-methano-5-cis-13-trans,18-prostatrienoic acid |
| 312 | 102 | 184 | 9-oxo-11α,15-dihydroxy-4(R)-methyl-16,20-methano-5-cis,13-trans,17-prostatrienoic acid |
| 313 | 102 | 182 | 9-oxo-11α,15-dihydroxy-4(R)-methyl-17,20-ethano-5-cis,13-trans,19-prostatrienoic acid |
| 314 | 102 | 172 | 9-oxo-11α,15-dihydroxy-4(R)-methyl-17,18-methano-5-cis,13-trans-prostadienoic acid |
| 315 | 102 | 186 | 9-oxo-11α,15-dihydroxy-4(R),16-dimethyl-18,20-(1,3-propano)-5-cis,13-trans-prostadienoic acid |
| 316 | 102 | 161 | 9-oxo-11α,15-dihydroxy-4(R)-methyl-16,20-ethano-5-cis,13-trans-prostadienoic acid |
| 317 | 102 | 146 | 9-oxo-11α,15-dihydroxy-4(R)-methyl-19,20-(1,3-propano)-5-cis,13-trans-prostadienoic acid |
| 318 | 102 | 164 | 9-oxo-11α,15-dihydroxy-4(R),17-dimethyl-20-nor-16,18-ethano-5-cis,13-trans-prostadienoic acid |
| 319 | 103 | 147 | 9-oxo-11α,15-dihydroxy-4-ethyl-20,20-(1,4-butano)-5-cis,13-trans-prostadienoic acid |
| 320 | 103 | 151 | 9-oxo-11α,15-dihydroxy-4-ethyl-17,20-methano-18-methyl-5-cis,13-trans-prostadienoic acid |
| 321 | 103 | 153 | 9-oxo-11α,15-dihydroxy-4-ethyl-17,20-ethano-5-cis,13-trans-prostadienoic acid |
| 322 | 103 | 167 | 9-oxo-11α,15-dihydroxy-4-ethyl-16,20-(1,3-propano)-5-cis,13-trans-prostadienoic acid |
| 323 | 103 | 172 | 9-oxo-11α,15-dihydroxy-4-ethyl-17,18-methano-5-cis,13-trans-prostadienoic acid |
| 324 | 103 | 181 | 9-oxo-11α,15-dihydroxy-4-ethyl-17,20-ethano-5-cis,13-trans,18-prostatrienoic acid |
| 325 | 103 | 185 | 9-oxo-11α,15-dihydroxy-4-ethyl-16,20-methano-5-cis,13-trans,18-prostatrienoic acid |
| 326 | 104 | 184 | 9-oxo-11α,15-dihydroxy-4-propyl-16,20-methano-5-cis,13-trans,17-prostatrienoic acid |
| 327 | 104 | 180 | 9-oxo-11α,15-dihydroxy-4-propyl-17,20-methano-5-cis,13-trans,18-prostatrienoic acid |
| 328 | 104 | 172 | 9-oxo-11α,15-dihydroxy-4-propyl-17,18-methano-5-cis,13-trans-prostadienoic acid |
| 329 | 104 | 145 | 9-oxo-11α,15-dihydroxy-4-propyl-18,20-ethano-5-cis,13-trans-prostadienoic acid |
| 330 | 104 | 186 | 9-oxo-11α,15-dihydroxy-4-propyl-16-methyl-18,20-(1,3-propano)-5-cis,13-trans-prostadienoic acid |
| 331 | 104 | 148 | 9-oxo-11α,15-dihydroxy-4-propyl-20-cyclopentyl-5-cis,13-trans-prostadienoic acid |
| 332 | 104 | 152 | 9-oxo-11α,15-dihydroxy-4-propyl-20-methyl-19,20-(1,3-propano)-5-cis,13-trans-prostadienoic acid |
| 333 | 104 | 164 | 9-oxo-11α,15-dihydroxy-4-propyl-17-methyl-20- |

TABLE 15-continued

| Example | Starting 4-oxy-cyclopentenone of Example | Starting 1-iodo-3-triphenylmethoxy-trans-1-alkene of Example | Product 9-oxo-11α,15-dihydroxy-13-trans-prostenoic acid or ester and 15-epi isomer thereof |
|---|---|---|---|
| | | | nor-16,18-ethano-5-cis,13-trans-prostadienoic acid |
| 334 | 104 | 165 | 9-oxo-11α,15-dihydroxy-4-propyl-16,20-methano-5-cis,13-trans-prostadienoic acid |
| 335 | 104 | 156 | 9-oxo-11α,15-dihydroxy-4-propyl-17,20-(1,3-propano)-5-cis,13-trans-prostadienoic acid |
| 336 | 104 | 161 | 9-oxo-11α,15-dihydroxy-4-propyl-16,20-ethano-5-cis,13-trans-prostadienoic acid |

EXAMPLE 337

Preparation of 9α,11α,15-trihydroxy-17,20-methano-13-trans-prostenoic acid

To a solution of 433 mg. of 9-oxo-11α,15α-dihydroxy-17,20-methano-13-trans-prostenoic acid (Example 187) in 4.5 ml. of tetrahydrofuran, stirred in an ice bath under nitrogen atmosphere, is added dropwise 3.7 ml. of 0.76M lithium perhydro-9b-boraphenalyl hydride. After 40 minutes at 0° C. there is added 1.62 ml. of 3N sodium hydroxide followed by 1.62 ml. of 30% hydrogen peroxide. Ether is added and the resulting solution is acidified with 2N hydrochloric acid. The ether layer is washed several times with saturated sodium chloride solution, dried with anhydrous magnesium sulfate and then to dryness to give the subject product as an oil.

EXAMPLES 338 – 485

Treatment of the 9-oxo derivatives designated in Table 16 below with lithium perhydro-9b-boraphenalyl hydride by the procedure described in Example 337 provides the 9α,11α, 15-trihydroxy derivatives of the table.

TABLE 16

| Example | Starting 9-oxo derivative of Example | Product 9α-hydroxy derivative and 15-epi isomer thereof |
|---|---|---|
| 338 | 189 | 9α,11α,15-trihydroxy-18,20-ethano-13-trans-prostenoic acid |
| 339 | 190 | 9α,11α,15-trihydroxy-19,20-(1,3-propano)-13-trans-prostenoic acid |
| 340 | 191 | 9α,11α,15-trihydroxy-16-methyl-18,20-ethano-13-trans-prostenoic acid |
| 341 | 192 | 9α,11α,15-trihydroxy-17,20-ethano-13-trans-prostenoic acid |
| 342 | 193 | 9α,11α,15-trihydroxy-17,20-ethano-13-trans,18-prostadienoic acid |
| 343 | 194 | 9α,11α,15-trihydroxy-6,7-dinor-20,20-(1,4-butano)-13-trans-prostenoic acid |
| 344 | 195 | 9α,11α,15-trihydroxy-6,7-dinor-16,20-methano-13-trans,17-prostadienoic acid |
| 345 | 196 | 9α,11α,15-trihydroxy-17,18-methano-13-trans-prostadienoic acid |
| 346 | 197 | 9α,11α,15-trihydroxy-5,6,7-trinor-19,20-(1,4-butano)-13-trans-prostenoic acid |
| 347 | 198 | 9α,11α,15-trihydroxy-5,6,7-trinor-17,18-methano-13-trans-prostenoic acid |
| 348 | 199 | 9α,11α,15-trihydroxy-17,20-ethano-13-trans,19-prostadienoic acid |
| 349 | 200 | 9α,11α,15-trihydroxy-7a,7b-bishomo-17,18-methano-13-trans-prostenoic acid |
| 350 | 201 | 9α,11α,15-trihydroxy-7a,7b-bishomo-20,20-(1,4-butano)-13-trans-prostenoic acid |
| 351 | 202 | 9α,11α,15-trihydroxy-7a,7b-bishomo-17,20-ethano-13-trans,18-prostadienoic acid |
| 352 | 203 | 9α,11α,15-trihydroxy-7a,7b-bishomo-16,20-methano-13-trans,18-prostadienoic acid |
| 353 | 204 | 9α,11α,15-trihydroxy-2-ethyl-17,20-methano-13-trans,18-prostadienoic acid |
| 354 | 205 | 9α,11α,15-trihydroxy-2-ethyl-16,20-methano-13-trans,17-prostadienoic acid |
| 355 | 206 | 9α,11α,15-trihydroxy-2-ethyl-17,18-methano-13-trans-prostenoic acid |
| 356 | 207 | 9α,11α,15-trihydroxy-2-ethyl-16,19-ethano-13-trans-prostenoic acid |
| 357 | 208 | 9α,11α,15-trihydroxy-2,16-diethyl-19,20-(1,3-propano)-13-trans-prostenoic acid |
| 358 | 209 | 9α,11α,15-trihydroxy-2-methyl-17,18-methano-13-trans-prostenoic acid |
| 359 | 210 | 9α,11α,15-trihydroxy-2-methyl-16,20-(1,3-propano)-13-trans-prostenoic acid |
| 360 | 211 | 9α,11α,15-trihydroxy-2-methyl-20-cyclopentyl-13-trans-prostenoic acid |
| 361 | 212 | 9α,11α,15-trihydroxy-2-methyl-17,20-ethano-13-trans,18-prostadienoic acid |
| 362 | 213 | 9α,11α,15-trihydroxy-3,3-dimethyl-17,20-ethano-13-trans,18-prostadienoic acid |
| 363 | 214 | 9α,11α,15-trihydroxy-3,3-dimethyl-16,20-methano-13-trans,17-prostadienoic acid |
| 364 | 215 | 9α,11α,15-trihydroxy-3,3-dimethyl-17,18-methano-13-trans-prostenoic acid |
| 365 | 216 | 9α,11α,15-trihydroxy-3,3-dimethyl-16,20-methano-13-trans-prostenoic acid |

TABLE 16-continued

| Example | Starting 9-oxo derivative of Example | Product 9α-hydroxy derivative and 15-epi isomer thereof |
|---|---|---|
| 366 | 217 | 9α,11α,15-trihydroxy-3,3,16-trimethyl-18,20-(1,3-propano)-13-trans-prostenoic acid |
| 367 | 218 | 9α,11α,15-trihydroxy-3,3-dimethyl-19,20-(1,3-propano)-13-trans-prostenoic acid |
| 368 | 219 | 9α,11α,15-trihydroxy-3-oxa-16-methyl-18,20-ethano-13-trans-prostenoic acid |
| 369 | 220 | 9α,11α,15-trihydroxy-3-oxa-19,20-(1,3-propano)-13-trans-prostenoic acid |
| 370 | 221 | 9α,11α,15-trihydroxy-3-oxa-17-methyl-20-nor-16,19-methano-13-trans-prostenoic acid |
| 371 | 222 | 9α,11α,15-trihydroxy-3-oxa-17,18-methano-13-trans-prostenoic acid |
| 372 | 223 | 9α,11α,15-trihydroxy-3-oxa-17,20-methano-13-trans-prostenoic acid |
| 373 | 224 | 9α,11α,15-trihydroxy-3-oxa-16,20-methano-13-trans,18-prostadienoic acid |
| 374 | 225 | 9α,11α,15-trihydroxy-2-fluoro-17,20-ethano-13-trans,18-prostadienoic acid |
| 375 | 226 | 9α,11α,15-trihydroxy-2-fluoro-17,18-methano-13-trans-prostenoic acid |
| 376 | 227 | 9α,11α,15-trihydroxy-2-fluoro-16,19-methano-20-nor-13-trans-prostenoic acid |
| 377 | 228 | 9α,11α,15-trihydroxy-2-fluoro-17,20-methano-18-methyl-13-trans-prostenoic acid |
| 378 | 229 | 9α,11α,15-trihydroxy-6,20-dinor-17,19-methano-13-trans-prostenoic acid |
| 379 | 230 | 9α,11α,15-trihydroxy-6-nor-16-methyl-18,20-ethano-13-trans-prostenoic acid |
| 380 | 231 | 9α,11α,15-trihydroxy-6-nor-17,18-methano-13-trans-prostenoic acid |
| 381 | 232 | 9α,11α,15-trihydroxy-6-nor-17,20-methano-13-trans,18-prostadienoic acid |
| 382 | 233 | 9α,11α,15-trihydroxy-6-nor-16,20-methano-13-trans,18-prostadienoic acid |
| 383 | 234 | 9α,11α,15-trihydroxy-7-homo-16,20-methano-13-trans,17-prostadienoic acid |
| 384 | 235 | 9α,11α,15-trihydroxy-7-homo-17,20-ethano-13-trans,19-prostadienoic acid |
| 385 | 236 | 9α,11α,15-trihydroxy-7-homo-17,18-methano-13-trans-prostenoic acid |
| 386 | 237 | 9α,11α,15-trihydroxy-7-homo-16-methyl-18,20-(1,3-propano)-13-trans-prostenoic acid |
| 387 | 238 | 9α,11α,15-trihydroy-2-phenyl-17,18-methano-13-trans-prostenoic acid |
| 388 | 239 | 9α,11α,15-trihydroxy-2-phenyl-17-methyl-20-nor-16,18-ethano-13-trans-prostenoic acid |
| 389 | 240 | 9α,11α,15-trihydroxy-2-phenyl-16,20-(1,3-propano-13-trans-prostenoic acid |
| 390 | 241 | 9α,11α,15-trihydroxy-2-phenyl-16-methyl-18,20-ethano-13-trans-prostenoic acid |
| 391 | 242 | 9α,11α,15-trihydroxy-2-phenyl-19,20-(1,4-butano)-13-trans-prostenoic acid |
| 392 | 243 | 9α,11α,15-trihydroxy-2-phenyl-17,20-methano-13-trans,18-prostadienoic acid |
| 393 | 244 | 9α,11α,15-trihydroxy-2-phenyl-16,20-methano-13-trans,18-prostadienoic acid |
| 394 | 244 | ethyl 9α,11α,15-trihydroxy-17-methyl-17,20-ethano-13-trans-prostenoate |
| 395 | 246 | methyl 9α,11α,15-trihydroxy-17,20-ethano-13-trans,19-prostadienoate |
| 396 | 247 | 1 methyl 9α,11α,15-trihydroxy-16,20-methano-13-trans,17-prostadienoate |
| 397 | 248 | 1 methyl 9α,11α,15-trihydroxy-17,18-methano-13-trans-prostenoate |
| 398 | 249 | 1 methyl 9α,11α,15-trihydroxy-16-methyl-18,20-(1,3-propano)-13-trans-prostenoate |
| 399 | 250 | 1 methyl 9α,11α,15-trihydroxy-17,20-ethano-20-methyl-13-trans-prostenoate |
| 400 | 251 | d methyl 9α,11α,15-trihydroxy-17,20-(1,4-butano)-13-trans-prostenoate |
| 401 | 252 | d methyl 9α,11α,15-trihydroxy-16-ethyl-19,20 (1,3-propano)-13-trans-prostenoate |
| 402 | 253 | d methyl 9α,11α,15-trihydroxy-17,18-methano-13-trans-prostenoate |
| 403 | 254 | d methyl 9α,11α,15-trihydroxy-16,20-methano-13-trans,18-prostadienoate |
| 404 | 255 | d methyl 9α,11α,15-trihydroxy-17,20-methano-13-trans,18-prostadienoate |
| 405 | 256 | butyl 9α,11α,15-trihydroxy-17,18-methano-13-trans-prostenoate |
| 406 | 257 | butyl 9α,11α,15-trihydroxy-16,20-methano-13-trans,17-prostadienoate |
| 407 | 258 | isopropyl 9α,11α,15-trihydroxy-16-methyl-18,20-(1,3-propano)-13-trans-prostenoate |
| 408 | 259 | isopropyl 9α,11α,15-trihydroxy-19,20-(1,4-butano)-13-trans-prostenoate |
| 409 | 260 | decyl 9α,11α,15-trihydroxy-17,20-methano-18-methyl-13-trans-prostenoate |
| 410 | 261 | decyl 9α,11α,15-trihydroxy-17,18-methano-13-trans-prostenoate |
| 411 | 262 | decyl 9α,11α,15-trihydroxy-17,20-ethano-13-trans,18-prostadienoate |

TABLE 16-continued

| Example | Starting 9-oxo derivative of Example | Product 9α-hydroxy derivative and 15-epi isomer thereof |
|---|---|---|
| 412 | 263 | 9α,11α,15-trihydroxy-17,20-methano-5-cis,13-trans-prostadienoic acid |
| 413 | 264 | 9α,11α,15-trihydroxy-18,20-ethano-5-cis,13-trans-prostadienoic acid |
| 414 | 265 | 9α,11α,15-trihydroxy-20-cyclopentyl-5-cis,13-trans-prostadienoic acid |
| 415 | 266 | 9α,11α,15-trihydroxy-16-ethyl-19,20-(1,3-propano)-5-cis,13-trans-prostadienoic acid |
| 416 | 267 | 9α,11α,15-trihydroxy-18,20-(1,3-propano)-5,cis,13-trans-prostadienoic acid |
| 417 | 268 | 9α,11α,15-trihydroxy-17,20-(1,3-propano)-5-cis,13-trans-prostadienoic acid |
| 418 | 269 | 9α,11α,15-trihydroxy-17,19-(1,3-propano)-5-cis,-trans-prostadienoic acid |
| 419 | 270 | 9α,11α,15-trihydroxy-17,18-methano-5-cis,13-trans-prostadienoic acid |
| 420 | 271 | 9α,11α,15-trihydroxy-17,20-methano-5-cis,13-trans,18-prostatrienoic acid |
| 421 | 272 | 9α,11α,15-trihydroxy-16,20-methano-5-cis,13-trans,17-prostatrienoic acid |
| 422 | 273 | 1 methyl 9α,11α,15-trihydroxy-19,20-(1,3-propano)-5-cis,13-trans-prostadienoate |
| 423 | 274 | 1 methyl 9α,11α,15-trihydroxy-16-methyl-18,20-ethano-5-cis,13-trans-prostadienoate |
| 424 | 275 | 1 methyl 9α,11α,15-trihydroxy-20-methyl-19,20-(1,3-propano)-5-cis,13-trans-prostadienoate |
| 425 | 276 | 1 methyl 9α,11α,15-trihydroxy-17,20-ethano-5-cis,13-trans-prostadienoate |
| 426 | 277 | 1 methyl 9α,11α,15-trihydroxy-17,18-methano-5-cis,13-trans-prostadienoate |
| 427 | 278 | 1 methyl 9α,11α,15-trihydroxy-16-methyl-18,20-(1,3-propano)-5-cis,13-trans-prostadienoate |
| 428 | 279 | 1 methyl 9α,11α,15-trihydroxy-20-methyl-17,20-(1,3-propano)-5-cis,13-trans-prostadienoate |
| 429 | 280 | 1 methyl 9α,11α,15-trihydroxy-17,20-(1,4-butano)-5-cis,13-trans-prostadienoate |
| 430 | 281 | 1 methyl 9α,11α,15-trihydroxy-17,20-ethano-20-methyl-5-cis,13-trans-prostadienoate |
| 431 | 282 | 1 methyl 9α,11α,15-trihydroxy-17,20-ethano-5-cis,13-trans,18-prostatrienoate |
| 432 | 283 | 1 methyl 9α,11α,15-trihydroxy-16,20-methano-5-cis,13-trans,18-prostatrienoate |
| 433 | 284 | 9α,11α,15-trihydroxy-7,20-bisnor-17,19-methano-5-cis,13-trans-prostadienoic acid |
| 434 | 285 | 9α,11α,15-trihydroxy-7-nor-18,20-ethano-5-cis,13-trans-prostadienoic acid |
| 435 | 286 | 9α,11α,15-trihydroxy-7-nor-16-methyl-18,20-ethano-5-cis,13-trans-prostadienoic acid |
| 436 | 287 | 9α,11α,15-trihydroxy-7-nor-20-methyl-17,20-(1,3-propano)-5-cis,13-trans-prostadienoic acid |
| 437 | 288 | 9α,11α,15-trihydroxy-7-nor-17,18-methano-5-cis,13-trans-prostadienoic acid |
| 438 | 289 | 9α,11α,15-trihydroxy-7-nor-17,20-ethano-20-methyl-5-cis,13-trans-prostadienoic acid |
| 439 | 290 | 9α,11α,15-trihydroxy-7-nor-17,20-methano-5-cis,13-trans,18-prostatrienoic acid |
| 440 | 291 | 9α,11α,15-trihydroxy-7-nor-16,20-methano-5-cis,13-trans,17-prostatrienoic acid |
| 441 | 292 | 9α,11α,15-trihydroxy-7a-homo-16,20-methano-5-cis,13-trans,18-prostatrienoic acid |
| 442 | 293 | 9α,11α,15-trihydroxy-7a-homo-17,20-methano-5-cis,13-trans,18-prostatrienoic acid |
| 443 | 294 | 9α,11α,15-trihydroxy-7a,7b-bis-homo-17,20-ethano-5-cis,13-trans,18-prostatrienoic acid |
| 444 | 295 | 9α,11α,15-trihydroxy-7a,7b-bis-homo-16,20-methano-5-cis,13-trans,17-prostatrienoic acid |
| 445 | 296 | 9α,11α,15-trihydroxy-7a-homo-17,18-methano-5-cis,13-trans-prostadienoic acid |
| 446 | 297 | 9α,11α,15-trihydroxy-7a-homo-16-methyl-18,20-(1,3-propano)-5-cis,13-trans-prostadienoic acid |
| 447 | 298 | 9α,11α,15-trihydroxy-7a-homo-19,20-(1,3-propano)-5-cis,13-trans-prostadienoic acid |
| 448 | 299 | 9α,11α,15-trihydroxy-7a-homo-17,19-(1,3-propano)-5-cis,13-trans-prostadienoic acid |
| 449 | 300 | 9α,11α,15-trihydroxy-7a,7b-bishomo-17,18-methano-5-cis,13-trans-prostadienoic acid |
| 450 | 301 | 9α,11α,15-trihydroxy-7a,7b-bishomo-17-methyl-17,20-ethano-5-cis,13-trans-prostadienoic acid |
| 451 | 302 | 9α,11α,15-trihydroxy-7a,7b-bishomo-16-methyl-18,20-ethano-5-cis,13-trans-prostadienoic acid |
| 452 | 303 | 9α,11α,15-trihydroxy-7a,7b-bishomo-20-cyclopentyl-5-cis,13-trans-prostadienoic acid |
| 453 | 304 | 9α,11α,15-trihydroxy-7a,7b-bishomo-17,20-ethano-20-methyl-5-cis,13-trans-prostadienoic acid |
| 454 | 305 | 9α,11α,15-trihydroxy-4-methyl-18,20-ethano-5-cis,13-trans-prostadienoic acid |
| 455 | 306 | 9α,11α,15-trihydroxy-4,16-dimethyl-18,20-ethano-5-cis,13-trans-prostadienoic acid |
| 456 | 307 | 9α,11α,15-trihydroxy-4-methyl-18,20-(1,3-propano)-5-cis,13-trans-prostadienoic acid |
| 457 | 308 | 9α,11α,15-trihydroxy-4-methyl-16,19-ethano-5-cis,13-trans-prostadienoic acid |

TABLE 16-continued

| Example | Starting 9-oxo derivative of Example | Product 9α-hydroxy derivative and 15-epi isomer thereof |
|---|---|---|
| 458 | 309 | 9α,11α,15-trihydroxy-4-methyl-17,18-methano-5-cis,13-trans-prostadienoic acid |
| 459 | 310 | 9α,11α,15-trihydroxy-4-methyl-17,20-methano-5-cis,13-trans,18-prostatrienoic acid |
| 460 | 311 | 9α,11α,15-trihydroxy-4-methyl-16,20-methano-5-cis,13-trans,18-prostatrienoic acid |
| 461 | 312 | 9α,11α,15-trihydroxy-4(R)-methyl-16,20-methano-5-cis,13-trans,17-prostatrienoic acid |
| 462 | 313 | 9α,11α,15-trihydroxy-4(R)-methyl-17,20-ethano-5-cis,13-trans,19-prostatrienoic acid |
| 463 | 314 | 9α,11α,15-trihydroxy-4(R)-methyl-17,18-methano-5-cis,13-trans-prostadienoic acid |
| 464 | 315 | 9α,11α,15-trihydroxy-4(R),16-dimethyl-18,20-(1,3-propano)-5-cis,13-trans-prostadienoic acid |
| 465 | 316 | 9α,11α,15-trihydroxy-4(R)-methyl-16,20-ethano-5-cis,13-trans-prostadienoic acid |
| 466 | 317 | 9α,11α,15-trihydroxy-4(R)-methyl-19,20-(1,3-propano)-5-cis,13-trans-prostadienoic acid |
| 467 | 318 | 9α,11α,15-trihydroxy-4(R),17-dimethyl-20-nor-16,18-ethano-5-cis,13-trans-prostadienoic acid |
| 468 | 319 | 9α,11α,15-trihydroxy-4-ethyl-20,20-(1,4-butano)-5-cis,13-trans-prostadienoic acid |
| 469 | 320 | 9α,11α,15-trihydroxy-4-ethyl-17,20-methano-18-methyl-5-cis,13-trans-prostadienoic acid |
| 470 | 321 | 9α,11α,15-trihydroxy-4-ethyl-17,20-ethano-5-cis,13-trans-prostadienoic acid |
| 471 | 322 | 9α,11α,15-trihydroxy-4-ethyl-16,20-(1,3-propano)-5-cis,13-trans-prostadienoic acid |
| 472 | 323 | 9α,11α,15-trihydroxy-4-ethyl-17,18-methano-5-cis,13-trans-prostadienoic acid |
| 473 | 324 | 9α,11α,15-trihydroxy-4-ethyl-17,20-ethano-5-cis,13-trans,18-prostatrienoic acid |
| 474 | 325 | 9α,11α,15-trihydroxy-4-ethyl-16,20-ethano-5-cis,13-trans,18-prostatrienoic acid |
| 475 | 326 | 9α,11α,15-trihydroxy-4-propyl-16,20-methano-5-cis,13-trans,17-prostatrienoic acid |
| 476 | 327 | 9α,11α,15-trihydroxy-4-propyl-17,20-methano-5-cis,13-trans,18-prostatrienoic acid |
| 477 | 328 | 9α,11α,15-trihydroxy-4-propyl-17,18-methano-5-cis,13-trans-prostadienoic acid |
| 478 | 329 | 9α,11α,15-trihydroxy-4-propyl-18,20-ethano-5-cis,13-trans-prostadienoic acid |
| 479 | 330 | 9α,11α,15-trihydroxy-4-propyl-16-methyl-18,20-(1,3-propano)-5-cis,13-trans-prostadienoic acid |
| 480 | 331 | 9α,11α,15-trihydroxy-4-propyl-20-cyclopentyl-5-cis,13-trans-prostadienoic acid |
| 481 | 332 | 9α,11α,15-trihydroxy-4-propyl-20-methyl-19,20-(1,3-propano)-5-cis,13-trans-prostadienoic acid |
| 482 | 333 | 9α,11α,15-trihydroxy-4-propyl-17-methyl-20-nor-16,18-ethano-5-cis,13-trans-prostadienoic acid |
| 483 | 334 | 9α,11α,15-trihydroxy-4-propyl-16,20-methano-5-cis,13-trans-prostadienoic acid |
| 484 | 335 | 9α,11α,15-trihydroxy-4-propyl-17,20-(1,3-propano)-5-cis,13-trans-prostadienoic acid |
| 485 | 336 | 9α,11α,15-trihydroxy-4-propyl-16,20-ethano-5-cis,13-trans-prostadienoic acid |

EXAMPLE 486

9-Oxo-15-hydroxy-17,20-methano-10,13-trans-prostadienoic acid

A solution of 50 mg. of 9-oxo-11α,15-dihydroxy-17,20-methano-13-trans-prostenoic acid (Example 187) in 1 ml. of 1.5N hydrochloric acid and 2 ml. of tetrahydrofuran is stirred at ambient temperature for 70 hours. The solution is diluted with 6 ml. of saturated sodium chloride solution and extracted several times with ether. The combined ether extracts are washed with saturated sodium chloride solution, dried over anhydrous magnesium sulfate and taken to dryness under reduced pressure to give 50 mg. of the subject compound as an oil; tlc $R_f$ 0.62 on silica gel plate, ethyl acetate-acetone-acetic acid (90:20:1) development.

EXAMPLES 487 – 634

Treatment of the starting 9-oxo-11α-hydroxy derivative listed in Table 17 below with dilute hydrochloric acid at ambient temperatures by the procedure described in Example 486 gives the product 9-oxo-$\Delta^{10(11)}$ derivative of the table.

TABLE 17

| Example | Starting 11α-hydroxy-9-oxo derivative of Example | 9-oxo-$\Delta^{10(11)}$- derivative and 15-epi isomers thereof |
|---|---|---|
| 487 | 189 | 9-oxo-15-hydroxy-18,20-ethano-10,13-trans-prostadienoic acid |
| 488 | 190 | 9-oxo-15-hydroxy-19,20-(1,3-propano)-10,13-trans-prostadienoic acid |
| 489 | 191 | 9-oxo-15-hydroxy-16-methyl-18,20-ethano-10,13-trans-prostadienoic acid |
| 490 | 192 | 9-oxo-15-hydroxy-17,20-ethano-10,13-trans-prostadienoic acid |
| 491 | 193 | 9-oxo-15-hydroxy-17,20-ethano-10,13-trans,18-prostatrienoic acid |
| 492 | 194 | 9-oxo-15-hydroxy-6,7-dinor-20,20-(1,4-butano)-10,13-trans-prostadienoic acid |

TABLE 17-continued

| Example | Starting 11α-hydroxy-9-oxo derivative of Example | 9-oxo-Δ$^{10(11)}$- derivative and 15-epi isomers thereof |
|---|---|---|
| 493 | 195 | 9-oxo-15-hydroxy-6,7-dinor-16,20-methano-10,13-trans,17-prostatrienoic acid |
| 494 | 196 | 9-oxo-15-hydroxy-17,18-methano-10,13-trans-prostadienoic acid |
| 503 | 205 | 9-oxo-15-hydroxy-2-ethyl-16,20-methano-10,13-trans,17-prostatrienoic acid |
| 504 | 206 | 9-oxo-15-hydroxy-2-ethyl-17,18-methano-10,13-trans-prostadienoic acid |
| 505 | 207 | 9-oxo-15-hydroxy-2-ethyl-16,19-ethano-10,13-trans-prostadienoic acid |
| 506 | 208 | 9-oxo-15-hydroxy-2,16-diethyl-19,20-(1,3-propano)-10,13-trans-prostadienoic acid |
| 507 | 209 | 9-oxo-15-hydroxy-2-methyl-17,18-methano-10,13-trans-prostadienoic acid |
| 508 | 210 | 9-oxo-15-hydroxy-2-methyl-16,20-(1,3-propano)-10,13-trans-prostadienoic acid |
| 509 | 211 | 9-oxo-15-hydroxy-2-methyl-20-cyclopentyl-10,13-trans-prostadienoic acid |
| 510 | 212 | 9-oxo-15-hydroxy-2-methyl-17,20-ethano-10,13-trans,18-prostatrienoic acid |
| 495 | 197 | 9-oxo-15-hydroxy-5,6,7-trinor-19,20-(1,4-butano)-10,13-trans-prostadienoic acid |
| 496 | 198 | 9-oxo-15-hydroxy-5,6,7-trinor-17,18-methano-10,13-trans-prostadienoic acid |
| 497 | 199 | 9-oxo-15-hydroxy-5,6,7-trinor-17,20-ethano-10,13-trans,19-prostatrienoic acid |
| 498 | 200 | 9-oxo-15-hydroxy-7a,7b-bishomo-17,18-methano-10,13-trans-prostadienoic acid |
| 499 | 201 | 9-oxo-15-hydroxy-7a,7b-bishomo-20,20-(1,4-butano)-10,13-trans-prostadienoic acid |
| 500 | 202 | 9-oxo-15-hydroxy-7a,7b-bishomo-17,20-ethano-10,13-trans,18-prostatrienoic acid |
| 501 | 203 | 9-oxo-15-hydroxy-7a,7b-bishomo-16,20-methano-10,13-trans,18-prostatrienoic acid |
| 502 | 204 | 9-oxo-15-hydroxy-2-ethyl-17,20-methano-10,13-trans,18-prostatrienoic acid |
| 511 | 213 | 9-oxo-15-hydroxy-3,3-dimethyl-17,20-ethano-10,13-trans,18-prostatrienoic acid |
| 512 | 214 | 9-oxo-15-hydroxy-3,3-dimethyl-16,20-methano-10,13-trans,17-prostatrienoic acid |
| 513 | 215 | 9-oxo-15-hydroxy-3,3-dimethyl-17,18-methano-10,13-trans-prostadienoic acid |
| 514 | 216 | 9-oxo-15-hydroxy-3,3-dimethyl-16,20-methano-10,13-trans-prostadienoic acid |
| 515 | 217 | 9-oxo-15-hydroxy-3,3,16-trimethyl-18,20-(1,3-propano)-10,13-trans-prostadienoic acid |
| 516 | 218 | 9-oxo-15-hydroxy-3,3-dimethyl-19,20-(1,3-propano)-10,13-trans-prostadienoic acid |
| 517 | 219 | 9-oxo-15-hydroxy-3-oxa-16-methyl-18,20-ethano-10,13-trans-prostadienoic acid |
| 518 | 220 | 9-oxo-hydroxy-3-oxa-19,20-(1,3-propano)-10,13-trans-prostadienoic acid |
| 519 | 221 | 9-oxo-15-hydroxy-3-oxa-17-methyl-20-nor-16,19-methano-10,13-trans-prostadienoic acid |
| 520 | 222 | 9-oxo-15-hydroxy-3-oxa-17,18-methano-10,13-trans-prostadienoic acid |
| 521 | 223 | 9-oxo-15-hydroxy-3-oxa-17,20-methano-10,13-trans-18-prostatrienoic acid |
| 522 | 224 | 9-oxo-15-hydroxy-3-oxa-16,20-methano-10,13-trans,18-prostatrienoic acid |
| 523 | 225 | 9-oxo-15-hydroxy-2-fluoro-17,20-ethano-10,13-trans,18-prostatrienoic acid |
| 524 | 226 | 9-oxo-15-hydroxy-2-fluoro-17,17-methano-10,13-trans-prostadienoic acid |
| 525 | 227 | 9-oxo-15-hydroxy-2-fluoro-16,19-methano-20-nor-13-trans-prostadienoic acid |
| 526 | 228 | 9-oxo-15-hydroxy-2-fluoro-17,20-methano-18-methyl-10,13-trans-prostadienoic acid |
| 527 | 229 | 9-oxo-15-hydroxy-6,20-dinor-17,19-methano-10,13-trans-prostadienoic acid |
| 528 | 230 | 9-oxo-15-hydroxy-6-nor-16-methyl-18,20-ethano-10,13-trans-prostadienoic acid |
| 529 | 231 | 9-oxo-15-hydroxy-6-nor-17,18-methano-10,13-trans-prostadienoic acid |
| 530 | 232 | 9-oxo-15-hydroxy-6-nor-17,20-methano-10,13-trans,18-prostatrienoic acid |
| 531 | 233 | 9-oxo-15-hydroxy-6-nor-16,20-methano-10,13-trans,18-prostatrienoic acid |
| 532 | 234 | 9-oxo-15-hydroxy-7-homo-16,20-methano-10,13-trans,17-prostatrienoic acid |
| 533 | 235 | 9-oxo-15-hydroxy-7-homo-17,20-ethano-10,13-trans,19-prostatrienoic acid |
| 534 | 236 | 9-oxo-15-hydroxy-7-homo-17,18-methano-10,13-trans,prostadienoic acid |
| 535 | 237 | 9-oxo-15-hydroxy-7-homo-16-methyl-18,20-(1,3-propano)-10,13-trans-prostadienoic acid |
| 536 | 238 | 9-oxo-15-hydroxy-2-phenyl-17,18-methano-10,13-trans-prostadienoic acid |
| 537 | 239 | 9-oxo-15-hydroxy-2-phenyl-17-methyl-20-nor-16,18-ethano-10,13-trans-prostadienoic acid |
| 538 | 240 | 9-oxo-15-hydroxy-2-phenyl-16,20-(1,3-propano)-10,13-trans-prostadienoic acid |

TABLE 17-continued

| Example | Starting 11α-hydroxy-9-oxo derivative of Example | 9-oxo-Δ$^{10(11)}$- derivative and 15-epi isomers thereof |
|---|---|---|
| 539 | 241 | 9-oxo-15-hydroxy-2-phenyl-16-methyl-18,20-ethano-10,13-trans-prostadienoic acid |
| 540 | 242 | 9-oxo-15-hydroxy-2-phenyl-19,20-(1,4-butano)-10,13-trans-prostadienoic acid |
| 541 | 243 | 9-oxo-15-hydroxy-2-phenyl-17,20-methano-10,13-trans,18-prostatrienoic acid |
| 542 | 244 | 9-oxo-15-hydroxy-2-phenyl-16,20-methano-10,13-trans,18-prostatrienoic acid |
| 543 | 245 | ethyl 9-oxo-15-hydroxy-17-methyl-17,20-ethano-10,13-trans-prostadienoate |
| 544 | 246 | methyl 9-oxo-15-hydroxy-17,20-ethano-10,13-trans,19-prostatrienoate |
| 545 | 247 | l methyl 9-oxo-15-hydroxy-16,20-methano-10,13-trans,17-prostatrienoate |
| 546 | 248 | l methyl 9-oxo-15-hydroxy-17,18-methano-10,13-trans-prostadienoate |
| 547 | 249 | l methyl 9-oxo-15-hydroxy-16-methyl-18,20-(1,3-propano)-10,13-trans-prostadienoate |
| 548 | 250 | l methyl 9-oxo-15-hydroxy-17,20-ethano-20-methyl-10,13-trans-prostadienoate |
| 549 | 251 | d methyl 9-oxo-15-hydroxy-17,20-(1,4-butano)-10,13-trans-prostadienoate |
| 550 | 252 | d methyl 9-oxo-15-hydroxy-16-ethyl-19,20-(1,3-propano)-10,13-trans-prostadienoate |
| 551 | 253 | d methyl 9-oxo-15-hydroxy-17,18-methano-10,13-trans-prostadienoate |
| 552 | 254 | d methyl 9-oxo-15-hydroxy-16,20-methano-10,13-trans,18-prostatrienoate |
| 553 | 255 | d methyl 9-oxo-15-hydroxy-17,20-methano-10,13-trans,18-prostatrienoate |
| 554 | 256 | butyl 9-oxo-15-hydroxy-17,18-methano-10,13-trans-prostadienoate |
| 555 | 257 | butyl 9-oxo-15-hydroxy-16,20-methano-10,13-trans,17-prostatrienoate |
| 556 | 258 | isopropyl 9-oxo-15-hydroxy-16-methyl-18,20-(1,3-propano)-10,13-trans-prostadienoate |
| 557 | 259 | isopropyl 9-oxo-15-hydroxy-19,20-(1,4-butano)-10,13-trans-prostadienoate |
| 558 | 260 | decyl 9-oxo-15-hydroxy-17,20-methano-18-methyl-10,13-trans-prostadienoate |
| 559 | 261 | decyl 9-oxo-15-hydroxy-17,18-methano-10,13-trans-prostadienoate |
| 560 | 262 | decyl 9-oxo-15-hydroxy-17,20-ethano-10,13-trans-18- prostatrienoate |
| 561 | 263 | 9-oxo-15-hydroxy-17,20-methano-10,5-cis,13-trans-prostatrienoic acid |
| 562 | 264 | 9-oxo-15-hydroxy-18,20-ethano-10,5-cis,13-trans-prostatrienoic acid |
| 563 | 265 | 9-oxo-15-hydroxy-20-cyclopentyl-10,5-cis,13-trans-prostatrienoic acid |
| 564 | 266 | 9-oxo-15-hydroxy-16-ethyl-19,20-(1,3-propano)-10,5-cis,13-trans-prostatrienoic acid |
| 565 | 267 | 9-oxo-15-hydroxy-18,20-(1,3-propano)-10,5-cis,13-trans-prostatrienoic acid |
| 566 | 268 | 9-oxo-15-hydroxy-17,20-(1,3-propano)-10,5-cis,13-trans-prostatrienoic acid |
| 567 | 269 | 9-oxo-15-hydroxy-17,19-(1,3-propano)-10,5-cis,13-trans-prostatrienoic acid |
| 568 | 270 | 9-oxo-15-hydroxy-17,18-methano-5-cis,10,13-trans-prostatrienoic acid |
| 569 | 271 | 9-oxo-15-hydroxy-17,20-methano-5-cis,10,13-trans,18-prostatetraenoic acid |
| 570 | 272 | 9-oxo-15-hydroxy-16,20-methano-5-cis,10,13-trans,17-prostatetraenoic acid |
| 571 | 273 | l methyl 9-oxo-15-hydroxy-19,20-(1,3-propano)-5-cis,10,13-trans-prostatrienoate |
| 572 | 274 | l methyl 9-oxo-15-hydroxy-16-methyl-18,20-ethano-5-cis,10,13-trans-prostatrienoate |
| 573 | 275 | l methyl 9-oxo-15-hydroxy-20-methyl-19,20-(1,3-propano)-5-cis,10,13-trans-prostatrienoate |
| 574 | 276 | l methyl 9-oxo-15-hydroxy-17,20-ethano-5-cis,10,13-trans-prostatrienoate |
| 575 | 277 | l methyl 9-oxo-15-hydroxy-17,18-methano-5-cis,10,13-trans-prostatrienoate |
| 576 | 278 | l methyl 9-oxo-15-hydroxy-16-methyl-18,20-(1,3-propano)-5-cis,10,13-trans-prostatrienoate |
| 577 | 279 | l methyl 9-oxo-15-hydroxy-20-methyl-17,20-(1,3-propano)-5-cis,10,13-trans-prostatrienoate |
| 578 | 280 | l methyl 9-oxo-15-hydroxy-17,20-(1,4-butano)-5-cis,10,13-trans-prostatrienoate |
| 579 | 281 | l methyl 9-oxo-15-hydroxy-17,20-ethano-20-methyl-5-cis,10,13-trans-prostatrienoate |
| 580 | 282 | l methyl 9-oxo-15-hydroxy-17,20-ethano-5-cis,10,13-trans,18-prostatetraenoate |
| 581 | 283 | l methyl 9-oxo-15-hydroxy-16,20-methano-5-cis,10,13-trans,18-prostatetraenoate |
| 582 | 284 | 9-oxo-15-hydroxy-7,20-bisnor-17,19-methano-5-cis,10,13-trans-prostatrienoic acid |
| 583 | 285 | 9-oxo-15-hydroxy-7-nor-18,20-ethano-5-cis,10,13-trans-prostatrienoic acid |
| 584 | 286 | 9-oxo-15-hydroxy-7-nor-16-methyl-18,20-ethano-5-cis,10,13-trans-prostatrienoic acid |

TABLE 17-continued

| Example | Starting 11α-hydroxy-9-oxo derivative of Example | 9-oxo-$\Delta^{10(11)}$- derivative and 15-epi isomers thereof |
|---|---|---|
| 585 | 287 | 9-oxo-15-hydroxy-7-nor-20-methyl-17,20-(1,3-propano)-5-cis,13-trans-prostatrienoic acid |
| 586 | 288 | 9-oxo-15-hydroxy-7-nor-17,18-methano-5-cis,13-trans-prostatrienoic acid |
| 587 | 289 | 9-oxo-15-hydroxy-7-nor-17,20-ethano-20-methyl-5-cis,10,13-trans-prostatrienoic acid |
| 588 | 290 | 9-oxo-15-hydroxy-7-nor-17,20-methano-5-cis,10,13-trans,18-prostatetraenoic acid |
| 589 | 291 | 9-oxo-15-hydroxy-7-nor-16,20-methano-5-cis,10,13-trans,17-prostatetraenoic acid |
| 590 | 292 | 9-oxo-15-hydroxy-7a-homo-16,20-methano-5-cis,10,13-trans,18-prostatetraenoic acid |
| 591 | 293 | 9-oxo-15-hydroxy-7a-homo-17,20-methano-5-cis,10,13-trans,18-prostatetraenoic acid |
| 592 | 294 | 9-oxo-15-hydroxy-7a,7b-bishomo-17,20-ethano-5-cis,10,13-trans,18-prostatetraenoic acid |
| 593 | 295 | 9-oxo-15-hydroxy-7a,7b-bishomo-16,20-methano-5-cis,10,13-trans,17-prostatetraenoic acid |
| 594 | 296 | 9-oxo-15-hydroxy-7a-homo-17,18-methano-5-cis,10,13-trans-prostatrienoic acid |
| 595 | 297 | 9-oxo-15-hydroxy-7a-homo-16-methyl-18,20-(1,3-propano)-5-cis,10,13-trans-prostatrienoic acid |
| 596 | 298 | 9-oxo-15-hydroxy-7a-homo-19,20-(1,3-propano)-5-cis,10,13-trans-prostatrienoic acid |
| 597 | 299 | 9-oxo-15-hydroxy-7a-homo-17,19-(1,3-propano)-5-cis,10,13-trans-prostatrienoic acid |
| 598 | 300 | 9-oxo-15-hydroxy-7a,7b-bishomo-17,18-methano-5 cis,10,13-trans-prostatrienoic acid |
| 599 | 301 | 9-oxo-15-hydroxy-7a,7b-bishomo-17-methyl-17,20-ethano-5-cis,10,13-trans-prostatrienoic acid |
| 600 | 302 | 9-oxo-15-hydroxy-7a,7b-bishomo-16-methyl-18,20-ethano-5-cis,10,13-trans-prostatrienoic acid |
| 601 | 303 | 9-oxo-15-hydroxy-7a,7b-bishomo-20-cyclopentyl-5-cis10,13-trans-prostatrienoic acid |
| 602 | 304 | 9-oxo-15-hydroxy-7a,7b-bishomo-17,20-ethano-20-methyl-5-cis,10,13-trans-prostatrienoic acid |
| 603 | 305 | 9-oxo-15-hydroxy-4-methyl-18,20-ethano-5-cis,10,13-trans-prostatrienoic acid |
| 604 | 306 | 9-oxo-15-hydroxy-4,16-dimethyl-18,20-ethano-5-cis,10,13-trans-prostatrienoic acid |
| 605 | 307 | 9-oxo-15-hydroxy-4-methyl-18,20-(1,3-propano)-5-cis,10,13-trans-prostatrienoic acid |
| 606 | 308 | 9-oxo-15-hydroxy-4-methyl-16,19-ethano-5-cis,10,13-trans-prostatrienoic acid |
| 607 | 309 | 9-oxo-15-hydroxy-4-methyl-17,18-methano-5-cis,10,13-trans-prostatrienoic acid |
| 608 | 310 | 9-oxo-15-hydroxy-4-methyl-17,20-methano-5-cis,10,13-trans,18-prostatetraenoic acid |
| 609 | 311 | 9-oxo-15-hydroxy-4-methyl-16,20-methano-5-cis,10,13-trans,18-prostatetraenoic acid |
| 610 | 312 | 9-oxo-15-hydroxy-4(R)-methyl-16,20-methano-5-cis,10,13-trans,17-prostatetraenoic acid |
| 611 | 313 | 9-oxo-15-hydroxy-4(R)-17,20-ethano-5-cis,10,13-trans,19-prostatetraenoic acid |
| 612 | 314 | 9-oxo-15-hydroxy-4(R)-17,18-methano-5-cis,10,13-trans-prostatrienoic acid |
| 613 | 315 | 9-oxo-15-hydroxy-4(R),16-dimethyl-18,20(1,3-propano-5-cis,10,13-trans-prostatrienoic acid |
| 614 | 316 | 9-oxo-15-hydroxy-4(R)-methyl-16,20-ethano-5-cis,10,13-trans-prostatrienoic acid |
| 615 | 317 | 9-oxo-15-hydroxy-4(R)-methyl-19,20-(1,3-propano)-5-cis,10,13-trans-prostatrienoic acid |
| 616 | 318 | 9-oxo-15-hydroxy-4(R),17-dimethyl-20-nor-16,18-ethano-5-cis,10,13-trans-prostatrienoic acid |
| 617 | 319 | 9-oxo-15-hydroxy-4-ethyl-20,20-(1,4-butano)-5-cis-10,13-trans-prostatrienoic acid |
| 618 | 320 | 9-oxo-15-hydroxy-4-ethyl-17,20-methano-18-methyl-5-cis-10,13-trans-prostatrienoic acid |
| 619 | 321 | 9-oxo-15-hydroxy-4-ethyl-17,20-ethano-5-cis,10,13-trans-prostatrienoic acid |
| 620 | 322 | 9-oxo-15-hydroxy-4-ethyl-16,20-(1,3-propano)-5-cis,10,13-trans-prostatrienoic acid |
| 621 | 323 | 9-oxo-15-hydroxy-4-ethyl-17,18-methano-5-cis,10,13-trans-prostatrienoic acid |
| 622 | 324 | 9-oxo-15-hydroxy-4-ethyl-17,20-ethano-5-cis,10,13-trans,18-prostatetraenoic acid |
| 623 | 325 | 9-oxo-15-hydroxy-4-ethyl-16,20-methano-5-cis,10,13-trans,18-prostatetraenoic acid |
| 624 | 326 | 9-oxo-15-hydroxy-4-propyl-16,20-methano-5-cis,10,13-trans,17-prostatetraenoic acid |
| 625 | 327 | 9-oxo-15-hydroxy-4-propyl-17,20-methano-5-cis,10,13-trans,18-prostatetraenoic acid |
| 626 | 328 | 9-oxo-15-hydroxy-4-propyl-17,18-methano-5-cis,10,13-trans-prostatrienoic acid |
| 627 | 329 | 9-oxo-15-hydroxy-4-propyl-18,20-ethano-5-cis,10,13-trans-prostatrienoic acid |
| 628 | 330 | 9-oxo-15-hydroxy-4-propyl-16-methyl-18,20-(1,3-propano)-5-cis,10,13-trans-prostatrienoic acid |
| 629 | 331 | 9-oxo-15-hydroxy-4-propyl-20-cyclopentyl-5-cis,10,13-trans-prostatrienoic acid |
| 630 | 332 | 9-oxo-15-hydroxy-4-propyl-20-methyl-19,20-(1,3-propano)-5-cis,10,13-trans-prostatrienoic acid |

TABLE 17-continued

| Example | Starting 11α-hydroxy-9-oxo derivative of Example | 9-oxo-Δ$^{10(11)}$- derivative and 15-epi isomers thereof |
|---|---|---|
| 631 | 333 | 9-oxo-15-hydroxy-4-propyl-17-methyl-20-nor-16,18-ethano-5-cis,10,13-trans-prostatrienoic acid |
| 632 | 334 | 9-oxo-15-hydroxy-4-propyl-16,20-methano-5-cis,10,13-trans-prostatrienoic acid |
| 633 | 335 | 9-oxo-15-hydroxy-4-propyl-17,20-(1,3-propano)-5-cis,10,13-trans-prostatrienoic acid |
| 634 | 336 | 9-oxo-15-hydroxy-4-propyl-16,20-ethano-5-cis,10,13-trans-prostatrienoic acid |

EXAMPLE 635

Preparation of 9α,11α,15-trihydroxy-17,20-ethano-13-trans,19-prostadienoic acid

A suspension of 500 mg. of methyl 9α,11α,15-trihydroxy-17,20-ethano-13-trans,19-prostadienoate (Example 395) in 10 ml. of methanol-water (1:1) containing 200 mg. of potassium hydroxide is stirred under nitrogen atmosphere at 50° C. for 1 hour. The resulting solution is then stirred at ambient temperature for 18 hours. The solution is cooled in an ice-bath, acidified with 1N hydrochloric acid and extracted several times with ether. The combined extracts are washed with saturated sodium chloride solution, dried with anhydrous magnesium sulfate and taken to dryness to give 410 mg. of product as an oil.

EXAMPLES 636 – 656

Saponification of the 9α-hydroxy esters listed in Table 18 below by the procedure described in Example 635 furnishes the corresponding product carboxylic acids.

EXAMPLE 657

A solution of 9-oxo-11α,15-dihydroxy-17,20-methano-13-trans-prostenoic acid (Example 187) in tetrahydrofuran is added to 2.2 equivalents of lithium perhydro-9b-boraphenyalyl hydride in tetrahydrofuran at −78° C. After 30 minutes the solution is diluted with water and extracted with ether. The aqueous phase is acidified, saturated with sodium chloride and extracted with ether. The combined ether extracts are dried (magnesium sulfate) and concentratd in vacuo to give 9α,11α,15-trihydroxy-17,20-methano-13-trans-protenoic acid, contaminated with 9β,11α,15-trihydroxy-17,20-methano-13-trans-prostenoic acid. The crude mixture of acids is dissolved in methylene chloride and added to a refluxing solution of 1.2 equivalents of 2,3-dichloro-5,6-dicyanobenzoquinone (DDQ) in methylene chloride. After 5 hours, the solution is cooled and filtered. The filtrate is concentrated in vacuo and the residue is purified by column chromatography to give 9α,11α-dihydroxy-15-oxo-17,20-methano-13-trans-prostenoic acid. This material is dissolved in benzene and 3.3 equivalents each of triethylamine and trimethylsilyl chloride is added. The triethylamine hydrochloride is removed by

TABLE 18

| Example | Starting 9α-hydroxy ester of Example | Product 9α-hydroxy-prostenoic acid and 15-epi isomer thereof |
|---|---|---|
| 636 | 396 | l 9α,11α,15-trihydroxy-16,20-methano-13-trans,17-prostadienoic acid |
| 637 | 397 | l 9α,11α,15-trihydroxy-17,18-methano-13-trans-prostenoic acid |
| 638 | 398 | l 9α,11α,15-trihydroxy-16-methyl-18,20-(1,3-propano)-13-trans-prostenoic acid |
| 639 | 399 | l 9α,11α,15-trihydroxy-17,20-ethano-20-methyl-13-trans-prostenoic acid |
| 640 | 400 | d 9α,11α,15-trihydroxy-17,20-(1,4-butano)-13-trans-prostenoic acid |
| 641 | 401 | d 9α,11α,15-trihydroxy-16-ethyl-19,20-(1,3-propano)-13-trans-prostenoic acid |
| 642 | 402 | d 9α,11α,15-trihydroxy-17,18-methano-13-trans-prostenoic acid |
| 643 | 403 | d 9α,11α,15-trihydroxy-16,20-methano-13-trans,18-prostadienoic acid |
| 644 | 404 | d 9α,11α,15-trihydroxy-17,20-methano-13-trans,18-prostadienoic acid |
| 645 | 422 | l 9α,11α,15-trihydroxy-19,20-(1,3-propano)-5-cis,13-trans-prostadienoic acid |
| 646 | 423 | l 9α,11α,15-trihydroxy-16-methyl-18,20-ethano-5-cis,13-trans-prostadienoic acid |
| 647 | 424 | l 9α,11α,15-trihydroxy-20-methyl-19,20-(1,3-propano)-5-cis,13-trans-prostadienoic acid |
| 648 | 425 | l 9α,11α,15-trihydroxy-17,20-ethano-5-cis,13-trans-prostadienoic acid |
| 649 | 426 | l 9α,11α,15-trihydroxy-17,18-methano-5-cis,13-trans-prostadienoic acid |
| 650 | 427 | l 9α,11α,15-trihydroxy-16-methyl-18,20-(1,3-propano)-5-cis,13-trans-prostadienoic acid |
| 651 | 428 | l 9α,11α,15-trihydroxy-20-methyl-17,20-(1,3-propano)-5-cis,13-trans-prostadienoic acid |
| 652 | 429 | l 9α,11α,15-trihydroxy-17,20-(1,4-butano)-5-cis,13-trans-prostadienoic acid |
| 653 | 430 | l 9α,11α,15-trihydroxy-17,20-ethano-20-methyl-5-cis,13-trans-prostadienoic acid |
| 654 | 431 | l 9α,11α,15-trihydroxy-17,20-ethano-5-cis,13-trans,18-prostatrienoic acid |
| 655 | 432 | l 9α,11α,15-trihydroxy-16,20-methano-5-cis,13-trans,18-prostatrienoic acid | filtration and the solution is concentrated in vacuo to give trimethylsilyl 9α,11α,-bis(trimethylsiloxy)-15-oxo-17,20 -methano-13-trans-prostenoate.

The siloxy derivative is dissolved in ether at 0° C. and 1.3 equivalents of methyl magnesium bromide in ether is added. After 12 hours the solution is poured into saturated aqueous ammonium chloride and extracted with ether. The ether is dried and concentrated in vacuo to give an oil. Hydrolysis of the siloxy function in methanol:water:acetic acid (approximately 10:1:1), gives 9α,11α,15α-trihydroxy-15β-methyl- 17,20-methano-13-trans-prostenoic acid and 9α,11α,15β(epi)-trihydroxy-15α-methyl-17,20-methano-13-trans-prostenoic acid, which are separated by chromatographic procedures.

Treatment of a solution of 9α,11α,15α-trihydroxy-15β-methyl-17,20-methano-13-trans-prostenoic acid with an excess of N-trimethylsilyldiethylamine in acetone at −45° C. gives trimethylsiloxy 9α,15α-dihydroxy-11α-trimethylsiloxy-15β-methyl-17,20-methano-13-trans-prostenoate. The resulting bis trimethylsilyl derivative is oxidized with chromic acid-pyridine in methylene chloride (Collins Reagent) to give trimethylsiloxy 9-oxo-11α-trimethylsiloxy-15α-hydroxy-15β-methyl-17,20-methano-13-trans-prostenoate, which without purification is treated with aqueous methanol containing a trace of acetic acid to furnish 9-oxo-11α,- 15α-dihydroxy-15β-methyl-17,20-methano-13-trans-prostenoic acid.

Similar treatment of the corresponding 15β-hydroxy acid gives 9-oxo-11α,15β-dihydroxy-15α-methyl-17,20-methano-13-trans-prostenoic acid.

EXAMPLES 658 – 738

Treatment of the 9-oxo-15-hydroxyprostenoic acids of Table 19 below by the sequence of reactions described in Example 657 is productive of the 9-oxo-15-hydroxy-15-methyl products of the table. Also prepared in the course of these reaction sequences are the 9α-hydroxy derivatives corresponding to the 9-oxo products of the table, and 15-keto derivatives of the 9α- and 9β-hydroxy compounds corresponding to the 9-oxo starting compounds, and the 9α- or 9β-trimethylsilyloxy trimethylsilyl esters of the 15-keto and 15-hydroxy-15-methyl compounds. In all cases both the 15α-hydroxy-15β-methyl and the 15β-hydroxy-15α-methyl products and intermediates are obtained. The epimers are separable by chromatographic procedures, usually by column or dry column chromatography, or preparative thin layer chromatography and in more difficult cases by high speed liquid chromatograph applying if necessary, the recycling technique, described hereinabove.

TABLE 19

| Example | Starting 9-oxo-15-hydroxy-derivative of Example | Product 9-oxo-15-hydroxy-15-methyl derivative and 15-epi isomer thereof |
|---|---|---|
| 658 | 189 | 9-oxo-11α,15-dihydroxy-15-methyl-18,20-ethano-13-trans-prostenoic acid |
| 659 | 190 | 9-oxo-11α,15-dihydroxy-15-methyl-19,20-(1,3-propano)-13-trans-prostenoic acid |
| 660 | 192 | 9-oxo-11α,15-dihydroxy-15-methyl-17,20-ethano-13-trans-prostenoic acid |
| 661 | 193 | 9-oxo-11α,15-dihydroxy-15-methyl-17,20-ethano-13-trans,18-prostadienoic acid |
| 662 | 194 | 9-oxo-11α,15-dihydroxy-6,7-dinor-15-methyl-20,20-(1,4-butano)-13-trans-prostenoic acid |
| 663 | 196 | 9-oxo-11α,15-dihydroxy-15-methyl-17,18-methano-13-trans-prostenoic acid |
| 664 | 197 | 9-oxo-11α,15-dihydroxy-15-methyl-5,6,7-trinor-19,20-(1,4-butano)-13-trans-prostenoic acid |
| 665 | 198 | 9-oxo-11α,15-dihydroxy-5,6,7-trinor-15-methyl-17,18-methano-13-trans-prostenoic acid |
| 666 | 199 | 9-oxo-11α,15-dihydroxy-15-methyl-17,20-ethano-13-trans,19-prostadienoic acid |
| 667 | 200 | 9-oxo-11α,15-dihydroxy-7a,7b-bishomo-15-methyl-17,18-methano-13-trans-prostenoic acid |
| 668 | 201 | 9-oxo-11α,15-dihydroxy-15-methyl-7a,7b-bishomo-20,20-(1,4-butano)-13-trans-prostenoic acid |
| 669 | 202 | 9-oxo-11α,15-dihydroxy-15-methyl-7a,7b-bishomo-17,20-ethano-13-trans,18-prostadienoic acid |
| 670 | 204 | 9-oxo-11α,15-dihydroxy-15-methyl-2-ethyl-17,20-methano-13-trans,18-prostadienoic acid |
| 671 | 206 | 9-oxo-11α,15-dihydroxy-15-methyl-2-ethyl-17,18-methano-13-trans-prostenoic acid |
| 672 | 209 | 9-oxo-11α,15-dihydroxy-2,15-dimethyl-17,18-methano-13-trans-prostenoic acid |
| 673 | 211 | 9-oxo-11α,15-dihydroxy-2,15-dimethyl-20-cyclopentyl-13-trans-prostenoic acid |
| 674 | 212 | 9-oxo-11α,15-dihydroxy-2,15-dimethyl-17,20-ethano-13-trans,18-prostadienoic acid |
| 675 | 213 | 9-oxo-11α,15-dihydroxy-3,3,15-trimethyl-17,20-ethano-13-trans,18-prostadienoic acid |
| 676 | 215 | 9-oxo-11α,15-dihydroxy-3,3,15-trimethyl-17,18-methano-13-trans-prostenoic acid |
| 677 | 218 | 9-oxo-11α,15-dihydroxy-3,3,15-trimethyl-19,20-(1,3-propano)-13-trans-prostenoic acid |
| 678 | 220 | 9-oxo-11α,15-dihydroxy-3-oxa-15-methyl-19,20-(1,3-propano)-13-trans-prostenoic acid |
| 679 | 222 | 9-oxo-11α,15-dihydroxy-15-methyl-3-oxa-17,18-methano-13-trans-prostenoic acid |
| 680 | 223 | 9-oxo-11α,15-dihydroxy-15-methyl-3-oxa-17,18-methano-13-trans-prostenoic acid |
| 681 | 225 | 9-oxo-11α,15-dihydroxy-2-fluoro-15-methyl-17,20-ethano-13-trans,18-prostadienoic acid |
| 682 | 226 | 9-oxo-11α,15-dihydroxy-15-methyl-2-fluoro-17,18-methano-13-trans-prostenoic acid |
| 683 | 229 | 9-oxo-11α,15-dihydroxy-6,20-dinor-15-methyl-17,19-methano-13-trans-prostenoic acid |
| 684 | 230 | 9-oxo-11α,15-dihydroxy-6-nor-15-methyl-17,18-methano-13-trans-prostenoic acid |

TABLE 19-continued

| Example | Starting 9-oxo-15-hydroxy-derivative of Example | Product 9-oxo-15-hydroxy-15-methyl derivative and 15-epi isomer thereof |
|---|---|---|
| 685 | 232 | 9-oxo-11α,15-dihydroxy-6-nor-15-methyl-17,20-methano-13-trans,18-prostadienoic acid |
| 686 | 234 | 9-oxo-11α,15-dihydroxy-7-homo-15-methyl-16,20-ethano-13-trans,1-prostadienoic acid |
| 687 | 236 | 9-oxo-11α,15-dihydroxy-15-methyl-7-homo-17,18-methano-13-trans-prostenoic acid |
| 688 | 238 | 9-oxo-11α,15-dihydroxy-2-phenyl-15-methyl-17,18-methano-13-trans-prostenoic acid |
| 689 | 242 | 9-oxo-11α,15-dihydroxy-2-phenyl-15-methyl-19,20-(1,4-butano)-13-trans-prostenoic acid |
| 690 | 243 | 9-oxo-11α,15-dihydroxy-2-phenyl-15-methyl-17,20-methano-13-trans,18-prostadienoic acid |
| 691 | 263 | 9-oxo-11α,15-dihydroxy-15-methyl-17,20-methano-5-cis,13-trans-prostadienoic acid |
| 692 | 264 | 9-oxo-11α,15-dihydroxy-15-methyl-18,20-ethano-5-cis,13-trans-prostadienoic acid |
| 693 | 265 | 9-oxo-11α,15-dihydroxy-15-methyl-2-cyclopentyl-5-cis,13-trans-prostadienoic acid |
| 694 | 268 | 9-oxo-11α,15-dihydroxy-15-methyl-17,20-(1,3-propano)-5-cis,13-trans-prostadienoic acid |
| 695 | 270 | 9-oxo-11α,15-dihydroxy-15-methyl-17,18-methano-5-cis,13-trans-prostadienoic acid |
| 696 | 271 | 9-oxo-11α,15-dihydroxy-15-methyl-17,20-methano-5-cis,13-trans,18-prostatrienoic acid |
| 697 | 285 | 9-oxo-11α,15-dihydroxy-7-nor-15-methyl-18,20-ethano-5-cis,13-trans-prostadienoic acid |
| 698 | 287 | 9-oxo-11α,15-dihydroxy-7-nor-15,20-dimethyl-17,20-(1,3-propano)-5-cis,13-trans-prostadienoic acid |
| 699 | 288 | 9-oxo-11α,15-dihydroxy-7-nor-15-methyl-17,18-methano-5-cis,13-trans-prostadienoic acid |
| 700 | 290 | 9-oxo-11α,15-dihydroxy-7-nor-15-methyl-17,20-methano-5-cis,13-trans,18-prostatrienoic acid |
| 701 | 293 | 9-oxo-11α,15-dihydroxy-7a-homo-15-methyl-17,20-methano-5-cis,13-trans,18-prostatrienoic acid |
| 702 | 294 | 9-oxo-11α,15-dihydroxy-7a,7b-bishomo-15-methyl-17,20-ethano-5-cis,13-trans,18-prostatrienoic acid |
| 703 | 296 | 9-oxo-11α,15-dihydroxy-7a-homo-15-methyl-17,18-methano-5-cis,13-trans-prostadienoic acid |
| 704 | 298 | 9-oxo-11α,15-dihydroxy-7a-homo-15-methyl-19,20-(1,3-propano)-5-cis,13-trans-prostadienoic acid |
| 705 | 300 | 9-oxo-11α,15-dihydroxy-7a,7b-bishomo-15-methyl-17,18-methano-5-cis,13-trans-prostadienoic acid |
| 706 | 303 | 9-oxo-11α,15-dihydroxy-7a,7b-bishomo-15-methyl-20-cyclopentyl-5-cis,13-trans-prostadienoic acid |
| 707 | 304 | 9-oxo-11α,15-dihydroxy-7a,7b-bishomo-15-methyl-17,20-ethano-20-methyl-5-cis,13-trans-prostadienoic acid |
| 708 | 305 | 9-oxo-11α,15-dihydroxy-4,15-dimethyl-18,20-ethano-5-cis,13-trans-prostadienoic acid |
| 709 | 307 | 9-oxo-11α,15-dihydroxy-4,15-dimethyl-18,20-(1,3-propano)-5-cis,13-trans-prostadienoic acid |
| 710 | 309 | 9-oxo-11α,15-dihydroxy-4,15-dimethyl-17,18-methano-5-cis,13-trans-prostadienoic acid |
| 711 | 310 | 9-oxo-11α,15-dihydroxy-4,15-dimethyl-17,20-methano-5-cis,13-trans,18-prostatrienoic acid |
| 712 | 312 | 9-oxo-11α,15-dihydroxy-4(R),15-dimethyl-16,20-methano-5-cis,13-trans,17-prostatrienoic acid |
| 713 | 313 | 9-oxo-11α,15-dihydroxy-4(R),15-dimethyl-17,20-ethano-5-cis,13-trans,18-prostatrienoic acid |
| 714 | 314 | 9-oxo-11α,15-dihydroxy-4(R),15-dimethyl-17,18-methano-5-cis,13-trans-prostadienoic acid |
| 715 | 317 | 9-oxo-11α,15-dihydroxy-4(R),15-dimethyl-19,20-(1 3-propano)-5-cis,13-trans-prostadienoic acid |
| 716 | 319 | 9-oxo-11α,15-dihydroxy-4-ethyl-15-methyl-20,20-(1,4-butano)-5-cis,13-trans-prostadienoic acid |
| 717 | 321 | 9-oxo-11α,15-dihydroxy-4-ethyl-15-methyl-17,20-ethano-5-cis,13-trans-prostadienoic acid |
| 718 | 323 | 9-oxo-11α,15-dihydroxy-4-ethyl-15-methyl-17,18-methano-5-cis,13-trans-prostadienoic acid |
| 719 | 324 | 9-oxo-11α,15-dihydroxy-4-ethyl-15-methyl-17,20-ethano-5-cis,13-trans,18-prostatrienoic acid |
| 720 | 326 | 9-oxo-11α,15-dihydroxy-4-propyl-15-methyl-16,20-methano-5-cis,13-trans,17-prostatrienoic acid |
| 721 | 328 | 9-oxo-11α,15-dihydroxy-4-propyl-15-methyl-17,18-methano-5-cis,13-trans-prostadienoic acid |
| 722 | 329 | 9-oxo-11α,15-dihydroxy-4-propyl-15-methyl-18,20-ethano-5-cis,13-trans-prostadienoic acid |
| 723 | 331 | 9-oxo-11α,15-dihydroxy-4-propyl-20-cyclopentyl-5-cis,13-trans-prostadienoic acid |
| 724 | 332 | 9-oxo-11α,15-dihydroxy-4-propyl-15,20-dimethyl-19,20-(1,3-propano)-5-cis,13-trans-prostadienoic acid |
| 725 | 636 | 1 9-oxo-11α,15-dihydroxy-15-methyl-16,20-methano-13-trans,17-prostadienoic acid |
| 726 | 637 | 1 9-oxo-11α,15-dihydroxy-15-methyl-17,18-methano-13-trans-prostenoic acid |
| 727 | 638 | 1 9-oxo-11α,15-dihydroxy-15,16-dimethyl-18,20-(1,3-propano)-13-trans-prostenoic acid |
| 728 | 640 | d 9-oxo-11α,15-dihydroxy-15-methyl-17,20-(1,4- |

TABLE 19-continued

| Example | Starting 9-oxo-15-hydroxy-derivative of Example | Product 9-oxo-15-hydroxy-15-methyl derivative and 15-epi isomer thereof |
|---|---|---|
| | | butano)-13-trans-prostenoic acid |
| 729 | 642 | d 9-oxo-11α,15-dihydroxy-15-methyl-17,18-methano-13-trans-prostenoic acid |
| 730 | 644 | d 9-oxo-11α,15-dihydroxy-15-methyl-17,20-methano-13-trans,18-prostadienoic acid |
| 731 | 645 | l 9-oxo-11α,15-dihydroxy-15-methyl-19,20-(1,3-propano)-5-cis,13-trans-prostadienoic acid |
| 732 | 646 | l 9-oxo-11α,15-dihydroxy-15-methyl-16,20-methano-5-cis,13-trans,18-prostatrienoic acid |
| 733 | 648 | l 9-oxo-11α,15-dihydroxy-15-methyl-17,20-ethano-5-cis,13-trans-prostadienoic acid |
| 734 | 649 | l 9-oxo-11α,15-dihydroxy-15-methyl-17,18-methano-5-cis,13-trans-prostadienoic acid |
| 735 | 651 | l 9-oxo-11α,15-dihydroxy-15,20-dimethyl-17,20-(1,3-propano)-5-cis,13-trans-prostadienoic acid |
| 736 | 652 | l 9-oxo-11α,15-dihydroxy-15-methyl-17,20-(1,4-butano)-5-cis,13-trans-prostadienoic acid |
| 737 | 653 | l 9-oxo-11α,15-dihydroxy-15,20-dimethyl-5-cis,13-trans-prostadienoic acid |
| 738 | 654 | l 9-oxo-11α,15-dihydroxy-15-methyl-17,20-ethano-5-cis,13-trans,18-prostatrienoic acid |

EXAMPLE 739

Preparation of 9-oxo-11α,15-dihydroxy-17,20-methanoprostanoic acid

A 2 g. sample of 9-oxo-11α,15-dihydroxy-17,20-methano-13-trans-prostenoic acid (Example 187) dissolved in 50 ml. ethanol is hydrogenated at about 30 p.s.i. in a Parr shaker using 700 mg. of 10% palladium on carbon. The catalyst is removed by filtration and the momother liquor is taken to dryness to give 2 g. of subject compound as oil.

EXAMPLES 740 – 863

Catalytic hydrogenation with 10% palladium-on-carbon catalyst by the procedure described in Example 739 of the various prostenoic acids or esters listed below in Table 20 provides the corresponding product prostanoic acids or esters of the table.

TABLE 20

| Example | Starting Prostenoic Acid or Ester of Example | Product Prostanoic Acid or Ester and 15-epi isomer thereof |
|---|---|---|
| 740 | 189 | 9-oxo-11α,15-dihydroxy-18,20-ethano-prostanoic acid |
| 741 | 190 | 9-oxo-11α,15-dihydroxy-19,20-(1,3-propano)-prostanoic acid |
| 742 | 191 | 9-oxo-11α,15-dihydroxy-16-methyl-18,20-ethano-prostanoic acid |
| 743 | 192 | 9-oxo-11α,15-dihydroxy-17,20-ethano-prostanoic acid |
| 744 | 194 | 9-oxo-11α,15-dihydroxy-6,7-dinor-20,20-(1,4-butano)-prostanoic acid |
| 745 | 196 | 9-oxo-11α,15-dihydroxy-17,18-methano-prostanoic acid |
| 746 | 197 | 9-oxo-11α,15-dihydroxy-5,6,7-trinor-19,20-(1,4-butano)-prostanoic acid |
| 747 | 198 | 9-oxo-11α,15-dihydroxy-5,6,7-trinor-17,18-methano-prostanoic acid |
| 748 | 200 | 9-oxo-11α,15-dihydroxy-7a,7b-bishomo-17,18-methano-prostanoic acid |
| 749 | 201 | 9-oxo-11α,15-dihydroxy-7a,7b-bishomo-20,20-(1,4-butano)-prostanoic acid |
| 750 | 206 | 9-oxo-11α,15-dihydroxy-2-ethyl-17,18-methano-prostanoic acid |
| 751 | 207 | 9-oxo-11α,15-dihydroxy-2-ethyl-16,19-ethano-prostanoic acid |
| 752 | 208 | 9-oxo-11α,15-dihydroxy-2,16-diethyl-19,20-(1,3-propano)-prostanoic acid |
| 753 | 209 | 9-oxo-11α,15-dihydroxy-2-methyl-17,18-methano-prostanoic acid |
| 754 | 210 | 9-oxo-11α,15-dihydroxy-2-methyl-16,20-(1,3-propano)-prostanoic acid |
| 755 | 211 | 9-oxo-11α,15-dihydroxy-2-methyl-20-cyclopentyl-prostanoic acid |
| 756 | 215 | 9-oxo-11α,15-dihydroxy-3,3-dimethyl-17,18-methano-prostanoic acid |
| 757 | 216 | 9-oxo-11α,15-dihydroxy-3,3-dimethyl-16,20-methano-prostanoic acid |
| 758 | 217 | 9-oxo-11α,15-dihydroxy-3,3,16-trimethyl-18,20-(1,3-propano)-prostanoic acid |
| 759 | 219 | 9-oxo-11α,15-dihydroxy-3-oxa-16-methyl-18,20-ethano-prostanoic acid |
| 760 | 220 | 9-oxo-11α,15-dihydroxy-3-oxa-19,20-(1,3-propano)-prostanoic acid |
| 761 | 222 | 9-oxo-11α,15-dihydroxy-3-oxa-17,18-methano-prostanoic acid |
| 762 | 226 | 9-oxo-11α,15-dihydroxy-2-fluoro-17,18-methano-prostanoic acid |
| 763 | 227 | 9-oxo-11α,15-dihydroxy-2-fluoro-16,19-methano-20-nor-prostanoic acid |
| 764 | 229 | 9-oxo-11α,15-dihydroxy-6,20-dinor-17,19-methano-prostanoic acid |
| 765 | 230 | 9-oxo-11α,15-dihydroxy-6-nor-16-methyl-18,20-ethano-prostanoic acid |
| 766 | 231 | 9-oxo-11α,15-dihydroxy-6-nor-17,18-methano-pro- |

TABLE 20-continued

| Example | Starting Prostenoic Acid or Ester of Example | Product Prostanoic Acid or Ester and 15-epi isomer thereof |
|---|---|---|
| 767 | 236 | stanoic acid<br>9-oxo-11α,15-dihydroxy-7-homo-17,18-methano-prostanoic acid |
| 768 | 237 | 9-oxo-11α,15-dihydroxy-7-homo-16-methyl-18,20-(1,3-propano)-prostanoic acid |
| 769 | 238 | 9-oxo-11α,15-dihydroxy-2-phenyl-17,18-methano-prostanoic acid |
| 770 | 240 | 9-oxo-11α,15-dihydroxy-2-phenyl-16,20-(1,3-propano)-prostanoic acid |
| 771 | 241 | 9-oxo-11α,15-dihydroxy-2-phenyl-16-methyl-18,20-ethano-prostanoic acid |
| 772 | 248 | l methyl 9-oxo-11α,15-dihydroxy-17,18-methano-prostanoate |
| 773 | 249 | l methyl 9-oxo-11α,15-dihydroxy-16-methyl-18,20-(1,3-propano)-prostanoate |
| 774 | 250 | l methyl 9-oxo-11α,15-dihydroxy-17,20-ethano-20-methyl-prostanoate |
| 775 | 251 | d methyl 9-oxo-11α,15-dihydroxy-17,20-(1,4-butano)-prostanoate |
| 776 | 252 | d methyl 9-oxo-11α,15-dihydroxy-16-ethyl-19,20-(1,3-propano)-prostanoate |
| 777 | 253 | d methyl 9-oxo-11α,15-dihydroxy-17,18-methano-prostanoate |
| 778 | 256 | butyl 9-oxo-11α,15-dihydroxy-17,18-methano-prostanoate |
| 779 | 258 | isopropyl 9-oxo-11α,15-dihydroxy-16-methyl-18,20-(1,3-propano)-prostanoate |
| 780 | 259 | isopropyl 9-oxo-11α,15-dihydroxy-19,20-(1,4-butano)-prostanoate |
| 781 | 260 | decyl 9-oxo-11α,15-dihydroxy-17,20-methano-18-methyl-prostanoate |
| 782 | 261 | decyl 9-oxo-11α,15-dihydroxy-17,18-methano-prostanoate |
| 783 | 338 | 9α,11α,15-trihydroxy-18,20-ethano-prostanoic acid |
| 784 | 339 | 9α,11α,15-trihydroxy-19,20-(1,3-propano)-prostanoic acid |
| 785 | 340 | 9α,11α,15-trihydroxy-16-methyl-18,20-ethano-prostanoic acid |
| 786 | 342 | 9α,11α,15-trihydroxy-17,20-ethano-prostanoic acid |
| 787 | 343 | 9α,11α,15-trihydroxy-6,7-dinor-20,20-(1,4-butano)-prostanoic acid |
| 788 | 345 | 9α,11α,15-trihydroxy-17,18-methano-prostanoic acid |
| 789 | 347 | 9α,11α,15-trihydroxy-5,6,7-trinor-17,18-methano-prostanoic acid |
| 790 | 349 | 9α,11α,15-trihydroxy-7a,7b-bishomo-17,18-methano-prostanoic acid |
| 791 | 350 | 9α,11α,15-trihydroxy-7a,7b-bishomo-20,20-(1,4-butano)-prostanoic acid |
| 792 | 355 | 9α,11α,15-trihydroxy-2-ethyl-17,18-methano-prostanoic acid |
| 793 | 356 | 9α,11α,15-trihydroxy-2-ethyl-16,19-ethano-prostanoic acid |
| 794 | 357 | 9α,11α,15-trihydroxy-2,16-diethyl-19,20-(1,3-propano)-prostanoic acid |
| 795 | 358 | 9α,11α,15-trihydroxy-2-methyl-17,18-methano-prostanoic acid |
| 796 | 359 | 9α,11α,15-trihydroxy-2-methyl-16,20-(1,3-propano)-prostanoic acid |
| 797 | 360 | 9α,11α,15-trihydroxy-2-methyl-20-cyclopentyl-prostanoic acid |
| 798 | 364 | 9α,11α,15-trihydroxy-3,3-dimethyl-17,18-methano-prostanoic acid |
| 799 | 365 | 9α,11α,15-trihydroxy-3,3-dimethyl-16,20-methano-prostanoic acid |
| 800 | 366 | 9α,11α,15-trihydroxy-3,3,16-trimethyl-18,20-(1,3-propano)-prostanoic acid |
| 801 | 368 | 9α,11α,15-trihydroxy-3-oxa-16-methyl-18,20-ethano-prostanoic acid |
| 802 | 369 | 9α,11α,15-trihydroxy-3-oxa-19,20-(1,3-propano)-prostanoic acid |
| 803 | 371 | 9α,11α,15-trihydroxy-3-oxa-17,18-methano-prostanoic acid |
| 804 | 375 | 9α,11α,15-trihydroxy-2-fluoro-17,18-methano-prostanoic acid |
| 805 | 376 | 9α,11α,15-trihydroxy-2-fluoro-16,19-methano-20-nor-prostanoic acid |
| 806 | 378 | 9α,11α,15-trihydroxy-6,20-dinor-17,19-methano-prostanoic acid |
| 807 | 379 | 9α,11α,15-trihydroxy-6-nor-16-methyl-18,20-ethano-prostanoic acid |
| 808 | 380 | 9α,11α,15-trihydroxy-6-nor-17,18-methano-prostanoic acid |
| 809 | 385 | 9α,11α,15-trihydroxy-7-homo-17,18-methano-prostanoic acid |
| 810 | 386 | 9α,11α,15-trihydroxy-7-homo-16-methyl-18,20-(1,3-propano)-prostanoic acid |
| 811 | 387 | 9α,11α,15-trihydroxy-2-phenyl-17,18-methano-prostanoic acid |
| 812 | 389 | 9α,11α,15-trihydroxy-2-phenyl-16,20-(1,3-propano)-prostanoic acid |
| 813 | 390 | 9α,11α-15-trihydroxy-16-methyl-18,20-ethano-prostanoic acid |

TABLE 20-continued

| Example | Starting Prostenoic Acid or Ester of Example | Product Prostanoic Acid or Ester and 15-epi isomer thereof |
|---|---|---|
| 814 | 391 | 9α,11α,15-trihydroxy-2-phenyl-19,20-(1,4-butano)-prostanoic acid |
| 815 | 397 | l methyl 9α,11α,15-trihydroxy-17,18-methano-prostanoate |
| 816 | 398 | l methyl 9α,11α,15-trihydroxy-16-methyl-18,20-(1,3-propano)-prostanoate |
| 817 | 399 | l methyl 9α,11α,15-trihydroxy-17,20-ethano-20-methyl-prostanoate |
| 818 | 400 | d methyl 9α,11α,15-trihydroxy-17,20-(1,4-butano)-prostanoate |
| 819 | 401 | d methyl 9α,11α,15-trihydroxy-16-ethyl-19,20-(1,3-propano)-prostanoate |
| 820 | 402 | d methyl 9α,11α,15-trihydroxy-17,18-methano-prostanoate |
| 821 | 405 | butyl 9α,11α,15-trihydroxy-17,18-methano-prostanoate |
| 822 | 407 | isopropyl 9α,11α,15-trihydroxy-16-methyl-18,20-(1,3-propano)-prostanoate |
| 823 | 408 | isopropyl 9α,11α,15-trihydroxy-19,20-(1,4-butano)-prostanoate |
| 824 | 409 | decyl 9α,11α,15-trihydroxy-17,20-methano-18-methyl-prostanoate |
| 825 | 410 | decyl 9α,11α,15-trihydroxy-17,18-methano-prostanoate |
| 826 | 637 | l 9α,11α,15-trihydroxy-17,18-methano-prostanoic acid |
| 827 | 638 | l 9α,11α,15-trihydroxy-16-methyl-18,20-(1,3-propano)-prostanoic acid |
| 828 | 639 | l 9α,11α,15-trihydroxy-17,20-ethano-20-methyl-prostanoic acid |
| 829 | 652 | l 9α,11α,15-trihydroxy-17,20-(1,4-butano)-prostanoic acid |
| 830 | 641 | d 9α,11α,15-trihydroxy-16-ethyl-19,20-(1,3-propano)-prostanoic acid |
| 831 | 642 | d 9α,11α,15-trihydroxy-17,18-methano-prostanoic acid |
| 832 | 643 | d 9α,11α,15-trihydroxy-16,20-methano-prostanoic acid |
| 833 | 644 | d 9α,11α,15-trihydroxy-17,20-methano-prostanoic acid |
| 834 | 658 | 9-oxo-11α,15-dihydroxy-15-methyl-18,20-ethano-prostanoic acid |
| 835 | 659 | 9-oxo-11α,15-dihydroxy-15-methyl-19,20-(1,3-propano)-prostanoic acid |
| 836 | 660 | 9-oxo-11α,15-dihydroxy-15-methyl-17,20-ethano-prostanoic acid |
| 837 | 663 | 9-oxo-11α,15-dihydroxy-15-methyl-17,18-methano-prostanoic acid |
| 838 | 667 | 9-oxo-11α,15-dihydroxy-7a,7b-bishomo-15-methyl-17,18-methano-prostanoic acid |
| 839 | 668 | 9-oxo-11α,15-dihydroxy-7a,7b-bishomo-15-methyl-20,20-(1,4-butano)-prostanoic acid |
| 840 | 671 | 9-oxo-11α,15-dihydroxy-15-methyl-2-ethyl-17,18-methano-prostanoic acid |
| 841 | 672 | 9-oxo-11α,15-dihydroxy-2,15-dimethyl-17,18-methano-prostanoic acid |
| 842 | 673 | 9-oxo-11α,15-dihydroxy-2,15-dimethyl-20-cyclopentyl-prostanoic acid |
| 843 | 676 | 9-oxo-11α,15-dihydroxy-3,3,15-trimethyl-17,18-methano-prostanoic acid |
| 844 | 677 | 9-oxo-11α,15-dihydroxy-3,3,15-trimethyl-19,20-(1,3-propano)-prostanoic acid |
| 845 | 678 | 9-oxo-11α,15-dihydroxy-3-oxa-15-methyl-19,20-(1,3-propano)-prostanoic acid |
| 846 | 679 | 9-oxo-11α,15-dihydroxy-15-methyl-3-oxa-17,18-methano-prostanoic acid |
| 847 | 681 | 9-oxo-11α,15-dihydroxy-2-fluoro-15-methyl-17,20-ethano-prostanoic acid |
| 848 | 682 | 9-oxo-11α,15-dihydroxy-2-fluoro-15-methyl-17,18-methano-prostanoic acid |
| 849 | 683 | 9-oxo-11α,15-dihydroxy-6,20-dinor-15-methyl-17,19-methano-prostanoic acid |
| 850 | 684 | 9-oxo-11α,15-dihydroxy-6-nor-15-methyl-17,18-methano-prostanoic acid |
| 851 | 687 | 9-oxo-11α,15-dihydroxy-7-homo-15-methyl-17,18-methano-prostanoic acid |
| 852 | 688 | 9-oxo-11α,15-dihydroxy-2-phenyl-15-methyl-17,18-methano-prostanoic acid |
| 853 | 689 | 9-oxo-11α,15-dihydroxy-2-phenyl-15-methyl-19,20-(1,4-butano)-prostanoic acid |
| 854 | 725 | l 9-oxo-11α,15-dihydroxy-15-methyl-16,20-methano-prostanoic acid |
| 855 | 726 | l 9-oxo-11α,15-dihydroxy-15-methyl-17,18-methano-prostanoic acid |
| 856 | 727 | l 9-oxo-11α,15-dihydroxy-15,16-dimethyl-18,20-(1,3-propano)-prostanoic acid |
| 857 | 728 | d 9-oxo-11α,15-dihydroxy-15-methyl-17,20-(1,4-butano)-prostanoic acid |
| 858 | 729 | d 9-oxo-11α,15-dihydroxy-15-methyl-17,18-methano-prostanoic acid |
| 859 | 730 | d 9-oxo-11α,15-dihydroxy-15-methyl-17,20-methano-prostanoic acid |
| 860 | 731 | l 9-oxo-11α,15-dihydroxy-15-methyl-19,20-(1,3-propano)-prostanoic acid |
| 861 | 732 | l 9-oxo-11α,15-dihydroxy-15-methyl-16,20-methano-prostanoic acid |

TABLE 20-continued

| Example | Starting Prostenoic Acid or Ester of Example | Product Prostanoic Acid or Ester and 15-epi isomer thereof |
|---|---|---|
| 862 | 733 | 1 9-oxo-11α,15-dihydroxy-15-methyl-17,20-ethano-prostanoic acid |
| 863 | 735 | 1 9-oxo-11α,15-dihydroxy-15,20-dimethyl-17,20-(1,3-propano)-prostanoic acid |

EXAMPLE 864

Preparation of 9α,11α,15-trihydroxy-17,20-methano-13-trans-prostenoic acid and 9β,11α,15-trihydroxy-17,20-methano-13-trans-prostenoic acid A solution containing 200 mg. of 9-oxo-11α,15-dihydroxy-17,20-methano-13-trans-prostenoic acid (Example 187) and 20 mg. of sodium borohydride in 1 ml. of absolute ethanol is stirred at ambient temperature for 18 hours. The solution is diluted with 30 ml. of water, acidified with 2N hydrochloric acid and extracted with ether several times. The combined extracts are washed with saturated sodium chloride, dried with anhydrous magnesium sulfate and taken to dryness to give an oily product, which is a mixture of 9α- and 9β-hydroxy derivatives, separable by chromatography.

EXAMPLE 865 – 875

Treatment of the 9-oxo derivative listed in Table 31 below with sodium borohydride in accordance with the procedure described in Example 864 is productive of the 9-hydroxy derivatives of the table. Each of these derivatives represents a mixture of 9α- and 9β-hydroxy compounds, which are separable by chromatographic procedures.

TABLE 21

| Example | Starting 9-oxo-derivative of Example | Product 9α/9β-hydroxy derivatives and 15-epi isomers thereof |
|---|---|---|
| 865 | 190 | 9α/9β,11α,15-trihydroxy-19,20-(1,3-propano)-13-trans-prostenoic acid |
| 866 | 191 | 9α/9β,11α,15-trihydroxy-16-methyl-18,20-ethano-13-trans-prostenoic acid |
| 867 | 193 | 9α/9β,11α,15-trihydroxy-17,20-ethano-13-trans,18-prostadienoic acid |
| 868 | 195 | 9α/9β,11α,15-trihydroxy-6,7-dinor-16,20-methano-13-trans,17-prostadienoic acid |
| 869 | 196 | 9α/9β,11α,15-trihydroxy-17,18-methano-13-trans-prostenoic acid |
| 870 | 208 | 9α/9β,11α,15-trihydroxy-2,16-diethyl-19,20-(1,3-propano)-13-trans-prostenoic acid |
| 871 | 209 | 9α/9β11α,15-trihydroxy-2-methyl-17,18-methano-13-trans-prostenoic acid |
| 872 | 224 | 9α/9β,11α,15-trihydroxy-3-oxa-16,20-methano-13-trans,18-prostadienoic acid |
| 873 | 270 | 9α/9β,11α,15-trihydroxy-17,18-methano-5-cis,13-trans-prostadienoic acid |
| 874 | 272 | 9α/9β,11α,15-trihydroxy-16,20-methano-5-cis,13-trans,17-prostatrienoic acid |
| 875 | 663 | 9 /9 ,11 ,15-trihydroxy-15-methyl-17,18-methano-13-trans-prostenoic acid |

EXAMPLES 876 – 889

Treatment of the prostenoic or prostanoic acids listed in Table 22 below with the inducated diazoalkane in the following manner provides the product esters of the table.

An ethereal solution containing a molar excess of diazoalkane is added to a solution of prostenoic acid in ether (or acetone). After two to four hours the solution is carefully evaporated under reduced pressure and the residual ester is purified in the usual way by chromatography on silica gel.

TABLE 22

| Example | Starting prostenoic acid of Example | Diazoalkane | Product alkyl prostenoate and 15-epi isomer thereof |
|---|---|---|---|
| 876 | 191 | diazopentane | pentyl 9-oxo-11α,15-dihydroxy-16-methyl-18,20-ethano-13-trans-prostenoate |
| 877 | 196 | diazohexane | hexyl 9-oxo-11α,15-dihydroxy-17,18-methano-13-trans-prostenoate |
| 878 | 193 | diazooctane | octyl 9-oxo-11α,15-dihydroxy-17,20-ethano-13-trans,18-prostadienoate |
| 879 | 205 | diazoheptane | heptyl 9-oxo-11α,15-dihydroxy-2-ethyl-16,20-methano-13-trans,17-prostadienoate |
| 880 | 270 | diazononane | nonyl 9-oxo-11α,15-dihydroxy-17,18-methano-5-cis-13-trans-prostadienoate |
| 881 | 271 | diazohexane | hexyl 9-oxo-11α,15-dihydroxy-17,20-methano-5-cis,13-trans,18-prostatrienoate |
| 882 | 272 | diazooctane | octyl 9-oxo-11α,15-dihydroxy-16,20-methano-5-cis,13-trans,17-prostatrienoate |
| 883 | 342 | diazononane | nonyl 9α,11α,15-trihydroxy-17,20-ethano-13-trans,18-prostadienoate |
| 884 | 345 | diazopentane | pentyl 9α,11α,15-trihydroxy-17,18-methano-13-trans-prostenoate |
| 885 | 655 | diazoethane | 1 ethyl 9α,11α,15-trihydroxy-16,20-methano-5-cis,13-trans,18-prostadienoate |
| 886 | 477 | diazomethane | methyl 9α,11α,15-trihydroxy-4-propyl-17,18- |

TABLE 22-continued

| Example | Starting prostenoic acid of Example | Diazoalkane | Product alkyl prostenoate and 15-epi isomer thereof |
|---|---|---|---|
| 887 | 494 | diazoheptane | methano-5-cis,13-trans-prostadienoate heptyl 9-oxo-15-hydroxy-17,18-methano-10,13-trans-prostadienoate |
| 888 | 663 | diazononane | nonyl 9-oxo-11α,15-dihydroxy-15-methyl-17,18-methano-13-trans-prostenoate |
| 889 | 745 | diazooctane | octyl 9-oxo-11α,15-dihydroxy-17,18-methano-prostanoate |

EXAMPLE 890

9-[(p-carboxyphenyl)hydrazono]-11α,15-dihydroxy-17,20-methano-13-trans-prostenoic acid A solution of 660 mg. of 9-oxo-11α,15-dihydroxy-17,20-methano-13-trans-prostenoic acid (Example 187) in 35 ml. of absolute alcohol containing 600 mg. of p-carboxyphenylhydrazine and one drop of glacial acetic acid is heated to boiling to effect solution then stirred at ambient temperature for 18 hours. The solution is cooled at 0° C. for several hours and the solid which is deposited is collected to give 450 mg. of product, m.p. 125° C. (gas).

EXAMPLE 890B

9-Methoxyimino-11α,15-dihydroxy-17,20-methano-13-trans-prostenoic acid

A solution of 1.17 g. of 9-oxo-11α,15-dihydroxy-17,20-methano-13-trans-prostenoic acid (Example 187) in 15 ml. of absolute alcohol containing 345 mg. of methoxyamine hydrochloride and 0.6 ml. of dry pyridine is stirred at ambient temperature for 18 hours. The resulting solution is poured into 75 ml. of saturated sodium chloride solution and extracted twice with ether. The combined extracts are washed with saturated sodium chloride solution, dried with anhydrous magnesium sulfate and taken to dryness to furnish 1.1 g. of product as a viscous oil.

EXAMPLE 890C

9-Hydroxyimino-11α,15-dihydroxy-17,20-methano-13-trans-prostenoic acid

A solution of 1.02 g. of 9-oxo-11α,15-dihydroxy-17,20-methano-13-trans-prostenoic acid (Example 187) in 20 ml. of methanol-water (1:1) containing 1 g. of hydroxylamine hydrochloride and 1.25 g. of anhydrous sodium acetate is stirred at ambient temperature for 20 hours. The solution is flooded with water and extracted several times with ether. The combined extracts are washed with saturated sodium chloride solution, dried with anhydrous magnesium sulfate and taken to dryness to give 1 g. of product as an oil.

EXAMPLES 891 – 907

Treatment of the starting 9-oxo derivatives listed in Table 23 below with hydroxylamine by the procedure of Example 890, or methoxyamine by the procedure described in Example 890B, or with thiosemicarbazide, semicarbazide or the appropriate phenylhydrazine by the procedure described in Example 890 substituting if necessary the required reagent for the p-carboxyphenylhydrazine of the Example furnishes the product 9-substituted derivatives of the table.

TABLE 23

| Example | Starting 9-oxo derivative of Example | Product 9-derivative and 15-epi isomer thereof |
|---|---|---|
| 891 | 191 | 9-(p-carboxyphenylhydrazono)-11α,15-dihydroxy-16-methyl-18,20-ethano-13-trans-prostenoic acid |
| 892 | 193 | 9-phenylhydrazono-11α,15-dihydroxy-17,20-ethano-13-trans,18-prostadienoic acid |
| 893 | 196 | 9-(p-carboxyphenylhydrazono)-11α,16-dihydroxy-17,18-methano-13-trans-prostenoic acid |
| 894 | 196 | 9(p-methylphenylhydrazono)-11α,15-dihydroxy-17,18-methano-13-trans-prostenoic acid |
| 895 | 196 | 9-(2,5-dichlorophenylhydrazono)-11α,15-dihydroxy-17,18-methano-13-trans-prostenoic acid |
| 896 | 196 | 9-methoximino-11α,15-dihydroxy-17,18-methano-13-trans-prostenoic acid |
| 897 | 273 | 1 methyl 9-(p-carboxyphenylhydrazono)-11α,15-dihydroxy-19,20-(1,3-propano)-5-cis,13-trans-protadienoate |
| 898 | 277 | 1 methyl 9-(p-carboxyphenylhydrazono)-11α,15-dihydroxy-17,18-methano-5-cis,13-trans-prostadienoate |
| 899 | 263 | 9-thiosemicarbazono-11α,15-dihydroxy-17,20-methano-5-cis,13-trans-prostadienoic acid |
| 900 | 267 | 9-oximino-11α,15-dihydroxy-18,20-(1,3-propano)-5-cis,13-trans-prostadienoic acid |
| 901 | 663 | 9-(p-carboxyphenylhydrazono)11α,15-dihydroxy-15-methyl-17,18-methano-13-trans-prostenoic acid |
| 902 | 663 | 9-(p-fluorophenylhydrazono)-11α,15-dihydroxy-15-methyl-17,18-methano-13-trans-prostenoic acid |
| 903 | 663 | 9-(p-bromophenylhydrazono)-11α,15-dihydroxy-15-methyl-17,18-methano-13-trans-prostenoic acid |
| 904 | 695 | 9-(p-carboxyphenylhydrazano)-11α,15-dihydroxy-15-methyl-17,18-methano-5-cis,13-trans-prostadienoic acid |
| 905 | 695 | 9-(3,4-bichlorophenylhydrazono)-11α,15-dihydroxy-15-methyl-17,18-methano-5-cis,13-trans-prostadienoic acid |
| 906 | 695 | 9-(o-methylphenylhydrazono)-11α,15-dihydroxy-15-methyl-17,18-methano-5-cis,13-trans-prostadienoic acid |
| 907 | 695 | 9- emicarbazano-11α,15-dihydroxy-15-methyl-17,18-methano-5-cis,13-trans-prostadienoic acid |

EXAMPLE 908

9-Oxo-15-hydroxy-17,20-methano8(12),13-trans-prostadienoic acid

A mixture of 110 mg. of 9-oxo-11α,15-dihydroxy-17,20-methano-13-trans-prostenoic acid (Example 187) in 40 ml. of 95% ethanol and 40 ml. of 1N sodium hydroxide was stirred under argon at 30°-40° C. for 1 hour. The mixture is concentrated under reduced pressure to remove ethanol, acidified with dilute hydrochloric acid and extracted with ethyl acetate. The extracts are washed, dried, evaporated and the residue is chromatographed on acid-washed silica gel to give 55 mg. of product as an oil; λ max. 278 mμ.

EXAMPLES 909 – 915

Base treatment of the starting 9-oxo-11α-hydroxy-derivative listed in Table 24 below by the procedure described in Example 908 furnishes the product 9-oxoΔ$^{8(12)}$ derivatives of the table.

TABLE 24

| Example | Starting 9-oxo-11α-hydroxy derivative of Example | Product 9-Oxo-Δ$^{8(12)}$ derivative |
|---|---|---|
| 909 | 191 | 9-oxo-15-hydroxy-16-methyl-18,20-ethano-8(12),13-trans-prostadienoic acid |
| 910 | 193 | 9-oxo-15-hydroxy-17,20-ethano-8(12),13-trans,18-prostatrienoic acid |
| 911 | 196 | 9-oxo-15-hydroxy-17,18-methano-8(12),13-trans-prostadienoic acid |
| 912 | 196 | 9-oxo-15-epi-hydroxy-17,18-methano-8(12),13-trans-prostadienoic acid |
| 913 | 264 | 9-oxo-15-hydroxy-18,20-ethano-5-cis,8(12),13-trans-prostatrienoic acid |
| 914 | 270 | 9-oxo-15-hydroxy-17,18-methano-5-cis,8(12),13-trans-prostatrienoic acid |
| 915 | 270 | 9-oxo-15-epi-hydroxy-17,18-methano-5-cis,8(12),13-trans-prostatrienoic acid |

We claim:

1. A compound selected from the group consisting of an optically active compound of the formula:

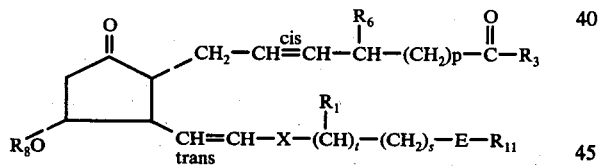

and a racemic compound of that formula and the mirror image thereof wherein p is an integer from 1 to 5, inclusive; $R_6$ is hydrogen or an alkyl group having up to four carbon atoms; $R_1$ is an alkyl group having up to three carbon atoms; X is a divalent radical selected from the group consisting of those of the formulae:

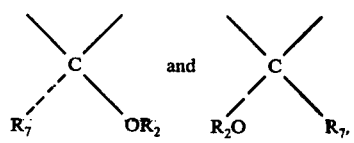

wherein $R_2$ is selected from the group consisting of hydrogen, triphenylmethyl, and mono- or di-methoxy substituted triphenylmethyl and $R_7$ is hydrogen or an alkyl group having up to three carbon atoms with the proviso that when $R_7$ is alkyl then $R_2$ must be hydrogen; $R_3$ is selected from the group consisting of hydroxy, alkoxy having up to twelve carbon atoms, tetrahydropyranyloxy and tri(lower alkyl)-silyloxy; $R_8$ is selected from the group consisting of hydrogen, tetrahydropyranyl and tri(lower alkyl)silyl; s is zero or an integer from 1 to 5, inclusive; t is zero or one; E is selected from the group consisting of cyclopropyl, cyclononyl and cycloalkenyl having from 5 to 9 carbon atoms; $R_{11}$ is selected from the group consisting of hydrogen and lower alkyl; with the proviso that when E is a saturated cycloalkyl group then the sum of s and t is at least one; and the pharmaceutically acceptable cationic salts thereof when $R_3$ is hydroxy.

2. A compound according to claim 1, wherein t, E, $R_1$ and $R_{11}$ are as previously defined; p is the integer 2; $R_2$ is hydrogen; $R_3$ is hydroxy; $R_6$ is hydrogen; $R_7$ is hydrogen and methyl; $R_8$ is hydrogen; and X is a divalent radical selected from the group consisting of those of the formulae:

3. A compound according to claim 2, wherein t, p, $R_1$, $R_2$, $R_3$, $R_6$, $R_7$, $R_8$, $R_{11}$ and X are as previously defined; and E is selected from the group consisting of $C_5$-$C_9$ cycloalkenyl.

4. A compound according to claim 2, wherein t, p, $R_1$, $R_2$, $R_3$, $R_6$, $R_7$, $R_8$, $R_{11}$ and X are as previously defined; and E is cyclopropyl and cyclononyl.

5. A compound according to claim 3, wherein t, p, $R_1$, $R_2$, $R_3$, $R_6$, $R_7$, $R_8$, X and E are as previously defined; and $R_{11}$ is hydrogen.

6. A compound according to claim 4, wherein t, p, $R_1$, $R_2$, $R_3$, $R_6$, $R_7$, $R_8$, $R_{11}$, X and E are as previously defined; and $R_{11}$ is hydrogen.

7. A compound according to claim 5, wherein p, $R_1$, $R_2$, $R_3$, $R_6$, $R_7$, $R_8$, $R_{11}$, X and E are as previously defined; and t is zero.

8. A compound according to claim 6, wherein p, $R_1$, $R_2$, $R_3$, $R_6$, $R_7$, $R_8$, $R_{11}$, X and E are as previously defined; and t is zero.

9. A compound according to claim 7, wherein t, p, $R_1$, $R_2$, $R_3$, $R_6$, $R_7$, $R_8$, $R_{11}$ and E are as previously defined; and X is

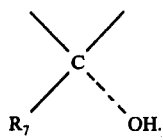

10. A compound according to claim 8, wherein $t$, $p$, $R_1$, $R_2$, $R_3$, $R_6$, $R_7$, $R_8$, $R_{11}$ and E are as previously defined; and X is

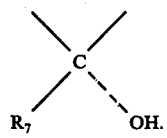

11. The compound according to claim 1, 1-9-oxo-11α,15-dihydroxy-4-n-propyl-16,20-methano-5-cis,13-trans, 17-prostatrienoic acid.

12. The compound according to claim 1, dl-9-oxo-11α,15-dihydroxy-4-n-propyl-16,20-methano-5-cis,13-trans, 17-prostatrienoic acid.

13. The compound according to claim 1, 1-9-oxo-11,15-dihydroxy-4-methyl-17,18-cis-methano-5-cis,13-trans-prostadienoic acid.

14. The compound according to claim 1, 11α-9-oxo-11,15-dihydroxy-4-methyl-17,18-cis-methano-5-cis,13-trans-prostadienoic acid.

15. The compound according to claim 4, 1-9-oxo-11α,15-epi-dihydroxy-15-methyl-17,18-cis-methano-5-cis,13-trans-prostadienoic acid.

16. The compound according to claim 4, dl-9-oxo-11α,15-epi-dihydroxy-15-methyl-17,18-cis-methano-5-cis,13-trans-prostadienoic acid.

17. The compound according to claim 4, 1-9-oxo-11α,15-dihydroxy-15-methyl-17,18-cis-methano-5-cis,13-trans-prostadienoic acid.

18. The compound according to claim 4, dl-9-oxo-11α,15-dihydroxy-15-methyl-17,18-cis-methano-5-cis,13-trans-prostadienoic acid.

19. The compound according to claim 4, 1-methyl-9-oxo-11α,15-dihydroxy-17,18-cis-methano-5-cis,13-trans-prostadienoate.

20. The compound according to claim 4, dl-methyl-9-oxo-11α,15-dihydroxy-17,18-cis-methano-5-cis,13-trans-prostadienoate.

21. The compound according to claim 4, 1-9-oxo-11α,15-epi-dihydroxy-17,18-cis-methano-5-cis,13-trans-prostadienoic acid.

22. The compound according to claim 4, dl-9-oxo-11α,15-epi-dihydroxy-17,18-cis-methano-5-cis,13-trans-prostadienoic acid.

23. The compound according to claim 4, 1-methyl 9-oxo-11α,15-epi-dihydroxy-17,18-cis-methano-5-cis,13-trans-prostadienoate.

24. The compound according to claim 4, dl-methyl 9-oxo-11α,15-epi-dihydroxy-17,18-cis-methano-5-cis,13-trans-prostadienoate.

25. The compound according to claim 7, 1-9-oxo-11α,15-epi-dihydroxy-16,20-methano-5-cis,13-trans,17-prostatrienoic acid.

26. The compound according to claim 7, dl-9-oxo-11α,15-epi-dihydroxy-16,20-methano-5-cis,13-trans,17-prostatrienoic acid.

27. The compound according to claim 7, 1-9-oxo-11α,15-epi-dihydroxy-17,20-ethano-5-cis,13-trans-18-prostatrienoic acid.

28. The compound according to claim 7, dl-9-oxo-11α,15-epi-dihydroxy-17,20-ethano-5-cis,13-trans-18-prostatrienoic acid.

29. The compound according to claim 7, 1-9-oxo-11α,15-epi-dihydroxy-15-methyl-16,20-methano-5-cis,13-trans, 18-prostatrienoic acid.

30. The compound according to claim 7, dl-9-oxo-11α,15-epi-dihydroxy-15-methyl-16,20-methano-5-cis,13-trans,18-prostatrienoic acid.

31. The compound according to claim 7, 1-9-oxo-11α,15-epi-dihydroxy-15-methyl-17,20-ethano-5-cis,13-trans,19-prostatrienoic acid.

32. The compound according to claim 7, dl-9-oxo-11α,15-epi-dihydroxy-15-methyl-17,20-ethano-5-cis,13-trans,19-prostatrienoic acid.

33. The compound according to claim 9, 1-9-oxo-11α,15-dihydroxy-16,20-methano-5-cis,13-trans,17-prostatrienoic acid.

34. The compound according to claim 9, dl-9-oxo-11α,15-dihydroxy-16,20-methano-5-cis,13-trans,17-prostatrienoic acid.

35. The compound according to claim 9, 1-9-oxo-11α,15-dihydroxy-17,20-ethano-5-cis,13-trans,18-prostatrienoic acid.

36. The compound according to claim 9, dl-9-oxo-11α,15-dihydroxy-17,20-ethano-5-cis,13-trans,18-prostatrienoic acid.

37. The compound according to claim 9, 1-9-oxo-11α,15-dihydroxy-15-methyl-16,20-methano-5-cis,13-trans,18-prostatrienoic acid.

38. The compound according to claim 9, dl-9-oxo-11α,15-dihydroxy-15-methyl-16,20-methano-5-cis,13-trans,18-prostatrienoic acid.

39. The compound according to claim 9, 1-9-oxo-11α,15-dihydroxy-15-methyl-17,20-ethano-5-cis,13-trans,19-prostatrienoic acid.

40. The compound according to claim 9, dl-9-oxo-11α,15-dihydroxy-15-methyl-17,20-ethano-5-cis,13-trans,19-prostatrienoic acid.

41. The compound according to claim 9, 1-9-oxo-11α,15-dihydroxy-17,18-cis-methano-5-cis,13-trans-prostadienoic acid.

42. The compound according to claim 9, dl-9-oxo-11α,15-dihydroxy-17,18-cis-methano-5-cis,13-trans-prostadienoic acid.

* * * * *